(12) United States Patent
Ryckman

(10) Patent No.: US 8,169,548 B2
(45) Date of Patent: *May 1, 2012

(54) LIVE BROADCAST INTERVIEW CONDUCTED BETWEEN STUDIO BOOTH AND INTERVIEWER AT REMOTE LOCATION

(75) Inventor: Lawrence G. Ryckman, Scottsdale, AZ (US)

(73) Assignee: Studio One Entertainment, Inc., Scottsdale, AZ (US)

( * ) Notice: Subject to any disclaimer, the term of this patent is extended or adjusted under 35 U.S.C. 154(b) by 1370 days.

This patent is subject to a terminal disclaimer.

(21) Appl. No.: 11/808,000

(22) Filed: May 31, 2007

(65) Prior Publication Data

US 2008/0055398 A1 Mar. 6, 2008

Related U.S. Application Data

(63) Continuation-in-part of application No. 11/648,848, filed on Dec. 29, 2006, now abandoned, and a continuation-in-part of application No. 11/648,847, filed on Dec. 19, 2006, now abandoned, and a continuation-in-part of application No. 11/648,846, filed on Dec. 29, 2006, now abandoned, and a continuation-in-part of application No. 11/648,845, filed on Dec. 29, 2006, said application No. 11/648,848 is a continuation-in-part of application No. 11/604,009, filed on Nov. 22, 2006, now abandoned, and a continuation-in-part of application No. 11/604,008, filed on Nov. 22, 2006, now abandoned, said application No. 11/648,847 is a continuation-in-part of application No. 11/604,009, filed on Nov. 22, 2006, and a continuation-in-part of application No. 11/604,008, filed on Nov. 22, 2006, now abandoned, said application No. 11/648,846 is a continuation-in-part of application No. 11/604,009, filed on Nov. 22, 2006, and a continuation-in-part of application No. 11/604,008, filed on Nov. 22, 2006, now abandoned, said application No. 11/648,845 is a continuation-in-part of application No. 11/604,009, (Continued)

(51) Int. Cl.
*H04N 5/222* (2006.01)
(52) U.S. Cl. ........................................ 348/722
(58) Field of Classification Search ............... 709/204, 709/220–229, 246; 348/722–724, 211
See application file for complete search history.

(56) References Cited

U.S. PATENT DOCUMENTS 4,735,474 A  4/1988 Allon
(Continued)

FOREIGN PATENT DOCUMENTS
WO  PCT/AU2005/000949  1/2006

*Primary Examiner* — Davetta W Goins
*Assistant Examiner* — Phylesha Dabney
(74) *Attorney, Agent, or Firm* — The Weintraub Group, P.L.C.

(57) ABSTRACT

A method to conduct a broadcast interview by producing in an area of restricted size in a realistic manner while minimizing perspective distortion and subject distortion a recording of an individual that produces the illusion that the individual is located in a larger area.

1 Claim, 44 Drawing Sheets

Related U.S. Application Data filed on Nov. 22, 2006, and a continuation-in-part of application No. 11/604,008, filed on Nov. 22, 2006, said application No. 11/604,009 is a continuation-in-part of application No. 11/526,277, filed on Sep. 22, 2006, now abandoned, said application No. 11/604,009 is a continuation-in-part of application No. 11/526,276, filed on Sep. 22, 2006, now abandoned, said application No. 11/604,009 is a continuation-in-part of application No. 11/526,274, filed on Sep. 22, 2006, now abandoned, said application No. 11/604,009 is a continuation-in-part of application No. 11/526,273, filed on Sep. 22, 2006, now abandoned, said application No. 11/604,009 is a continuation-in-part of application No. 11/526,272, filed on Sep. 22, 2006, said application No. 11/604,009 is a continuation-in-part of application No. 11/526,271, filed on Sep. 22, 2006, now abandoned, said application No. 11/604,008 is a continuation-in-part of application No. 11/526,277, filed on Sep. 22, 2006, now abandoned, said application No. 11/604,008 is a continuation-in-part of application No. 11/526,276, filed on Sep. 22, 2006, now abandoned, said application No. 11/604,008 is a continuation-in-part of application No. 11/526,274, filed on Sep. 22, 2006, now abandoned, said application No. 11/604,008 is a continuation-in-part of application No. 11/526,273, filed on Sep. 22, 2006, now abandoned, said application No. 11/604,008 is a continuation-in-part of application No. 11/526,272, filed on Sep. 22, 2006, said application No. 11/604,008 is a continuation-in-part of application No. 11/526,271, filed on Sep. 22, 2006, now abandoned.

(60) Provisional application No. 60/789,509, filed on Apr. 5, 2006, provisional application No. 60/839,967, filed on Aug. 24, 2006.

(56) References Cited

U.S. PATENT DOCUMENTS

| | | | | |
|---|---|---|---|---|
| 5,872,922 | A | 2/1999 | Hogan et al. | |
| 6,086,380 | A | 7/2000 | Chu et al. | |
| 6,205,716 | B1 | 3/2001 | Peltz | |
| 6,292,211 | B1 | 9/2001 | Pena | |
| 6,369,908 | B1 | 4/2002 | Frey et al. | |
| 6,578,008 | B1 | 6/2003 | Chacker | |
| 2003/0027120 | A1* | 2/2003 | Jean | 434/307 A |
| 2003/0049591 | A1* | 3/2003 | Fechter | 434/307 A |
| 2003/0115077 | A1* | 6/2003 | Kimura | 52/36.2 |
| 2003/0139938 | A1 | 7/2003 | Meyers | |
| 2003/0195795 | A1 | 10/2003 | Chacker | |
| 2004/0093235 | A1 | 5/2004 | Chacker | |
| 2004/0093236 | A1 | 5/2004 | Chacker | |
| 2004/0093249 | A1 | 5/2004 | Chacker | |
| 2005/0013594 | A1* | 1/2005 | Eagan | 434/307 A |
| 2005/0076376 | A1* | 4/2005 | Lind | 348/14.08 |
| 2005/0097613 | A1* | 5/2005 | Ulate et al. | 725/86 |
| 2006/0005136 | A1* | 1/2006 | Wallick et al. | 715/726 |
| 2006/0173701 | A1 | 8/2006 | Gurvey | |
| 2006/0229893 | A1 | 10/2006 | Cole | |
| 2007/0073596 | A1 | 3/2007 | Alexander et al. | |
| 2007/0236558 | A1* | 10/2007 | Ryckman et al. | 348/14.01 |
| 2007/0236585 | A1* | 10/2007 | Ryckman | 348/239 |
| 2007/0236587 | A1* | 10/2007 | Ryckman | 348/239 |
| 2007/0237496 | A1* | 10/2007 | Ryckman et al. | 386/107 |
| 2007/0238498 | A1* | 10/2007 | Ryckman et al. | 463/1 |
| 2007/0250879 | A1* | 10/2007 | Ryckman et al. | 725/91 |
| 2007/0260690 | A1 | 11/2007 | Coleman | |
| 2008/0074487 | A1* | 3/2008 | Ryckman | 348/14.1 |
| 2008/0075436 | A1* | 3/2008 | Ryckman | 386/117 |
| 2008/0115181 | A1* | 5/2008 | Ryckman et al. | 725/109 |
| 2009/0154889 | A1* | 6/2009 | Ryckman | 386/1 |

\* cited by examiner

WELCOME!

PLEASE INSERT YOUR ACTIVATION CARD IN THE SLOT BELOW.

---

SANDI MARTIN

YOUR PERFORMANCE WILL BEGIN IN:
:30 SECONDS

PLEASE USE THE JOYSTICK BELOW TO ADJUST YOUR IMAGE FOR YOUR PERFORMANCE. GOOD LUCK!

---

YOUR PERFORMANCE IS COMPLETE.

Would you like to e-mail your session to studio.com?  ☐ Yes    ☐ No

Would you like to enter the Interscope Music Contest?   ☐ Yes    ☐ No

Would you like your session sent to the studio of one talent website?   ☐ Yes    ☐ No

*FIG. 7*

ACTIVATION CARD

CONTEST DETAILS

YOU HAVE ENTERED THE INTERSCOPE RECORDS MUSIC TALENT CONTEST FOR JULY, 2006. AT LEAST ONE MINUTE OF ALL PERFORMANCES WILL BE REVIEWED BY AN INTERSCOPE REPRESENTATIVE. ENTRIES CLOSE AT MIDNIGHT JULY 31, 2006. WINNER WILL BE E-MAILED AND/OR NAME POSTED AT WWW.STUDIOONEMEDIA.COM ON JULY 5, 2006.

THE WINNER WILL RECEIVE A CASH PRIZE OF $25,000.00 AND AN ALL EXPENSES PAID TRIP TO CALIFORNIA TO AUDITION LIVE FOR INTERSCOPE. THE WINNER WILL ALSO BE AUTOMATICALLY ENROLLED IN AN ANNUAL INTERSCOPE MUSIC CONTEST WITH A GRANDPRIZE OF A $1,000,000.00 RECORDING CONTRACT.

DISCLAIMER

ALTHOUGH ALL PERFORMANCES WILL BE REVIEWED FOR AT LEAST ONE MINUTE, THERE IS NO GUARANTEEE THAT YOU WILL WIN THE CONTEST. YOU AGREE THAT YOUR PERFORMANCE TODAY IS THE PROPERTY OF INTERSCOPE RECORDS TO UTILIZE AS IT WISHES TO PROMOTE AND CONDUCT THE CONTEST.

*FIG. 10*

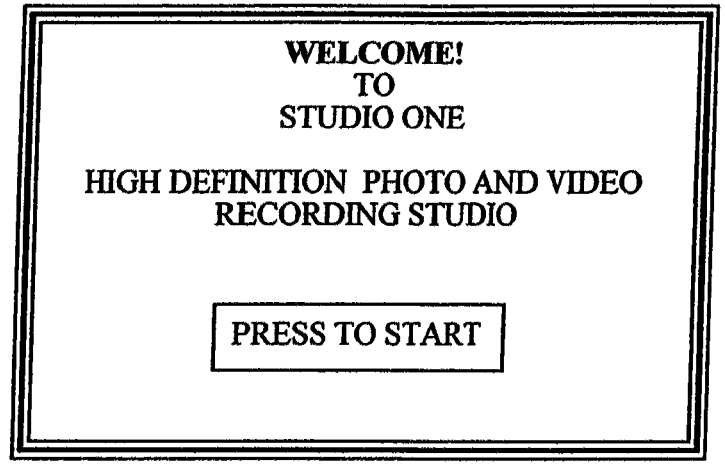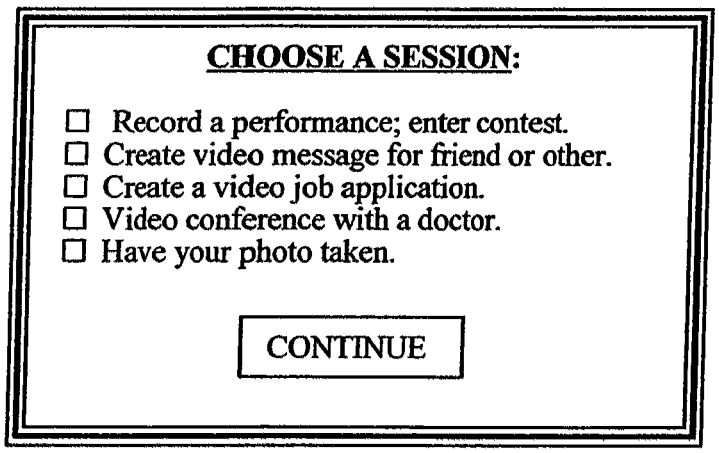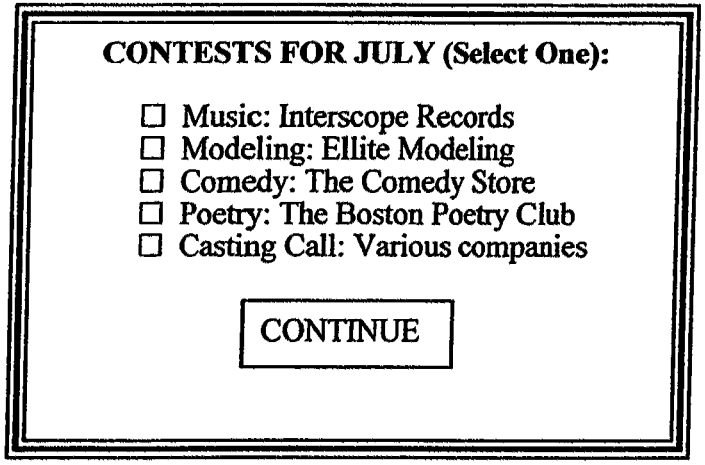
FIG. 11

CONTEST INFORMATION
Interscope Records is sponsoring the July Music Contest.. The winner will (A) receive $25,000.00 and an all expenses paid trip to California to audition live for Interscope, and (B) be entered as a finalist for a $1,000,000.00 recording contract with Interscope..

CONTINUE

CONTEST RULES
1. Enter as often as you wish. 2. All music styles accepted: rap, pop, etc. 3. At least one minute of each entry will be reviewed by Interscope. 4. The winner for July will be announce on our website on August 5, 2006. Please see the back of your activation card for more information.

CONTINUE

***OPTIONAL* INFORMATION**
Please enter your name: _____
Please enter your email address: _____
Please enter email address to receive your video
You can, if you wish, cancel this at end of session.
_____

Are you or is anyone in your recording session under 18 years of age? ☐ Yes ☐ No

Would you like to perform with background music? ☐ Yes ☐ No

[ CONTINUE ]

---

**Choose a song from our Karaoke song list.
Enter song/title:**

[                    ]

Lyrics to the song you choose will be shown on a monitor inside the studio during your session.

[ CONTINUE ]

---

WOULD YOU LIKE YOUR NAME TO APPEAR ON YOUR VIDEO.:

☐ Yes ☐ No

TO PURCHASE YOUR PERSONAL RECORDING SESSION, PLEASE PAY $20.00 BY INSERTING CASH OR CREDIT CARD.

YOUR ACTIVATION CARD WILL ISSUE BELOW.

YOU WILL NEED YOUR ACTIVATION CARD TO BEGIN YOUR SESSION.

---

WELCOME! SANDI MARTIN
YOU ARE SESSION #48.
PLEASE REMOVE YOUR ACTIVATION CARD BELOW AND INSERT INSIDE THE BOOTH WHEN YOUR SESSION IS READY. The estimated time the booth will be ready for your session is 2:30 P.M.

THANK YOU FOR VISITING STUDIO ONE!

*FIG. 14*

RECORDING BOOTH: PRE-PERFORMANCE

OWNERSHIP AND CONFIDENTIALITY

STUDIO ONE STATES (1) USER OWNS PERFORMANCE INCLUDING ANY COPYRIGHT INTEREST OF STUDIO ONE IN PERFORMANCE, (2) STUDIO ONE TRACKS AND PAYS COPYRIGHT LICENSE FEES FOR PERFORMANCE FOR MUSIC, LYRICS, ETC. ON BEHALF OF USER AND STUDIO ONE, (3) PERFORMANCE IS CONFIDENTIAL SUBJECT TO USER'S ELECTIONS.

ALTERNATIVELY, STUDIO ONE CLAIMS OWNERSHIP OF PERFORMANCE.

ACTIVATION CARD

ACTIVATION CARD INCLUDES USER ID CODE

TRANSMISSION

USER AGREES TO TRANSMISSION OF PERFORMANCE TO
1. STUDIO ONE WEB SITE/SERVER.
2. CONTEST WEB SITE/ SERVER
3. OTHER

ACCESS

USER ALLOWS/AGREES TO:

1. PUBLIC ACCESS.
2. ACCESS BY LIMITED NUMBER OF DESIGNATED PARTIES.
3. PERFORMANCE BEING INCORPORATED IN USER'S WEB SITE (VIA STUDIO ONE SITE OR E-MAIL OR OTHER).
4. USE OF PERFORMANCE IN TV SHOW, DVD, OR OTHER MEDIA.
5. USE OF PERFORMANCE IN CONTEST.

*180*

GO TO

RECORDING BOOTH: RECORDATION OF PERFORMANCE

*FIG. 20*

RECORDING BOOTH: POST-PERFORMANCE AMENDMENTS

TRANSMISSION

USER AMENDS TRANSMISSION ELECTIONS AND

1. CANCELS TRANSMISSION OF PERFORMANCE TO:
   A. STUDIO ONE WEB SITE/SERVER.
   B. CONTEST WEB SITE/ SERVER
   C. OTHER
2. TRANSMITS PERFORMANCE TO:
   A. STUDIO ONE "MY SPACE" TYPE WEB SITE
   B. OTHER

ACCESS

1. CANCELS
   A. PUBLIC ACCESS.
   B. ACCESS BY LIMITED NUMBER OF DESIGNATED PARTIES.
   C. USE OF PERFORMANCE IN TV SHOW, DVD, OR OTHER MEDIA.
   D. USE OF PERFORMANCE IN CONTEST.
2. PERMITS
   A. ACCESS TO PERFORMANCE IN STUDIO ONE "MY SPACE" TYPE WEB SITE
   B. ACCESS TO JOB INTERVIEWER
   C. ACCESS TO TALENT SCOUT
   D. PUBLIC ACCESS.
   E. ACCESS BY LIMITED NUMBER OF DESIGNATED PARTIES
   F. USE OF PERFORMANCE IN TV SHOW, DVD, OR OTHER MEDIA.
   G. USE OF PERFORMANCE IN CONTEST.
   H. OTHER

AT STUDIO ONE WEB SITE: POST PERFORMANCE

TRANSMISSION

USER DOES NOT AMEND TRANSMISSION ELECTIONS MADE IN BOOTH.

OR

USER AMENDS TRANSMISSION ELECTIONS AND

1. CANCELS TRANSMISSION OF PERFORMANCE TO:
   A. CONTEST WEB SITE/ SERVER
   B. OTHER
2. TRANSMITS PERFORMANCE TO:
   A. STUDIO ONE "MY SPACE" TYPE WEB SITE
   B. OTHER

ACCESS

USER DOES NOT AMEND ACCESS ELECTIONS MADE IN BOOTH.

OR

USER AMENDS ACCESS:

1. CANCELS
   A. PUBLIC ACCESS.
   B. ACCESS BY LIMITED NUMBER OF DESIGNATED PARTIES.
   C. USE OF PERFORMANCE IN TV SHOW, DVD, OR OTHER MEDIA.
   D. USE OF PERFORMANCE IN CONTEST.
2. PERMITS
   A. ACCESS TO PERFORMANCE IN STUDIO ONE "MY SPACE" TYPE WEB SITE
   B. ACCESS TO JOB INTERVIEWER
   C. ACCESS TO TALENT SCOUT
   D. PUBLIC ACCESS
   E. ACCESS BY LIMITED NUMBER OF DESIGNATED PARTIES.
   F. USE OF PERFORMANCE IN TV SHOW, DVD, OR OTHER MEDIA.
   G. USE OF PERFORMANCE IN CONTEST.
   H. OTHER

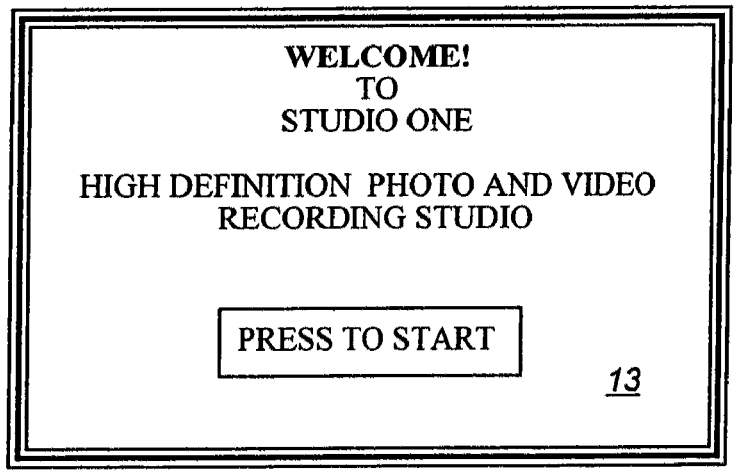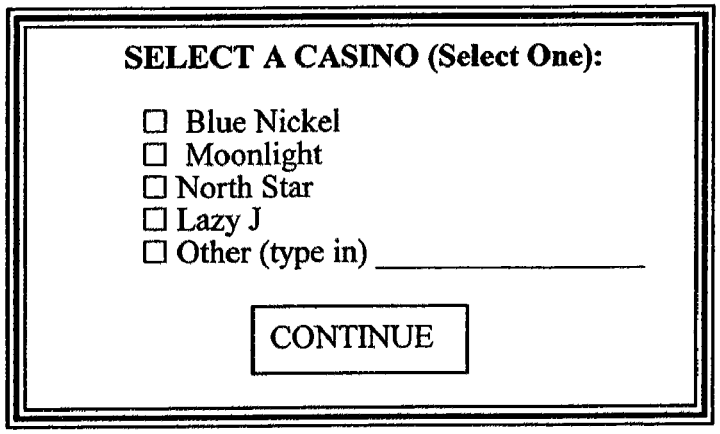
FIG. 24

THE BLUE NICKEL WELCOMES YOU!

Please enter your Account No. and Password.
ACCOUNT NO. _____
PASSWORD _____
Once these are confirmed, the next screen will appear.

---

YOUR ACCOUNT NO. AND PASSWORD HAVE BEEN VERIFIED.

PLEASE PLACE YOUR INDEX FINGER ON THE FINGERPRINT SCANNER OR USE THE OPTICAL SCANNER. After you have done so, the next screen will appear.

---

*YOUR IDENTIFY HAS BEEN CONFIRM BY THE FINGERPRINT SCANNER.*

*Please note that any transaction you have with the Blue Nickel may be monitored by IRS or other government regulatory agencies.*

*Any winnings will be sent to your account within seven (7) days.*

| CONTINUE |

*FIG. 25*

WELCOME! SANDI MARTIN
YOU ARE SESSION #52.
PLEASE REMOVE YOUR ACTIVATION CARD BELOW AND INSERT INSIDE THE BOOTH WHEN YOUR SESSION IS READY. The estimated time the booth will be ready for your session is 3:30 P.M.

PLEASE NOTE THAT the casino employee <u>*MUST BE ABLE TO SEE YOU*</u> WHEN YOU ARE IN THE BOOTH.

THANK YOU FOR VISITING STUDIO ONE!

*FIG. 26*

ACTIVATION CARD

PERFORMANCE NO. 52

SANDI MARTIN

WHEN YOU NUMBER IS DISPLAYED,
PLEASE INSERT THIS CARD INTO SLOT INSIDE THE
STUDIO TO ACTIVATE YOUR SESSION.

GAME DETAILS ARE LOCATED ON THE REVERSE OF
THIS CARD

IMPORTANT!

YOUR ACTIVATION NUMBER IS:

562389XT

USE THIS NUMBER TO ACCESS YOUR PERFORMANCE
AT:

WWW.STUDIOONEMEDIA.COM

**KEEP THIS CARD OR MAKE A COPY TO
RETAIN YOUR ACTIVATION NUMBER!**

*FIG. 27*

ACTIVATION CARD

GAME DETAILS

YOU HAVE ELECTED TO PARTICIPATE IN A GAME OF CHANCE.

IDENTIFICATION

PROPER IDENTIFICATION IS IMPORTANT IN PREVENTING ILLEGAL GAMBLING. PLEASE *HAVE YOUR ACCOUNT NUMBER AND PASSWORD READY*, IN CASE THE CASINO REQUESTS THEM WHEN YOU ARE IN THE BOOTH. IF YOU DO NOT HAVE AN ACCOUNT WITH THE CASINO YOU HAVE SELECTED, PLEASE BE READY TO ENTER THE NECESSARY INFORMATION AND HAVE YOUR DRIVER'S LICENSE AND A CREDIT CARD READY. YOU CAN ALSO *PREFERABLY* OPEN AN ACCOUNT ON-LINE BY GOING EITHER TO THE STUDIO ONE OR CASINO ADDRESS. ANY WINNINGS WILL BE WIRED BY THE CASINO TO YOUR CREDIT CARD ACCOUNT OR U.S. BANK ACCOUNT WITHIN SEVEN (7) DAYS OF YOUR WINNING.

NOTICE

THIS TRANSACTION MAY BE MONITORED BY THE INTERNAL REVENUE SERVICE (IRS) OR OTHER GOVERNMENT REGULATORY AGENCIES.

DISCLAIMER

YOU ARE PLAYING A GAME OF CHANCE. THERE IS ABSOLUTELY NO GUARANTEE THAT YOU WILL WIN. STUDIO ONE DISCLAIMS ANY AND ALL LIABILITY IN CONNECTION WITH YOUR DEALINGS WITH THE CASINO(S) THAT YOU HAVE SELECTED.

WELCOME!

PLEASE INSERT YOUR ACTIVATION CARD IN THE SLOT BELOW.

---

SANDI MARTIN

YOU WILL BE CONNECTED TO THE BLUE NICKEL WITHIN ABOUT:
:30 SECONDS

PLEASE USE THE JOYSTICK BELOW TO ADJUST YOUR IMAGE AS REQUESTED BY THE CASINO EMPLOYEE.

GOOD LUCK!

*FIG. 29*

NETWORK NODES: PRE-PERFORMANCE

| REGISTRATION AT STUDIO ONE INTERNET SITE  *100* | VIRTUAL TOUR OF STUDIO ONE BOOTH AT INTERNET SITE  *101* |

| REGISTRATION ON SITE AT STUDIO ONE BOOTH  *103* | PROMOTIONAL BANNER AND SCREENS ON EXTERIOR OF BOOTH  *104* |

NETWORK NODES: RECORDATION OF PERFORMANCE

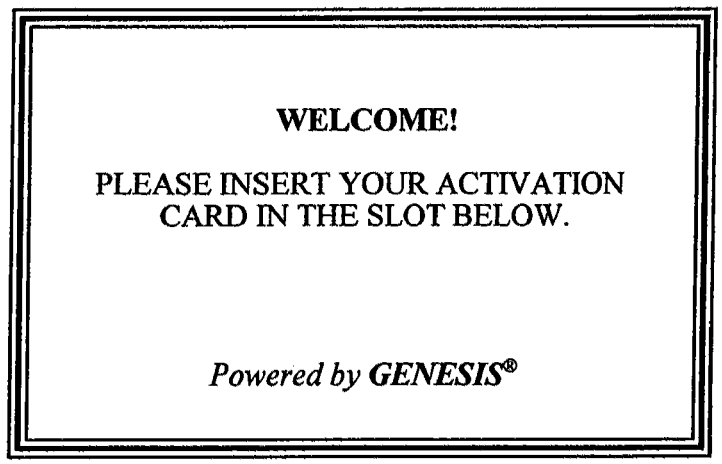
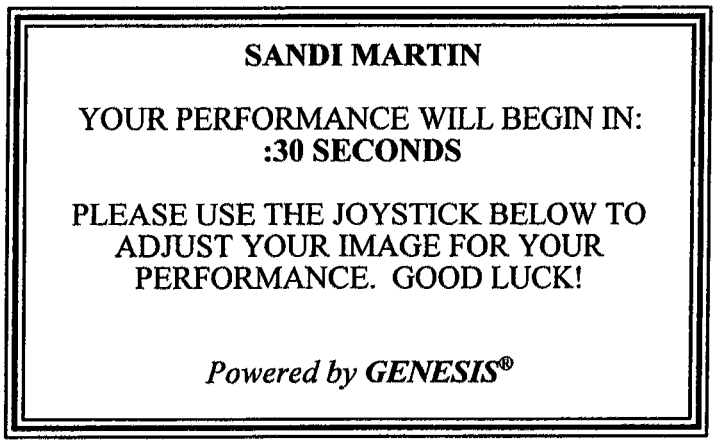
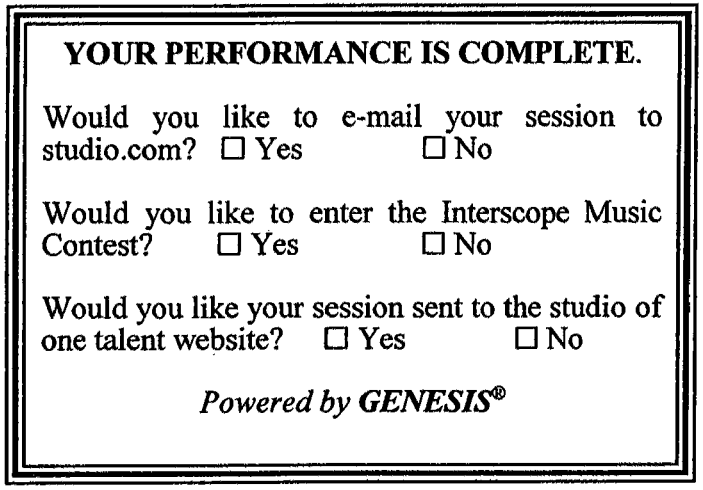
*FIG. 34*

ACTIVATION CARD

CONTEST DETAILS

YOU HAVE ENTERED THE INTERSCOPE RECORDS MUSIC TALENT CONTEST FOR JULY, 2006. AT LEAST ONE MINUTE OF ALL PERFORMANCES WILL BE REVIEWED BY AN INTERSCOPE REPRESENTATIVE. ENTRIES CLOSE AT MIDNIGHT JULY 31, 2006. WINNER WILL BE E-MAILED AND/OR NAME POSTED AT WWW.STUDIOONEMEDIA.COM ON JULY 5, 2006.

THE WINNER WILL RECEIVE A CASH PRIZE OF $25,000.00 AND AN ALL EXPENSES PAID TRIP TO CALIFORNIA TO AUDITION LIVE FOR INTERSCOPE. THE WINNER WILL ALSO BE AUTOMATICALLY ENROLLED IN AN ANNUAL INTERSCOPE MUSIC CONTEST WITH A GRAND PRIZE OF A $1,000,000.00 RECORDING CONTRACT.

DISCLAIMER

ALTHOUGH ALL PERFORMANCES WILL BE REVIEWED FOR AT LEAST ONE MINUTE, THERE IS NO GUARANTEE THAT YOU WILL WIN THE CONTEST. YOU AGREE THAT YOUR PERFORMANCE TODAY IS THE PROPERTY OF INTERSCOPE RECORDS TO UTILIZE AS IT WISHES TO PROMOTE AND CONDUCT THE CONTEST.

*Powered by GENESIS®*

*FIG. 35*

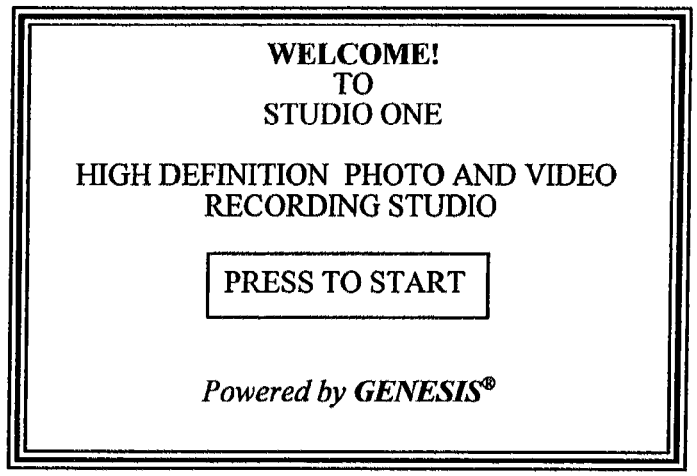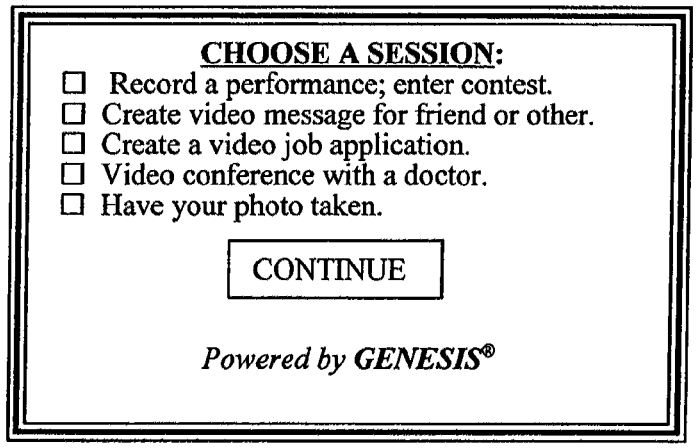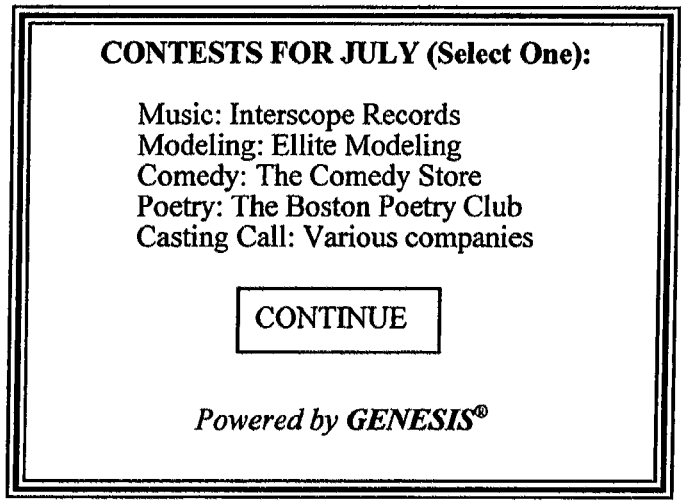
FIG. 36

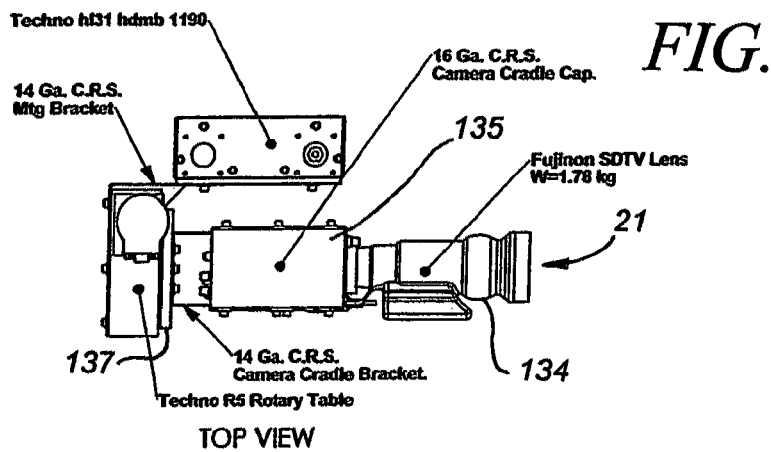
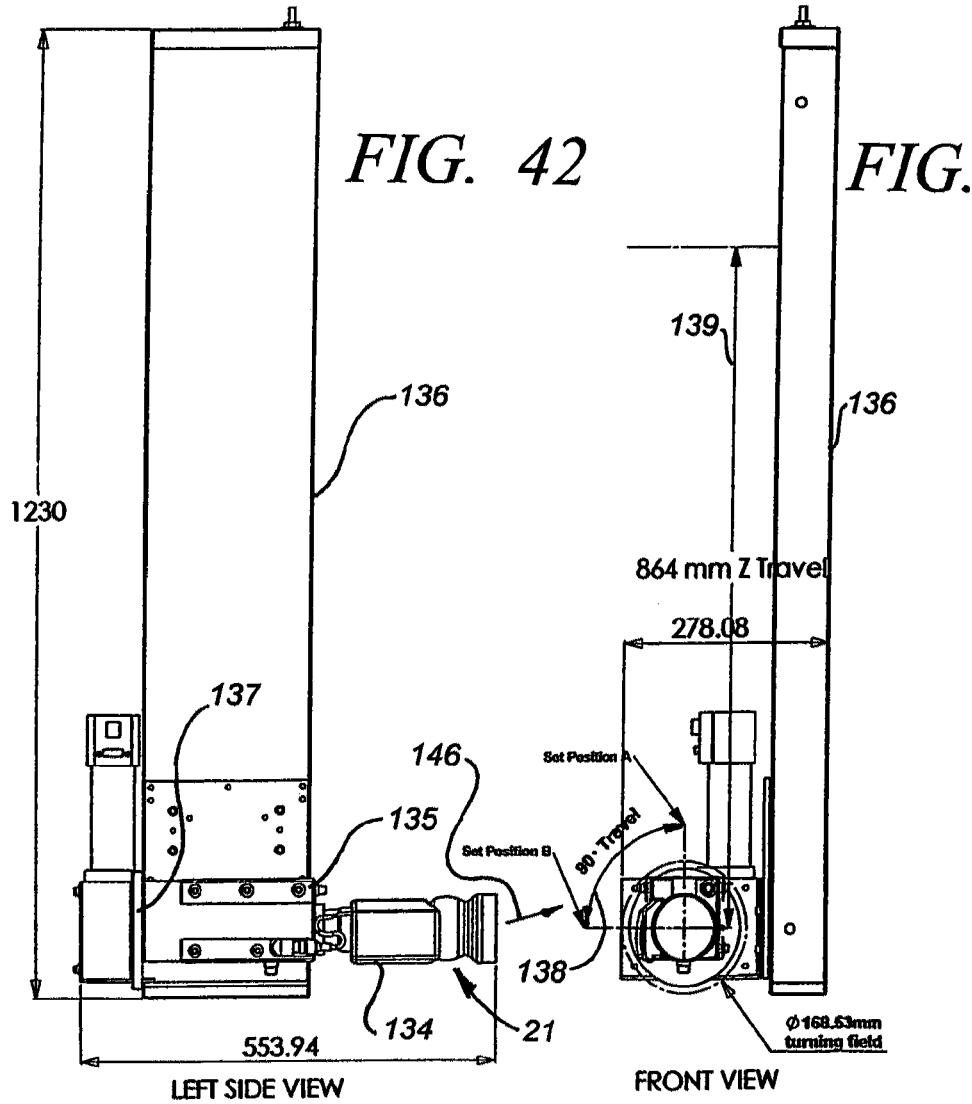

LIVE BROADCAST INTERVIEW CONDUCTED BETWEEN STUDIO BOOTH AND INTERVIEWER AT REMOTE LOCATION

This application is a continuation-in-part of
1. U.S. patent application Ser. No. 11/648,848, filed Dec. 29, 2006,
2. U.S. patent application Ser. No. 11/648,847, filed Dec. 29, 2006,
3. U.S. patent application Ser. No. 11/648,846, filed Dec. 29, 2006 now abandoned, and
4. U.S. patent application Ser. No. 11/648,845, filed Dec. 29, 2006.

Said 11/648,848, filed Dec. 29, 2006, is a continuation-in-part of
1. U.S. patent application Ser. No. 11/604,009, filed Nov. 22, 2006 now abandoned, and
2. U.S. patent application Ser. No. 11/604,008, filed Nov. 22, 2006 now abandoned.

Said 11/648,847, filed Dec. 29, 2006 is a continuation-in-part of
1. U.S. patent application Ser. No. 11/604,009, filed Nov. 22, 2006 now abandoned, and
2. U.S. patent application Ser. No. 11/604,008, filed Nov. 22, 2006 now abandoned.

Said 11/648,846, filed Dec. 29, 2006 is a continuation-in-part of
1. U.S. patent application Ser. No. 11/604,009, filed Nov. 22, 2006 now abandoned, and
2. U.S. patent application Ser. No. 11/604,008, filed Nov. 22, 2006 now abandoned.

Said 11/648,845, filed Dec. 29, 2006 is a continuation-in-part of
1. U.S. patent application Ser. No. 11/604,009, filed Nov. 22, 2006 now abandoned, and
2. U.S. patent application Ser. No. 11/604,008, filed Nov. 22, 2006 now abandoned.

Said 11/604,009, filed Nov. 22, 2006, is a continuation-in-part of
1. U.S. patent application Ser. No. 11/526,277, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
2. U.S. patent application Ser. No. 11/526,276, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
3. U.S. patent application Ser. No. 11/526,274, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
4. U.S. patent application Ser. No. 11/526,273, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
5. U.S. patent application Ser. No. 11/526,272, filed Sep. 22, 2006, which claims benefit of provisional patent application Ser. No. 60/789,509, filed Apr. 5, 2006 and which claims benefit of provisional patent application Ser. No. 60/839,967, filed Aug. 24, 2006, and
6. U.S. patent application Ser. No. 11/526,271, filed Sep. 22, 2006 now abandoned, which claims benefit of provisional patent application Ser. No. 60/789,509, filed Apr. 5, 2006 and which claims benefit of provisional patent application.

Said 11/604,008, filed Nov. 22, 2006, is a continuation-in-part of
1. U.S. patent application Ser. No. 11/526,277, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
2. U.S. patent application Ser. No. 11/526,276, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
3. U.S. patent application Ser. No. 11/526,274, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
4. U.S. patent application Ser. No. 11/526,273, filed Sep. 22, 2006 now abandoned, which claims benefit of provisional patent application Ser. No. 60/789,509, filed Apr. 5, 2006 and which claims benefit of provisional patent application Ser. No. 60/839,967, filed Aug. 24, 2006,
5. U.S. patent application Ser. No. 11/526,272, filed Sep. 22, 2006, which claims benefit of provisional patent application Ser. No. 60/789,509, filed Apr. 5, 2006 and which claims benefit of provisional patent application Ser. No. 60/839,967, filed Aug. 24, 2006, and
6. U.S. patent application Ser. No. 11/526,271, filed Sep. 22, 2006 now abandoned, which claims benefit of provisional patent application Ser. No. 60/789,509, filed Apr. 5, 2006 and which claims benefit of provisional patent application.

SUMMARY OF THE INVENTION

This invention relates to a method and apparatus for conducting a contest.

More particularly, the invention relates to a contest methodology that enables individuals to record contest performances at a plurality of different locations utilizing recording equipment of comparable quality to insure that contestants are participating on an "even playing field".

In a further respect, the invention pertains to booth in a publicly accessible location that records a variety of different performances and is adapted to transmit such performances via the Internet, video conferencing, or otherwise and to produce on site in the booth a recording of the performance.

In another respect, the invention pertains to public locations adapted to facilitate via video conferencing the renewal of prescriptions.

In still a further respect, the invention pertains to increasing the commercial viability and appeal of a recording booth to a customer by addressing confidentiality and privacy and copyright issues.

In still another respect, the invention pertains to increasing the commercial viability and appeal of a recording booth to a customer by simplifying registering to use the booth, by streamlining the process for recording a performance and producing a DVD of a performance to minimize the time a customer must be in the booth, by producing a high quality recording of a customer's performance, and by enabling the customer to distribute on multiple occasions copies of a particular performance.

In yet still a further respect, the invention pertains to a traffic generating super network that can exponentially increase the exposure to consumers of an advertiser's product or service.

In yet still another respect, the invention pertains to a method and apparatus to facilitate the integration of a scenic backdrop with a performance in a studio booth in order to provide increased flexibility in meeting the needs of individuals utilizing the booth to conduct and record performances, of entities conducting contests, and of entities utilizing the booth to record a variety of other kinds of performances.

In an additional respect, the invention pertains to a method and apparatus to format a performance to facilitate use of the performance in a studio booth.

In a further additional respect, the invention pertains to a method and apparatus that facilitates recording in a limited space in a studio a performance in a landscape or portrait orientation.

In another additional respect, the invention pertains to an activation card or other "hard" card or chip that is issued when an individual registers to utilize a studio booth and that includes—in a bar code or other data transmitting design or device on or in the card—information necessary both for the individual to enter the studio booth and conduct and record a formatted performance, and for the individual to access a copy of his or her performance on a web site.

In yet a further additional respect, the invention pertains to a method and apparatus that reduces, by writing preliminarily audio and/or video data on a DVD, the likelihood that a defective DVD will be utilized to record a performance that is conducted by an individual in a studio booth, and that therefore increases the likelihood that the individual will have to wait only a minimal amount of time to receive a DVD containing a recording of his or her performance.

In yet another additional respect, the invention pertains to a method and apparatus for management of use of a studio to facilitate a continual use of the booth and minimize scheduling conflicts amongst individuals registering to use the booth, such management comprising limiting access to a booth to individuals registering at the booth; comprising requiring that a particular booth be reserved when an individual registers to use a booth; comprising notifying the computer control system in a booth when a particular date and time has been reserved to use the booth; or, comprising other selected scheduling strategies.

U.S. Pat. No. 6,578,008 to Chacker describes a method and system in which a talent business is implemented on-line such that the public can vote on a large number of unknown artists. The talent business enters into contracts with selected artists depending on public voting. Chacker requires each artist to obtain an audio or video file. The file is uploaded to a web site. Audio and video recording equipment can be expensive, as can the costs associated with obtaining access to the equipment and to sound engineers qualified to operate the equipment. More importantly, the quality of such equipment varies widely. As a result, the equipment may produce a recording that does not accurately reflect the talent of an artist.

U.S. Pat. No. 6,369,908 to Frey et al. discloses a system which enables a user to record captured video images and copy them to a electronic storage media, as well as enabling the user to e-mail the video images to desired locations. Frey et al. does not suggest uploading the video images to a web site in the manner set forth in the above-noted Chacker reference.

U.S. Pat. No. 5,872,922 to Hogan et al. describes a video conferencing system, as does U.S. Pat. No. 6,292,211 to Pena.

The modular, portable, video conferencing booth in the Peltz reference (U.S. Pat. No. 6,205,716) can include a variety of equipment ranging from graphics and document cameras, video cassette recorder, slide projectors, fax machines, printers, personal computer, and a host of software to conduct electronic billing, scheduling software, imaging and administrative document imaging and record keeping, and carriers necessary for delivering voice transcription and to effectively conduct a two-way video conferencing session or meeting. When the Peltz booth is used by a patient to video conference with a physician, the patient can discuss compliance on a drug or homeopathic prescription and discuss if the prescription is already written. The booth can, if desired, include medical equipment such as blood pressure monitors, a dental exam camera, dermatoscopes, electrocardiography systems, electroencephalograph systems, fundoscopes, intravenous infusion pumps, opthalmoscopes, octoscopes, pulse oximeters, gastroscopes, bronchcoscopes, and videomicroscopes.

U.S. Pat. No. 6,086,380 to Chu et al. sets forth a self-operated karaoke recording booth that provides a selection of background scenes from which to choose and provides a display of the karaoke lyrics being utilized. A video camera is positioned at the user's eye level. Messages and video displays are provided the user by a video display monitor that is connected to a computer. The user's performance can be recorded on a CD or video cassette. The booth can be located in public locations or other locations such as a karaoke club, shopping mall, restaurant, and bar.

U.S. Patent Application 2005/0097613, filed May 5, 2005, to Ulate et al. discloses a recording booth that can be utilized at a private location, or, at a public location such as a shopping mall. Performances recorded in the booth can be sent to a web site or other location to be viewed and/or rated by the public, by a talent agency, by an entertainment company, by a recording studio, by a prospective employer, etc. If the person or company viewing the recording likes the recording, the person or company may hire the performer.

U.S. Patent Application No. 2003/0027120 to Jean discloses a karaoke entertainment system in which a centralized computer and server service a plurality of individual karaoke player rooms. The entertainment system can utilize videos/audios transmitted from a remote library source.

U.S. Patent Application 2006/0005136 to Wallick et al. describes a virtual video studio that is equipped to select any of a plurality of inputs and incorporate the selected input in a composite video stream.

The multimedia production and recording system in U.S. Patent Application 2003/0049591 interleaves stored recorded video segments with real time video segments.

U.S. Patent Application 2005/0013594 describes a system in which individuals make video recordings in kiosks. The video recordings are transmitted to a production studio via a computer network. The video recordings are assembled into a unified video presentation which is downloaded for playback at a particular event.

U.S. Patent Application 2003/0115077 discloses an advertising system which prepares an e-mail with an advertisement and then transmits the e-mail and advertisement.

U.S. Patent Application 2005/0076376 describes a video entertainment satellite network system. The system includes a plurality of individual video entertainment satellite systems that communicate with each other.

The Allon patent (U.S. Pat. No. 4,735,474) describes a booth that produces a hologram of an individual occupying the booth.

International Patent Application No. PCT/AU2005/000949 describes a gambling event which can be monitored by e-mail.

As is shown by the foregoing references, it is well known to utilize a booth in a public location to record a video or audio performance, to make a DVD or audio copy of the performance, to transmit the performance to a web site, to transmit the performance by e-mail, to allow the public, talent scout, or others to view and rate a performance, either via the Internet or otherwise, and to conduct a video conference with a physician or other desired individual.

As used herein, and as is commonly understood, a contest includes at least one, and normally most or all, of the following characteristics. A contest:

Has a definite termination or closing date by which each applicant must submit his or her entry.

Has a winner. This often is not the case with a rating system. Numerous job application can be presented to a potential employer or talent scout or music company to be rated, and the employer or talent scout or music company may not select any of the applicants. There is no guarantee there will be a winner.

Sets forth a specific reward to the winner, typically comprising or including a monetary award or other property.

Ordinarily is called a contest to suggest to the participants that there is a closing date and reward.

Is conducted under equivalent conditions for each player so that each player has an equal chance to win.

Provides a written set of rules.

Sets forth guidelines used to evaluate an entry in the contest.

Sets forth in writing legal disclaimers, requirements, or guidelines.

A contest is not simply a rating. One example of a rating is rating the value of a car by looking at its blue book value. Another example of a rating is a rating for an athlete obtained by determining the athlete's speed, agility, strength, etc. Such athletic ratings are routinely carried out by college and professional sports teams. Still another example of a rating is the rating by an employer of a job applicant after the employer interviews the job applicant and reviews the applicant's resume. In contrast, a contest has specific characteristics not normally associated with a rating. While studio booths can be utilized to produce recorded performances that are rated, it is believed a studio booth system tailored to conduct a contest would be more effective in generating a wide range of interest and participation.

Accordingly, it would be highly desirable to provide an improved studio booth system that could be utilized to produce recorded performances in the context of a contest or of being rated or otherwise utilized.

Therefore, it is a principal object of the invention to provide an improved system of studio recording sites.

Another object of the invention is to provide a contest system that utilizes easily accessible dispersed recording studios.

A further object of the invention is to provide a network of studio booths that each utilize equivalent equipment to produce a recording of a performance by an individual.

BRIEF DESCRIPTION OF THE DRAWINGS

These and other, further and more specific objects and advantages of the invention will be apparent to those of skill in the art from the following detailed description thereof, taken in conjunction with the drawings, in which:

FIG. 7 is a diagram illustrating a sequential series of communications to an individual inside the studio booth after the individual has activated the booth by inserting an activation card;

FIG. 10 is a back view further illustrating the activation card of FIG. 9;

FIG. 11 is a diagram illustrating a sequence of communications to an individual who is standing outside the studio booth and registering to utilize the booth;

FIG. 12 is a diagram illustrating a sequence of communications that are subsequent to the communications of FIG. 11 and that are directed to an individual who is standing outside the studio booth and registering to utilize the booth;

FIG. 13 is a diagram illustrating a sequence of communications that are subsequent to the communications of FIG. 12 and that are directed to an individual who is standing outside the studio booth and registering to utilize the booth;

FIG. 14 is a diagram illustrating a sequence of communications that are subsequent to the communications of FIG. 13 and that are directed to an individual who is standing outside the studio booth and registering to utilize the booth;

FIG. 20 is a diagram illustrating the first phase in another ownership-confidentiality embodiment of the invention;

FIG. 22 is a diagram illustrating possible post-performance amendments in the recording booth;

FIG. 23 is a diagram illustrating another phase in the ownership-confidentiality embodiment of FIG. 20;

FIG. 24 is a diagram illustrating a sequence of communications to an individual who is standing outside the studio booth and registering to utilize the booth to participate in a game of chance;

FIG. 25 is a diagram illustrating a sequence of communications that are subsequent to the communications of FIG. 24 and that are directed to an individual who is standing outside the studio booth and registering to utilize the booth to participate in a game of chance;

FIG. 26 is a diagram illustrating an additional communication subsequent to the communications of FIG. 25 and that is directed to an individual who is standing outside the studio booth and registering to utilize the booth to participate in a game of chance;

FIG. 27 is a top view illustrating an activation card printed for an individual who has paid to utilize the studio booth to participate in a game of chance;

FIG. 28 is a back view further illustrating the activation card of FIG. 27;

FIG. 29 is a diagram illustrating a sequential series of communications to an individual inside the studio booth to play a game of chance after the individual has activated the booth by inserting an activation card in a card reading device inside the booth;

FIG. 34 is a diagram illustrating screens available for advertising while an individual is conducting and recording a performance in a studio booth;

FIG. 35 is a diagram illustrating an activation card available for advertising when an individual registers to utilize and studio booth and when the individual actually uses the studio booth to conduct and record a performance;

FIG. 36 is a diagram illustrating screens available for advertising while an individual is registering to utilize a studio booth;

FIG. 40 is a top view illustrating a camera system utilized in a studio booth;

FIG. 41 is a front view of the camera system of FIG. 40 illustrating the mode of operation thereof;

FIG. 42 is a side view illustrating further construction details of the camera of FIG. 40;

DETAILED DESCRIPTION OF THE INVENTION

Figure 1:
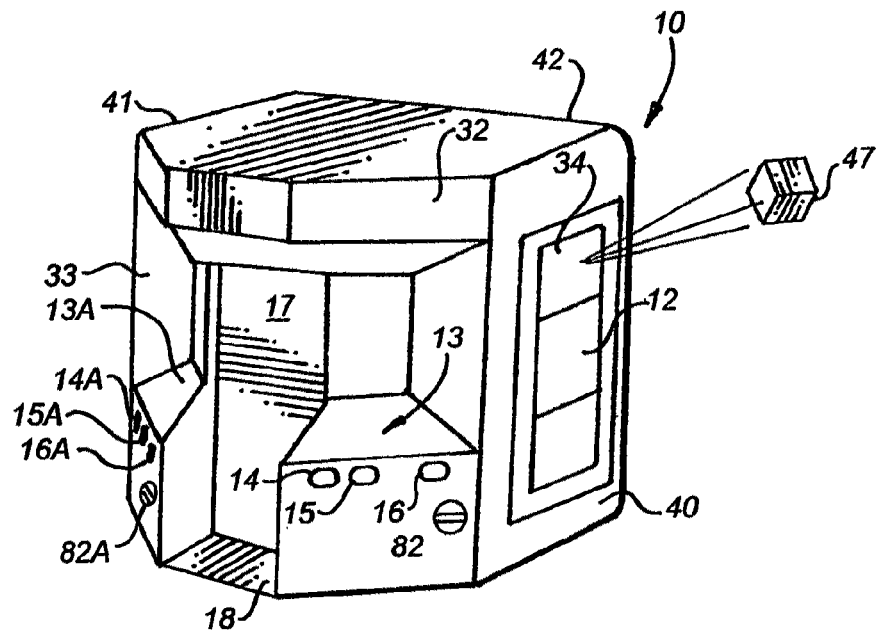
FIG. 1 is a perspective view illustrating a studio booth constructed in accordance with the principles of the invention.
Figure 2:
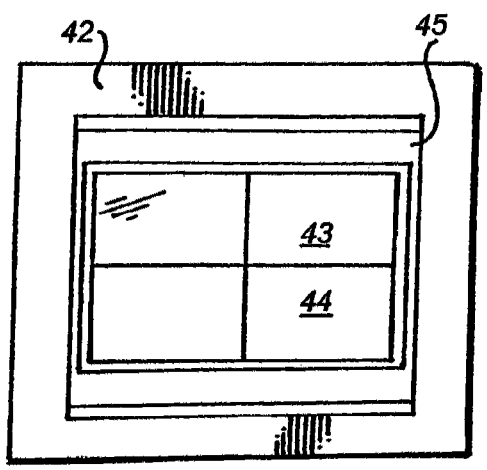
FIG. 2 is a rear view of the studio booth of FIG. 1 illustrating further construction details thereof.
Figure 3:
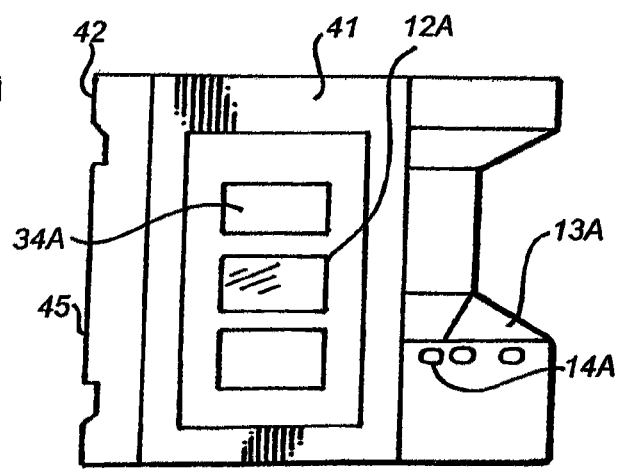
FIG. 3 is a left side view illustrating the studio booth of FIG. 1.
Figure 4:
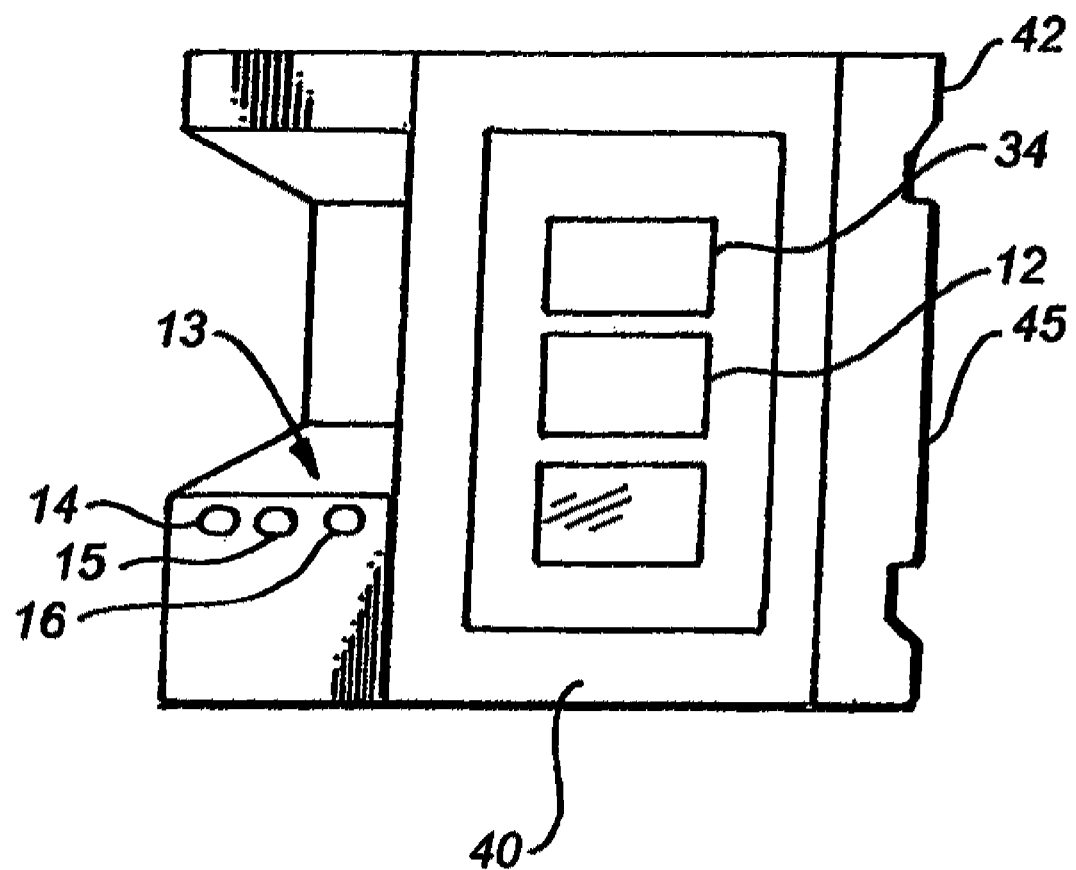
FIG. 4 is a right side view illustrating the studio booth of FIG. 1.

Briefly, in accordance with the invention, provided is an interactive personal service provider for video communication having a studio. The studio includes an audio and video recorder to record at least one performance thereby making a recorded performance; at least one computer server for storing the recorded performance. The computer server comprises an audio and video player to preview the recorded performance, and a database to receive input information from a studio user that relates to the recorded performance. The studio also comprises a communication connection to transmit the recorded performance to a studio site maintained by a studio operator wherein the recorded performance is categorized and wherein the site enables a plurality of viewers to view the recorded performance. An information seeker can query said input information. The recorded performance can comprise a Karaoke-style performance performed in the studio. The studio site can comprise a website. A menu on the studio site can be provided to list subject matter and predetermine main categories and sub-categories. The interactive service provider can have a video conferencing capability. The interactive service provider can further comprise a rating means to enable the viewer to rate the recorded performance.

In another embodiment of the invention, provided is a method for placing a performance of a studio user on a studio site. The method comprises the steps of providing a studio in a public location wherein the studio comprises and audio and video recording capability; recording a performance of a studio user in the studio on a studio server to create a recorded performance; categorizing the recorded performance by subject matter in a database; and, making the recorded performance accessible from a studio site maintained by a studio operator. The studio can be substantially soundproof. The studio user can agree to an exclusive agency contract with a studio operator before or after recording a performance. The recorded performance can comprise at least two studio users in at least two separate locations.

In a further embodiment of the invention, provided is a method to recruit talent. The method includes the steps of providing a studio in a public place for at least one studio user to record a performance; recording the performance in the studio on a studio server to make a recorded performance; and, transmitting the recorded performance to an information seeker. The studio user can provide demographic information. A talent seeker can be permitted to access the demographic information. The demographic information can be transmitted to a talent seeker. The video can be rated by members of the public or by any other desired party(s).

In still another embodiment of the invention, provided is an apparatus for distributing information to at least one information seeker. The apparatus comprises at least two studio booths wherein each studio booth is equipped with an audio and video recording device and is located in a publicly accessible location; and, a studio site connected to each of the studio booth where a plurality of studio users can access one of the plurality of studio booths to upload a performance. Each booth can further comprise at least one server. The studio site can comprise a website. At least two studio booths can be located in different geographical locations.

In still a further embodiment of the invention, provided is apparatus to conduct a contest in which recorded performances of different individuals are reviewed to select a winner. The apparatus comprises at least one recording booth including recording equipment and a registration station. The recording equipment comprises at least one camera for photographing the video portion of at least one individual's performance and generating video signals; at least one microphone for sensing the audio portion of the individual's performance and generating audio signals; lighting; and, performance apparatus to record video and audio signals generated by the camera and microphone and generate a recorded performance by said individual. The registration station permits an individual to enter information concerning the individual participating in the contest and to produce a control card to activate a recording session in the booth, and to set forth contest rules. The apparatus also includes apparatus for reviewing recorded performances generated by the booth to select a winner of the contest. The recorded performance can comprise a still photograph or a video of the individual.

In yet another embodiment of the invention, provided is improved apparatus to conduct a contest in which recorded performances of different individuals are reviewed to select a winner. The apparatus comprises a least one recording booth. The booth includes recording equipment comprising at least one camera for photographing the video portion of at least one individual's performance and generating video signals; at least one microphone for sensing the audio portion of the individual's performance and generating audio signals; lighting; performance apparatus to record video and audio signals generated by the camera and microphone and generate a recorded performance by the individual; and, a display viewable by the individual indicating the individual's ownership of the recorded performance and the control by the individual of the confidentiality of the performance.

In yet a further embodiment of the invention, provided is apparatus to participate in a game of chance. The apparatus comprises a plurality of recording booths each including video conferencing equipment to communicate between the booth and a casino at a location remote from the booth and comprising at least one camera for viewing an individual situated in the booth; at least one microphone for sensing the speech of the individual; at least one display screen to display the image of a casino employee; at least one speaker to produce the voice of the casino employee; and, apparatus to transmit signals between the booth and the casino. The recording booth also includes apparatus to confirm the identity of the individual.

In an additional embodiment of the invention, provided is an improved system for recording a performance. The system has a studio comprising an audio and video system to detect and generate audio-visual signals representing at least one selected performance conducted in the studio; a computer system to generate signals representing a scenic backdrop; and, a system to integrate the background signals and the audio-visual signals to make a recorded performance. The performance can be a formatted performance. The studio can list different categories of performances. A menu at the studio can allow user-selected performance categories. The scenic backdrop can be selected based on at least one of a pair comprising geographic locale; and, desired content. The recorded performance may have to include a backdrop selected from a pre-defined list of backdrops including at least one backdrop. The recorded performance can be for entry in a category of performances comprising a contest. The recorded performance can be for entry in a category of performances comprising performances transmitted to a personal relationship web site. The recorded performance can be for entry in a category of performances comprising a portal for initial entry and registration on a personal relationship web site. The recorded performance can be used to apply for employment. The scenic backdrop can be at a location remote from the studio and stored for recall during the selected performance. The scenic backdrop can be stored at a location remote from the studio for recall during the selected performance in the studio. The studio can include a chroma key screen inside the studio to produce background light that is, along with the selected performance, detected by the audio and visual system. The scenic backdrop can be stored at the studio for recall during the selected performance in the studio. The chroma key screen can include a plurality of light reflective glass beads. The chroma key screen can be comprised of a material that is green. The studio can comprise a booth and the system can include a plurality of said booths located remote from each other. The system can include a network to receive the recorded performance. The network comprises multiple nodes including a plurality of the studio booths at separate remote locations; and, a plurality of receiving apparatus to receive at the nodes at least the recorded performance. The system can include a display in the booth indicating the ownership of the recorded performance and the control of the confidentiality of the recorded performance. The system can automatically integrate the background signals and the audio-visual signals and produce a DVD containing the recorded performance. The audio and video system can include a camera rotatable between a first operative position to produce a landscape picture of an individual in the studio; and, a second operative position to produce a portrait picture of an individual in the studio.

In a further additional embodiment of the invention, provided is an improved method to record performances. The method comprises the steps of selecting a plurality of different kinds of performances; for each one of the kinds of performances, selecting and recording for recall at least one associated scenic backdrop; providing at least one studio booth including an audio and video system to detect and generate audio-visual signals representing performances conducted in the studio, including a computer system to generate backdrop signals representing a scenic backdrop, and including a control system to integrate the background signals and the audio-visual signals to make a recorded performance; conducting one of the kinds of performances in the booth; detecting in the booth with the audio and video system the one of the kinds of performances, and generating audio-visual signals representing the one of the kinds of performances; generating in the booth with the computer system backdrop signals representing a scenic backdrop assigned to the one of the kinds of performances; and, integrating with the control system in the booth the audio-visual signals and the backdrop signals to make an integrated performance. The kinds of performances can each be formatted. Each one of the kinds of performances can have a different associated scenic backdrop. Different categories of performances can be listed in a menu at the studio booth; a category of performance can be selected from the menu; and the performance conducted in the booth can be in the category of performance selected from the menu. The scenic backdrop can be selected based on at least one of a pair comprising geographic locale; and, desired content. The integrated performance can be required to be recorded using a pre-selected backdrop. The integrated performance can be entered in a contest. The integrated performance can be transmitted to a personal relationship web site. The integrated performance can be transmitted to a personal relationship web site to register and establish an account at the web site. The integrated performance can be transmitted to apply for employment. The scenic backdrop can be made at a location remote from the studio and stored for recall. The scenic backdrop can be stored at a location remote from the studio for recall. The studio can include a chroma key screen inside said studio to produce background light that is, simultaneously with said performance conduction in said booth in step (d), detected by said audio and visual system. The scenic backdrop can be stored at the studio. The chroma key screen can include a plurality of light reflective glass beads. The screen can be comprised of a material that is green. The method can include the additional steps of creating a network comprised of multiple nodes including a plurality of studio booths at separate remote locations, and including a plurality of receiving apparatus to receive at the nodes recorded performances from the booths; recording a plurality of the kinds of performances at the booths; transmitting each of the kinds of performances from the booths to a plurality of the nodes; and, promoting the product or service by advertising at each of the plurality of nodes. The method can include the additional step of producing at the booth a display indicating the ownership of the integrated performance and the control of the confidentiality of the integrated performance. The method can be performed automatically in the booth and include the additional step of processing automatically the integrated performance to produce and dispense at the booth a DVD of the performance. The audio and video system can include a camera rotatable between a first operative position to produce a landscape picture of an individual in the studio, and a second operative position to produce a portrait picture of an individual in the studio. The camera can, during the method, be rotated from the first operative position to the second operative position.

In a further embodiment of the invention, I provide an improved method to produce in an area of restricted size while minimizing perspective distortion and subject distortion a recording of an individual that produces the illusion that the individual is located in a larger area. The method comprises the step of providing a studio booth. The studio booth includes an interior with a front wall, a rear wall, side walls extending between the front wall and rear wall, a floor, and a ceiling; includes an audio and video system to detect and generate audio-visual signals comprising a recording of at least one performance conducted in the booth, the system including a digital camera mounted at the front wall; includes a chroma key screen extending over at least a portion of the rear wall to produce background light that is, along with the performance conducted in the booth, detected by the digital camera; includes a transmitter to send the audio-visual signals to a selected location remote from the booth; and, includes a computer system to generate backdrop signals representing a scenic backdrop and to integrate the audio-visual signals and the backdrop signals to produce a recorded performance. The booth occupies a spatial volume fitting substantially within a footprint volume having a simple convex polygon cross-section having dimensional parity and having a width no greater than ten feet. The method also includes the steps of selecting a lens system for the digital camera with a horizontal field of view that minimizes subject distortion of an individual performing in the interior of the booth; defining, to minimize subject distortion, a minimum distance that an individual stands away from the camera when the individual is in the interior of the booth to conduct a performance; selecting a scenic backdrop to be utilized by the computer system, to minimize subject-background correlation distortion, and depicting an area larger than the interior of the studio booth; conducting a live performance in the booth by the individual in the interior and no closer to the camera than the minimum distance and generating with the computer system a recording of the performance comprising audio visual signals of the live performance integrated with backdrop signals of the selected scenic backdrop selected in step (d); and, transmitting to the selected remote location with the transmitter the recording produced in step (b). The minimum distance can be three feet, and the horizontal field of view can be in the range of fifty-two degrees to sixty-six degrees. The booth can includes a receiver and advertising display screens; and, the computer system, in addition to transmitting said recording, can receive promotional material for display on the display screen. The digital camera can be a high definition camera producing at least 1080 lines of horizontal resolution; and, the computer system can initially transmit the recording in a resolution less than the 1080 lines of horizontal resolution and then at a later time transmit the recording in a resolution of at least 1080 lines of horizontal resolution. The chroma key screen can extend onto the floor, can extend onto the floor and side walls, or can extend onto the floor, side wall, and ceiling. The scenic backdrop can be pre-selected prior to recordation of a performance in the booth by the individual. The lens system can be a zoom lens system; and, the method can comprises the additional step of defining a zoom position for the zoom lens system. The method can include the additional steps of collecting a fee from the individual; of evaluating at the selected remote location on its merits the live performance in the transmitted recording; of preparing a report of the evaluation; and, of transmitting the report to the individual. The recording generated in the booth can have minimized subject and perspective distortion and consequently realistically make the individual appear to have made the recording in an area larger than the interior of the booth. The greatest side dimension can be greater than ten feet.

In another embodiment of the invention, I provide an improved method to generate bi-directional content by receiving promotional data and by producing in an area of restricted size while minimizing perspective distortion and subject distortion a recording of an individual that produces the illusion that the individual is located in a larger area. The method comprises the step of providing a studio booth. The booth includes an interior with a front wall, a rear wall, side walls extending between said front wall and rear wall, a floor, and a ceiling; includes an exterior; includes an audio and video system to detect and generate audio-visual signals comprising a recording of at least one performance conducted in the booth, the system including a digital camera mounted at the front wall; includes a chroma key screen extending over at least a portion of the rear wall to produce background light that is, along with the performance conducted in the booth, detected by the digital camera; includes at least one display screen on the exterior of the booth; includes a transmitter-receiver to send the audio-visual signals to a selected location remote from the booth and to receive signals containing promotional material; and, includes a computer system to receive the promotional signals from the transmitter-receiver and display the signals on the display screen. The booth occupies a spatial volume fitting substantially within a footprint volume having a simple convex polygon cross-section having dimensional parity and having a width no greater than ten feet. The method also includes the steps of selecting a lens system for the digital camera with a horizontal field of view that minimizes subject distortion of an individual performing in the interior of the booth; of defining, to minimize subject distortion, a minimum distance that an individual stands away from the camera when the individual is in the interior of the booth to conduct a performance; of selecting a scenic backdrop to minimize subject-background correlation distortion, and to depict an area larger than the interior of the studio booth; of conducting a live performance in the booth by the individual in the interior and no closer to the camera than the minimum distance and generating with the audio and visual system a recording of the live performance with the scenic backdrop selected in step (d); of transmitting to the selected remote location with the transmitter-receiver the recording produced; and, of transmitting to said transmitter-receiver signals containing promotional material; and, of displaying on the display screen with the computer system the promotional material.

In still a further embodiment of the invention, I provide an improved method to produce in an area of restricted size in a realistic manner while minimizing perspective distortion and subject distortion a recording of an individual that produces the illusion that the individual is located in a larger area. The method includes the step of providing a studio booth including an interior with a front wall, a rear wall, side walls extending between the front wall and rear wall, a floor, and a ceiling; including an audio and video system to detect and generate high resolution audio-visual signals comprising a recording of at least one performance conducted in the booth, the system including a high resolution digital camera mounted at the front wall; including a transmitter to send the audio-visual signals to a selected location remote from the booth; and, includes a computer system to receive high resolution audio-visual signals and to generate low resolution audio-video signals from said high resolution audio-visual signals. The booth occupies a spatial volume fitting substantially within a footprint volume having a simple convex polygon cross-section having dimensional parity. The method includes the steps of selecting a lens system for the digital camera with a horizontal field of view that minimizes subject distortion of an individual performing in the interior of said booth; of defining, to minimize subject distortion, a minimum distance that an individual stands away from the camera when the individual is in the interior of the booth to conduct a performance; of selecting a scenic backdrop to minimize subject-background correlation distortion, and depicting an area larger than the interior of the studio booth; of conducting a live performance in the booth by the individual in the interior and no closer to the camera than the minimum distance and generating with the audio and visual system a recording of the performance comprising high resolution audio visual signals of the live performance including the selected scenic backdrop; of generating with the computer system low resolution audio visual signalsfrom the high resolution audio visual signals; of transmitting with the transmitter at a selected time the low resolution audio visual signals to a selected location; and, of transmitting with the transmitter subsequent to the selected time the high resolution audio visual signals to a selected location.

In still another embodiment of the invention, I provide an improved method to conduct a contest by producing in an area of restricted size in a realistic manner while minimizing perspective distortion and subject distortion a recordings of an individual that produce the illusion that the individual is located in a larger area. The method includes the step of providing at least one studio booth. The booth includes an interior with a front wall, a rear wall, side walls extending between the front wall and rear wall, a floor, and a ceiling; including an audio and video system to detect and generate high resolution audio-visual signals comprising a recording of at least one performance conducted in the booth, the system including a high resolution digital camera mounted at the front wall; including a transmitter to send the audio-visual signals to a selected location remote from the booth; and, includes a computer system to receive high resolution audio-visual signals and to generate low resolution audio-video signals from said high resolution audio-visual signals. The booth has a footprint fitting within a rectangular area having a greatest side dimension of ten feet. The method also includes the steps of selecting a lens system for the digital camera with a horizontal field of view that minimizes subject distortion of an individual performing in the interior of the booth; of defining, to minimize subject distortion, a minimum distance that an individual stands away from the camera when the individual is in the interior of the booth to conduct a performance; of selecting a contest and defining contest rules; of pre-selecting at least one scenic backdrop that must be utilized by contest participants, that is utilized by said computer system, that minimizes subject-background correlation distortion, and that depicts an area larger than the interior of the studio booth; of conducting for use in the contest live performances in the booth by individuals in the interior and no closer to the camera than the minimum distance and generating with the computer system a recording of the performance comprising audio visual signals of the live performance integrated with backdrop signals of the selected scenic backdrop; and, of transmitting to the selected remote location with the transmitter the recording that is produced.

In yet a further embodiment of the invention, I provide an improved method to conduct a broadcast interview by producing in an area of restricted size in a realistic manner while minimizing perspective distortion and subject distortion a recording of an individual that produces the illusion that the individual is located in a larger area. The method includes the step of providing a studio booth. The booth includes an interior with a front wall, a rear wall, side walls extending between the front wall and rear wall, a floor, and a ceiling; including an audio and video system to detect and generate high resolution audio-visual signals comprising a recording of at least one performance conducted in the booth, the system including a high resolution digital camera mounted at the front wall; including a transmitter to send the audio-visual signals to a selected location remote from the booth; and, includes a computer system to receive high resolution audio-visual signals and to generate low resolution audio-video signals from said high resolution audio-visual signals. The booth has a footprint fitting within a rectangular area having a greatest side dimension of ten feet. The method also includes the steps of selecting a lens system for the digital camera with a horizontal field of view that minimizes subject distortion of an individual performing in the interior of the booth; of defining, to minimize subject distortion, a minimum distance that an individual stands away from the camera when the individual is in the interior of the booth to conduct a performance; of selecting a scenic backdrop to minimize subject-background correlation distortion, and to depict an area other than the interior of the studio booth; of conducting and recording a live interview of the individual in the interior of the booth and no closer to the camera than the minimum distance and generating with the computer system a recording of the performance comprising audio visual signals of the live interview integrated with backdrop signals of the selected scenic backdrop selected in step (d), the live interview conducted by another individual at a location remote from the booth; and, transmitting to a selected remote location with the transmitter the recording that is produced.

Turning now the drawings, which depict the presently preferred embodiments of the invention for the purpose of illustration thereof, and not by way of limitation of the invention, and in which like characters refer to corresponding elements throughout the several views, FIGS. 1 to 4 illustrate a studio booth 10 constructed in accordance with the invention for producing audio-visual recordings of performances and for producing still photographs, for producing DVDs containing recorded performances, and for transmitting, by wireless or other signals, recorded performances to Internet web sites, to e-mail addresses, or to other desired locations. Booth 10 can be utilized at any desired location, but in a preferred embodiment of the invention is located in a shopping center, airport, college campus, or other public location. Further, it is anticipated that a plurality of booths 10 will be utilized at spaced apart, different geographic locations to facilitate the use by many people of booths 10. For example, a plurality of individuals in a designated area (for example, a suburb or other part of a city, a city, a county, a state, a country, etc.) can submit recorded performances from different booths as part of a contest, of a group of applications for a job, etc. Booth 10 is, as is the custom with recording studios, preferably sound proof, or at least substantially sound proof.

The exterior of booth 10 includes a pair of registration stations that enables two individuals to simultaneously register to utilize booth 10. The first registration station include a touch sensitive registration screen 13, a bill reader 14 for reading and accepting currency, a credit card reader 15 for reading and utilizing an individual's credit card to make a payment, a money changer 16, and a printer 82. The second registration station is identical to the first registration station and includes a touch sensitive registration screen 13A, a bill reader 14A, a credit card reader 15A, a money changer 16, and a printer 82A. Handicap rated ramp 13 leads to door 17. Door 17 is opened to access the interior of booth 10.

Traveling banner 46 on the exterior of booth 10 allows various messages and/or advertisements to scroll across banner 46. The right side 40 of booth 10 includes a television screen or other display screen 12, and includes a display unit 11 that projects three dimensional digital video images 47 out into space and detached from booth 10, producing an independent floating, moving image featuring high definition and crisp visibility from distances up to one hundred feet and up to sixty degree viewing angles. One such unit is produced by Provision of 9253 Eton Avenue, Chatsworth, Calif. 91311. The left side 41 of booth 10 similarly includes a television screen or other display screen 12A, and includes a display unit 11A that projects three dimensional digital video images out into space and detached from booth 10, producing an independent floating, moving image featuring high definition and crisp visibility from distances up to one hundred feet and up to sixty degree viewing angles.

The rear 42 of booth 10 includes a plurality of television or other display screens 43, 44.

If an individual is in booth 10, sign 19 adjacent door 14 reads "IN SESSION" to notify onlookers that the booth 10 is in use. If booth 10 is empty, sign 19 reads "NOT IN SESSION" or "OPEN" or "READY TO RECORD". Door 14 can be locked and unlocked by an individual inside booth 10. When an individual is inside booth 10, an individual outside booth 10 can not unlock door 14.

Figure 5:
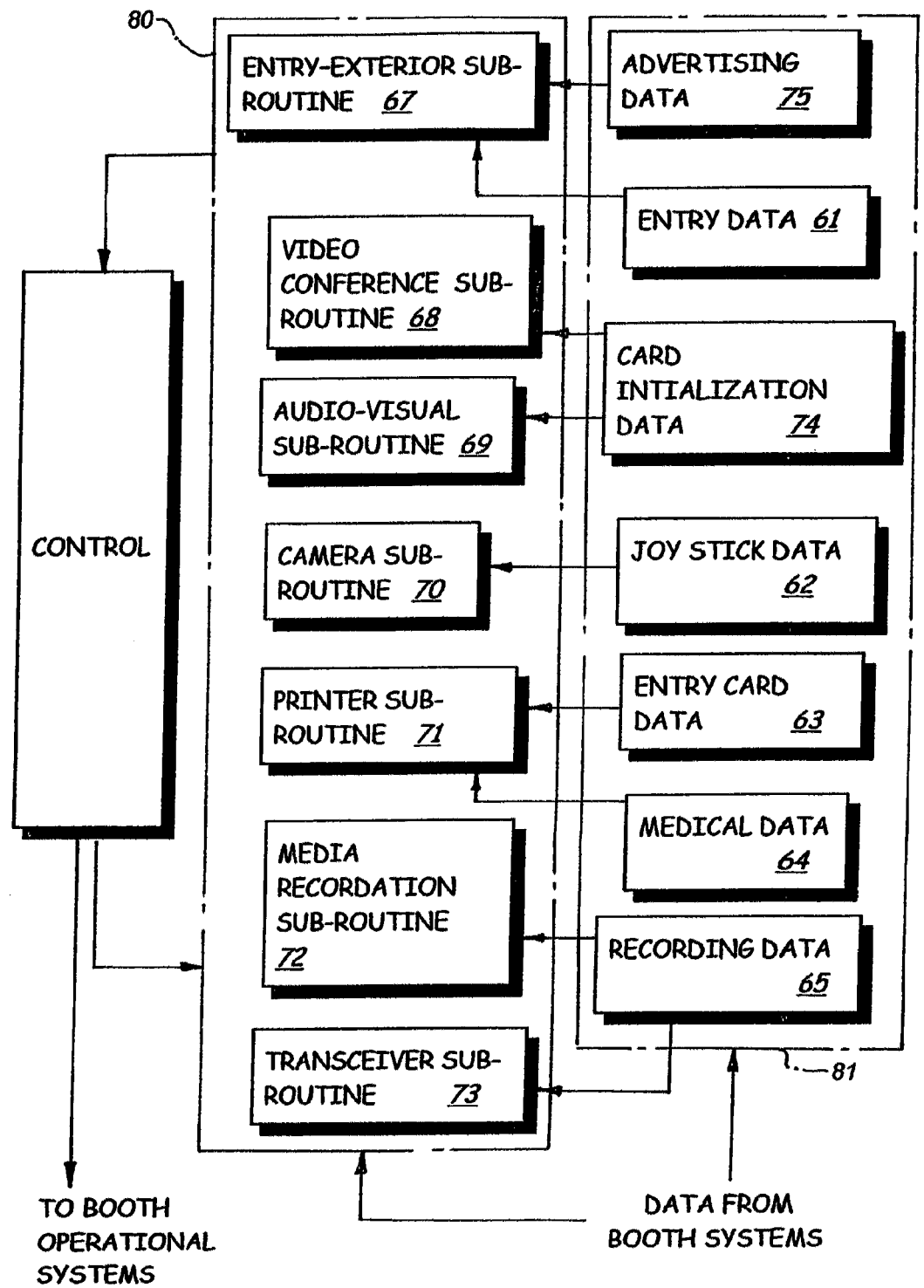
FIG. 5 is a block diagram illustrating a control system that can be utilized in the studio booth of FIG. 1.

The computer control system illustrated in FIG. 5 can be utilized in booth 10 to control the operation of booth 10 and includes various sub-routines 80 and various data stored in memory 81.

Entry-exterior sub-routine 67 determines the information displayed on and generates signals for screens 12, 12A, 43, 44, traveling banner 46, and 3D projection units 11 and 11A. Sub-routine 67 utilizes advertising data 75 stored in memory 69. Sub-routine 67 also controls the registration stations, including registration screens 13 and 13A and the payment system.

When an individual in booth 10 is conducting a video conference with another individual at a location remote from booth 10, video conference sub-routine 68 controls the receipt and transmission of video and audio information to and from booth 10.

During a performance by an individual in booth 10, audio-visual sub-routine 69 controls the recordation in computer memory (as recording data 65) of digital audio and video data defining the performance. Camera 21 records and transmits to computer memory 81 a video record of the performance as part of recording data 65. The audio record of the performance is transmitted by microphone(s) 23 to computer memory as part of recording data 65. An analog system can be utilized to record a performance, but a digital system is presently preferred in the practice of the invention. Recording data 65 can also include data that categorizes or differentiates performances from other performances. For example, if an individual records a performance for the purpose of entering an Interscope Records singing or talent contest, the individual selects this category(s) while registering at booth 10, and this category information is stored in data 65 along with the individual's recorded performance. When the individual's recorded performance is transmitted by transceiver 20 using transceiver sub-routine 73, the category information, along with any other desired information like demographic information provided by the individual, is transmitted along with the individual's performance. The computer system in booth 10 can be configured such that a recorded performance stored in recording data 65 can, if desired, be accessed and viewed by a computer that is at a remote location; or, such that the remote computer can cause the recorded performance to be transmitted from booth 10 to the remote computer or to another desired location at which a reviewing entity is seeking any or selected information concerning the performance. The reviewing entity(s) can seek information comprising demographic information, can seek the names of individuals participating in a contest or job application, can seek information comprising the actual performances of individuals participating in a contest or job application, can seek any other desired information associated with the recorded performance, can rate the performance, can selected the winner(s) of a contest, etc. The reviewing entities can comprise members of the public that are rating a performance or selecting the winner in a group of performances. The remote computer can be operated by the owner of booth 10 or by any other desired party.

Recorded performances can be differentiated by the computer system in booth 10 according to any desired subject matter or classification system such as, by way of example, gender of the performer, age of the performer, a category Gob application for a particular company, musical performance for a particular contest, message to a particular person, etc.), the kind of performance (singing, modeling, acting, interview, etc.), and so on. A category of performances can, if desired, be further differentiated into sub-categories. If, for example, a category is Contests, the Contests category can include sub-categories identifying a singing contest, modeling contest, etc.

After a recorded performance is transmitted from booth 10 (either concurrently with the performance or at some time after the performance) to a selected site, the site can be accessible to any desired individual seeking information comprising the recorded performance or comprising demographic or other information associated with and accompanying the performance.

Sub-routine 69 also enables an individual utilizing booth 10 to play back and preview his or her performance using a display screen 24, 25 and audio speaker in booth 10.

During use of the booth 10 by an individual, camera sub-routine 70 controls operation of the camera and, in response to use of a joy stick by an individual in the booth, controls movement of the camera up and down, controls adjustment of the camera focus or zoom lens, etc.

The printer sub-routine 71 controls printers 82 and 82A and, when a printer is utilized inside booth 10, controls that printer. Printers 82 and 82A print and dispense activation cards, credit card receipts, and any other desired information. A printer installed inside booth 10 can be utilized to print a drug prescription or any other desired information.

The media recordation sub-routine controls the recording on a DVD or other media of an individual's or group's performance and controls the dispensing of the DVD to an individual in, or outside, the booth 10.

The transceiver sub-routine 73 controls the wireless or other transmission of data to and from booth 10, including the receipt of advertising information to be displayed on screens 12, 12A, 43, 44, on traveling banner 46, and by 3D projection units 11 and 11A, and, including the transmission of recorded performances to Internet web sites, e-mail addresses, and other desired locations. When a recorded performance is transmitted to a website or other location, the performance can be incorporated in a particular selected category at the website. For example, if the performance is submitted as part of a singing contest, the performance can be incorporated with other entries as part of the contest and can be made accessible by the individual that recorded the performance, by members of the public or other individuals that wish to view and/or evaluate and rate the performance, by a company that is looking for and evaluating talent, or by any other entity seeking information about the individual or the contest in which the individual is participating.

Figure 6:
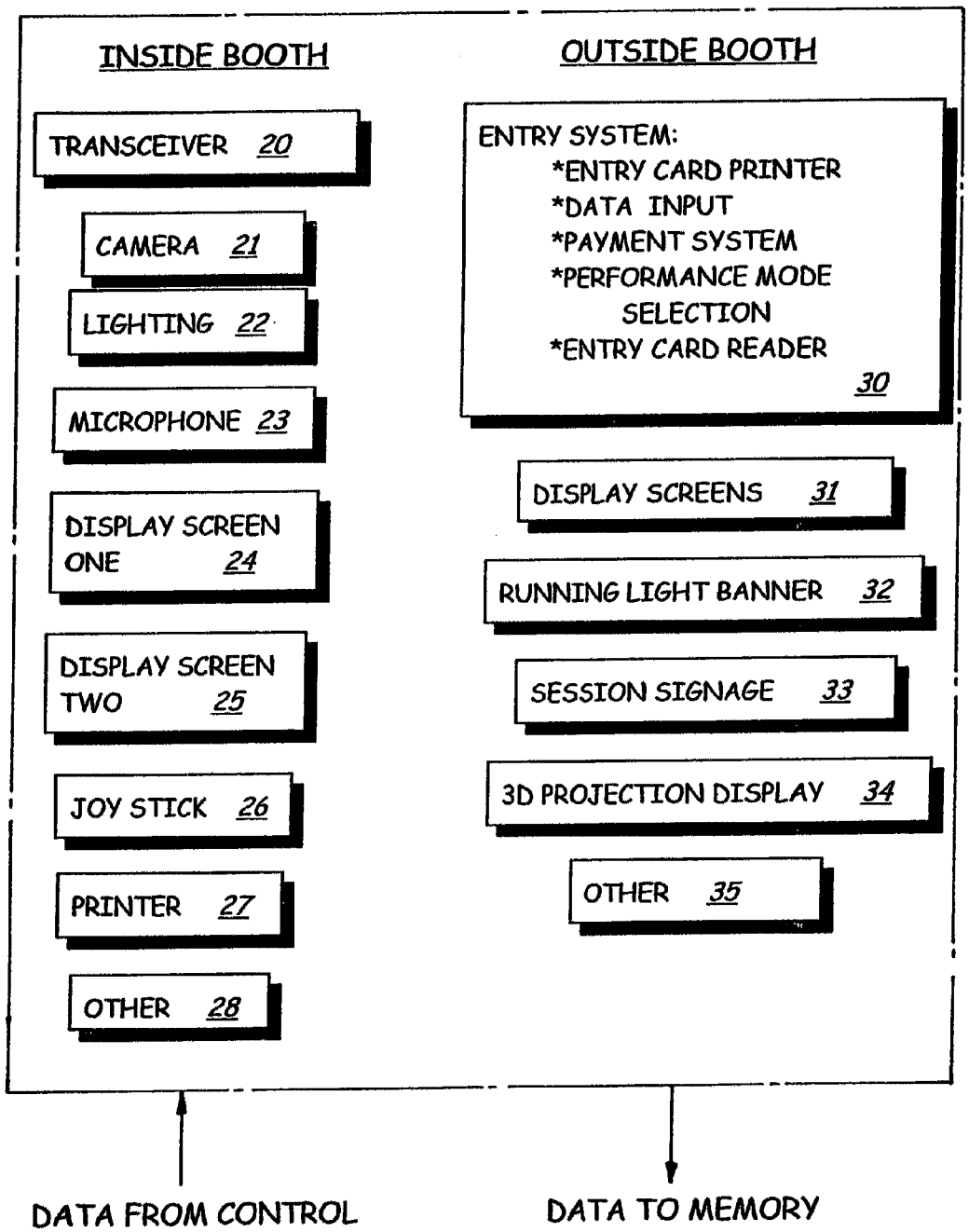
FIG. 6 is a block diagram illustrating equipment utilized on the interior and exterior of the studio booth of FIG. 1.

Equipment that can be incorporated in booth 10 is illustrated in FIG. 6. Equipment utilized by an individual inside booth 10 includes transceiver 20, camera 21, lighting 22, microphone 23, display screen one 24, display screen two 25, joy stick 26, printer 27, and activation card slot 28. Apparatus for producing and dispensing a DVD or other media recordation of an individual's performance can also be included in booth 10.

Equipment utilized by an individual outside booth 10 includes entry system 30, display screens 31, running light banner 32, session signage 33, 3D projection display 34, and other desired equipment 35. Entry system 30 includes entry card printers 82 and 82A; data input touch sensitive registration screens 13 and 13A; payment systems 14, 15, 16, 14A, 15A, 16A; and, performance mode selection (utilized during operation of registration screens 13 and 13A).

Special features that are preferably, but not necessarily, incorporated in booth 10 pertain to (1) equivalent recording conditions, (2) registration, (3) access, (4) camera control, (5) activation card, (6) portal access, and (7) prescription dispensation. These features are discussed below.

Equivalent Recording Conditions

The quality of recording equipment can vary widely, as can how the equipment is utilized. Computers can be used to alter the appearance of an individual, the individual's voice, the background scene in a recording, etc. An individual who is a mediocre singer can be made by an expert sound/recording engineer to sound impressive.

An important feature of the invention is to insure that equivalent recording conditions exist in each studio booth or location utilized, and that an individual's performance is accurately, albeit professionally, recorded without significant touching up that alters the true nature of and misrepresents the individual's performance. For example:

(1) Lighting. Light fixtures of equivalent quality are utilized in each studio booth or other location. The fixtures in one booth produce light having wavelengths equivalent to fixtures in another booth. The placement and intensity of light fixtures in one studio booth replicates or reproduces the light found in another studio booth.

(2) Camera. Cameras of equivalent quality are utilized in each studio booth or other location.

(3) Microphones. Microphones of equivalent quality and sensitivity are utilized in each booth.

(4) Recording equipment. The equipment utilized to record signals generated by cameras and microphones is of equivalent quality in each studio booth or location.

(5) Background music. Even though a song an individual is singing during a recorded performance may vary, the quality of the background music is relatively consistent, and the volume of the background music with respect to the volume of the performer's voice is the same in each studio booth or other location. The volume of a performer's voice and/or background music may, if desired, be adjusted so that the volumes are substantially equivalent, but if this is done it is done in an equivalent manner in each booth. Such a volume adjustment may be used if the performer's voice is softer or is louder than the background or accompaniment music; however, other modifications of a recorded performance are not currently planned because it is desired to keep the recording of reach performance as accurate as possible. If other modifications are selected they are carried out in an equivalent manner in each booth.

(6) Background scene or "set". If there is a background provided behind the performer—for example, a picture of the skyline of New York city—the background in each studio booth is equivalent or of equivalent quality.

Replicating in each booth equivalent recording conditions and avoiding or minimizing modifications of the recorded performance tends to give a fair representation of each performer.

Registration

Since each studio booth is sized to be utilized by only one or a few individuals at a time to record a performance, lines can form and waiting times can ensue before an individual can access a studio booth to make a recording. The studio booth of the invention addresses this problem by preferably, although not necessarily, providing each booth with a plurality of registration stations so that two or more individuals can simultaneously register to utilize the booth. In addition, when an individual registers he is provided with an estimated time when the booth will be available. This time is printed on an activation, or entry, card that is printed and provided to a customer when the customer registers. Further, when each individual enters and activates a booth with his or her activation card (described below), an individual has a set time to record a performance and leave the booth. By way of example, and not limitation, once an individual activates a booth, the individual is given thirty seconds to prepare for a recording, is given three minutes to make the recording, and is given an additional thirty seconds to complete the session and exit the booth. As the last thirty seconds of time expires, the lights in the booth fade, encouraging the user to exit the booth.

Access

When an individual is in a studio booth making a recording, signage on the exterior of the booth will light and state "STUDIO IN USE", "RECORDING IN PROCESS", "IN USE", etc. This signage will deter individuals from entering the booth while another individual is recording a performance. The signage will not, however, stop everyone. Curious onlookers will be tempted to open the door to the booth to "take a peek" and can ruin a performance by opening the door. Importantly, to prevent such an occurrence, the access door on the booth automatically locks when the booth is activated with an activation card and can only be opened by the individual(s) in the booth. Alternatively, the door can be provided with a lock that is only operable from inside the booth so that an individual can lock and unlock the door once the individual is inside the booth.

Camera Control

Figure 15:
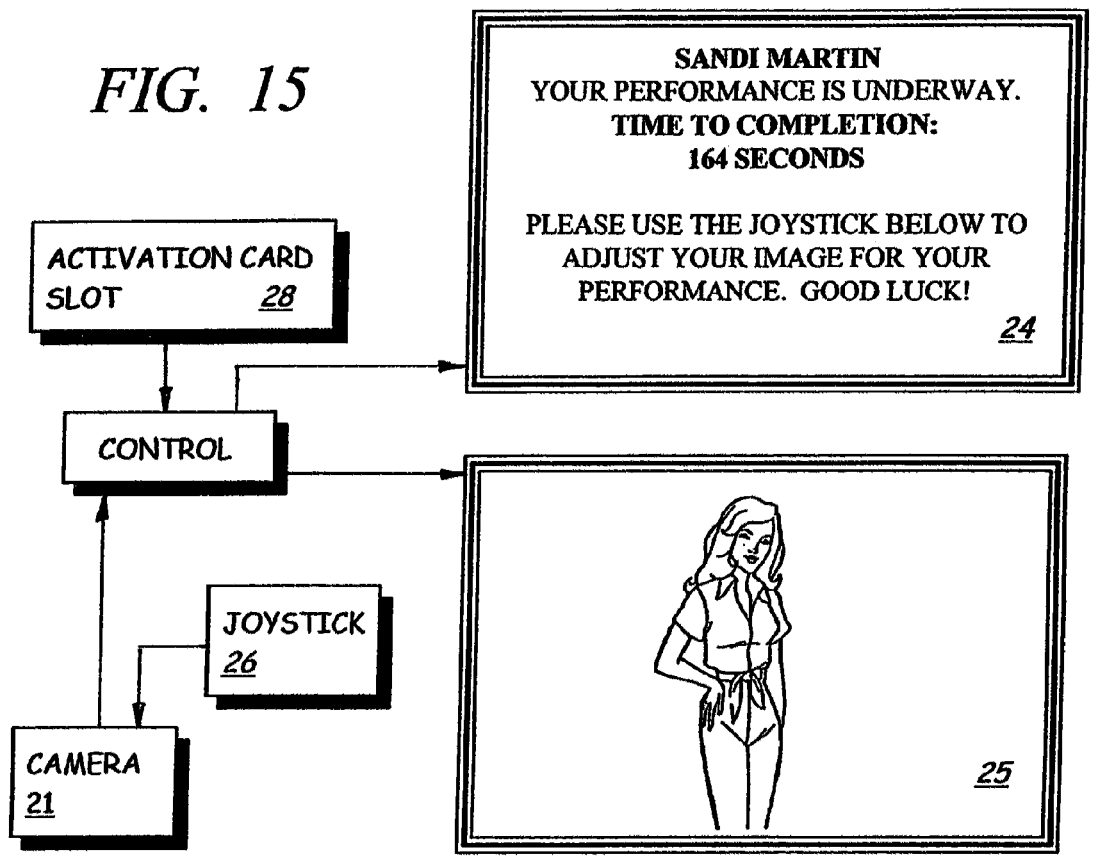
FIG. 15 is a diagram illustrating the operative relationship between a pair of display screens inside the studio booth, the activation card, the control, the joystick, and the camera.
Figure 16:
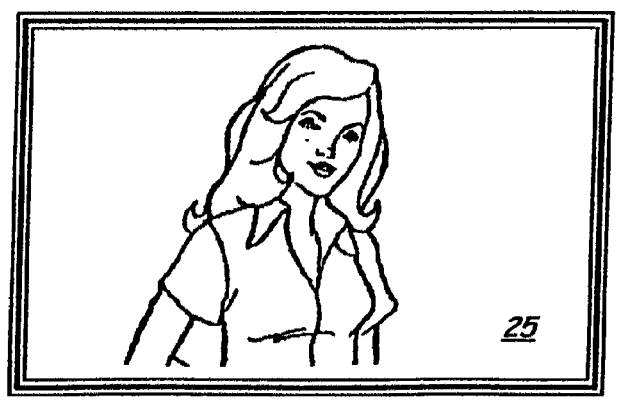
FIG. 16 is a front view of a display screen inside the studio booth illustrating the zoom feature of the camera in the video booth.

The camera(s) in the studio booth can remain in a single stationary position, as is the case in other prior art recording booths. To enhance, however, the flexibility of the booth, it is preferred that the camera be adjustable in at least two of (1) up and down along a vertical axis, (2) rotationally about a vertical axis, (3) back and forth along a first horizontal axis parallel to the ground and generally normal to an individual in the booth, (4) rotationally about the first horizontal axis, (5) back and forth along a second horizontal axis normal to the first horizontal axis, (6) rotationally about the second horizontal axis, (7) back and forth along, or, rotationally about another selected axis, (8) focus or zoom, and (9) aperture setting. The camera utilized in the presently preferred embodiment of the invention is adjustable up and down along a vertical axis and the focus of the camera is adjustable. A joy stick is utilized. Moving the joy stick toward and away from an individual in the booth adjusts the camera up and down along the vertical axis. Moving the joy stick from side-to-side adjusts the focus or zoom of the camera. In FIG. 15, the camera is adjusted such that most of the individual in the booth is viewed by the camera 21 and is shown on display screen 25 and is, consequently, being recorded. In FIG. 16, the camera is adjusted such that is has zoomed in on and enlarged a portion of the individual shown in FIG. 15. Consequently, it is the enlarged portion that is being recorded. Having the ability to zoom in on a portion of an individual is important in the practice of the invention because it facilitates certain performances like, for example, modeling when a model may want a close-up of her face and another shot which shows her from head to toe. The zoom feature is also useful when an individual is conducting a video conference with a physician and the physician wishes to see, for example, a certain area on the individual's body.

Activation Card

An important feature of the invention is that the system utilized to provide an individual both with means to enter and activate a studio booth and with contest rules and disclaimers.

Figure 9:
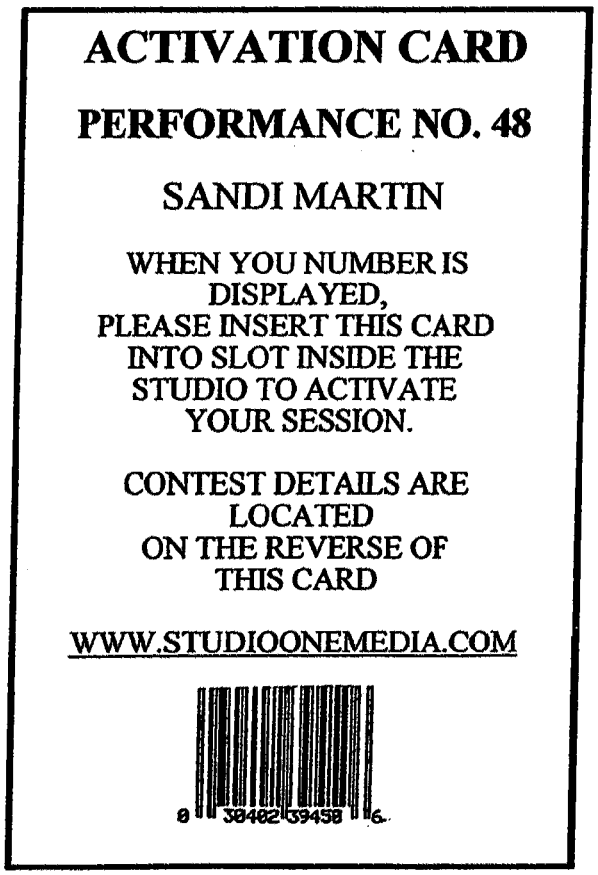
FIG. 9 is a top view illustrating an activation card printed for an individual who has paid to utilize the studio booth to record a performance.

Once an individual registers and pays for right to enter the studio booth and record a performance, a printer in the studio booth prints and dispenses an activation card of the general type illustrated in FIG. 9. The activation card prints the name of the individual (Sandi Martin), the session or performance number (48) assigned to the individual, and informs the individual how the card is used to activate the individual's recording session once the individual enters the studio booth (i.e., insert the card into the slot inside the studio). The bar code or other activation code printed or formed on or in the activation card is read by the studio booth when the individual is in the booth and, as is described below, activate the booth for the individual's recording session. The reverse side of the activation card, illustrated in FIG. 10, sets forth the contest details, including the deadline (Jul. 31, 2000) for entering the contest, the fact that there will be a winner, where the winner's name can be found, the prize(s) awarded the winner ($25,000.00 and an all expense paid trip), a guideline as to how the individual's recording will be evaluated (performance reviewed for at least one minute), and a legal stipulation(s) or condition(s) associated with the contest. The guideline in FIG. 10 includes a contractual provision that notes that Interscope Records will own the individual's performance. This provision can, if desired, be expanded to commit the individual to a exclusive agency contract with the operator of booth 10 or with any other desired individual or entity. The exclusive agency contract can have any desired terms, including, for example, the length of time the contract is in force, financial terms, etc.

An exclusive agency or other contract can be entered into by an individual at some time after the individual records a performance in a booth 10. This typically would be the case after an individual is named a winner in a talent contest, modeling contest, singing contest, job application, etc.

The following example is given by way of illustration, and not limitation, of the invention.

Example

A studio booth 10 is placed in a shopping center, airport, university campus or other public or non-public location. At 12:00 noon, an individual sees booth 10 and is initially attracted by the 3D projection 47 that is moving and appears to be suspended in space above the ground. The subject matter of projections 47 varies. At one instant, the projection 47 is of a food or other item that many individuals buy or use or like, for example a Coca-Cola bottle, an ice cream cone, a DVD of a popular movie, a likeness of a famous movie star, etc. In another instant, the projection 47 consists of an advertisement like "Buy Coca-cola" or "Fly American Airlines". In another instant, the projection 47 describes the booth: "Studio One Recording". The individual is attracted by the sight of an object apparently floating in space; is attracted by the potential desirability of the object itself; and, is attracted by the continuing alteration of what is being projected by display 34: first a desirable object is displayed, then an advertisement, then a description of the booth itself.

The individual approaches the registration station on the right of door 17 and sees on touch screen 13 the "WLECOME" information shown in the top illustration of screen 13 depicted in FIG. 11. Three illustrations of screen 13 are depicted in FIG. 11. The individual reads the "WELCOME" information and presses her finger against screen 13 over the "PRESS TO START" box. The "CHOOSE A SESSION" information shown in the middle illustration of screen 13 in FIG. 11 appears. The individual presses her finger against the screen 13 over the box to the left of "Record a performance; enter a contest" and then presses her finger against screen 13 over the "CONTINUE" box. The "CONTESTS FOR JULY" information shown in the lower, or third, illustration of screen 13 in FIG. 11 appears. The individual presses her finger against screen 13 over the box to the left of "Music: Interscope Records". The "CONTEST INFORMATION" shown in the top illustration of screen 13 in FIG. 12 appears. The individual reads the information, and presses her finger against the screen 13 over the "CONTINUE" box. The "CONTEST RULES" information shown in the middle illustration of screen 13 in FIG. 12 appears. The individual reads the contest rules, and presses her finger against the screen 13 over the "CONTINUE" box. The "OPTIONAL INFORMATION" shown in the lower, or third, illustration of screen 13 in FIG. 12 appears. The individual enters her name, Sandi Martin; enters her e-mail address sandimartin@cox.net; and enters the email address of Interscope Records, interscope@cox.net. Sandi then presses her finger against screen 13 over the "CONTINUE" box. The information shown in the top illustration of screen 13 in FIG. 13 appears. Sandi presses her finger against screen 13 over the box to the left of the "Yes" to answer the first question (Sandi is seventeen years old); and, presses her finger against screen 13 over the box to the left of the "Yes" to answer to the second question. She then presses her finger against screen 13 over the "CONTINUE" box. The "CHOOSE A SONG" information shown in the middle illustration of screen 13 in FIG. 13 appears. Sandi utilizes a keyboard that is positioned below screen 13 to enter "CLIMB EVERY MOUNTAIN". She then depresses screen 13 over the "CONTINUE" box. The "WOULD YOU LIKE . . . " information shown in the bottom, or third, illustration of screen 13 in FIG. 13 appears. She depresses screen 13 over the box to the left of "Yes" on the screen 13, and then depresses screen 13 over the "CONTINUE" box. The information shown in the top illustration of screen 13 in FIG. 14 appears. Sandi inserts her credit card in credit card reader 15. Her credit card information is transmitted via transceiver 20 (FIG. 6) to a remote location where the credit card charge is approved. The approval is transmitted back to booth 10 via transceiver 20 and printer 82 prints and dispenses a receipt. Sandi takes the receipt. The printer 82 then prints and dispenses the activation card illustrated in FIGS. 9 and 10. When the activation card is dispensed, the "WELCOME" information shown in the bottom illustration of screen 13 in FIG. 14 appears. Sandi reads the card and notes that her performance number is 48; notes that she must insert the card in a slot inside the booth to activate her session; notes the bar code; and notes the contest details and disclaimers on the back of the activation card. The information shown in the bottom illustration of screen 13 in FIG. 14 appears. Sandi notes that the estimated time the booth will be ready for her session is 2:30 p.m. See looks up at screen 33. Displayed on screen 33 is "IN SESSION. NO. 35".

Figure 8:
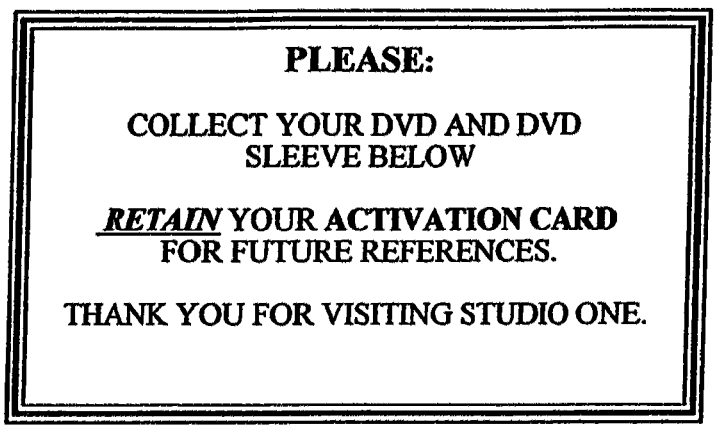
FIG. 8 is a diagram illustrating another communication to an individual inside the studio booth after the individual has activated the booth by inserting an activation card.

Sandi leaves the booth 10 and returns at 2:25 p.m. Displayed on screen 33 is "IN SESSION. No. 47". After five minutes, an individual leaves the booth. Sandi enters and locks door 17 from inside the booth. She notes that there are two display screens 24, 25 inside the booth. Screen 24 displays the information shown in the top illustration of screen 24 in FIG. 7. She inserts her activation card in the slot inside booth 10. The information shown in the middle illustration of screen 24 in FIG. 7 appears. The visual display of time shown on screen 24 begins to count down: 30 29 28 27 26 25 . . . . Her image appears on screen 25 as shown in FIG. 15. Sandi utilizes joystick 26 (FIG. 15) to adjust the height and focus (zoom) of the camera 21 such that her image on screen 25 is that depicted in FIG. 16. After the countdown on screen 24 (as illustrated in the middle illustration of FIG. 7) reaches zero, the information shown on screen 24 in FIG. 15 appears and the visual display of time on screen 24 begins to count down: 180, 179, 178, 177 . . . . The lyrics of the song she has chosen, although not visible in FIG. 15, appear on screen 25 to the right of her image. After the time count down on screen 24 reaches zero, the "YOUR PERFORMANCE IS COMPLETE" information shown in the bottom illustration of screen 24 in FIG. 7 appears. Sandi answers each question "Yes" by pressing screen 24 over the appropriate box. The "PLEASE . . . " information on the screen 24 illustrated in FIG. 8 then appears. A DVD with her recorded performance is ejected from a DVD recorder slot in booth 10. The DVD recorder dispensing slot can also be located on the outside of booth 10 so that Sandi must exit the booth to collect the DVD. Sandi takes the DVD. She notes that she is to retain the activation card. She leaves the booth.

If, when Sandi was viewing the menu on the screen 13 that is at the bottom of FIG. 11, she had selected modeling, she would have been given, on a succeeding menu appearing on screen 13, the option of a still photo(s) or a video. Similarly, if, when Sandi was viewing the menu on the screen 13 that is in the middle of FIG. 11, she had selected "Have your photo taken", the booth 10 would have taken a still photo(s) of her. In other words, camera 21 can be utilized to produce still photos or video of a performer(s). The video normally would, but not necessarily, include speaking or singing by the performer.

After Sandi has completed recording her performance and has left the booth, the computer control automatically forwards her performance and all demographic or other data associated with the performance to her e-mail address sandimartin@cox.net and to Interscope Records at interscope@cox.net. Interscope Records posts her performance on their web site to be accessed by Sandi and by members of the public. Members of the public have the opportunity of rating Sandi's performance on a scale of one to ten, with ten being the best and one being the worst. Interscope also has at least one its employees or independent contractors rate Sandi's performance on a scale of one to ten (one being the worst and ten being the best) for each of the following criteria:

A. Range of voice.
   B. Staying on key.
   C. Tempo: is the song sung with an acceptable tempo, or is it too fast or too slow.
   D. Tempo variation: is the tempo of the song varied to make listening to the song more interesting.
   E. Mannerisms while singing: i.e., do mannerisms add or detract.
   F. Distinctiveness of voice.
   G. Purity, melodic sound of voice.
   H. Projection of voice.
   I. Enunciation: is the song understandable.
   J. Appearance of singer's face: does audience want to look at and watch the singer.

Interscope also has at least one of its employees or independent contractors act as a contest judge and compare Sandi's performance to the performances of other individuals that have recorded a performance in a booth 10 and entered Interscope's contest. The contest judge picks $1^{st}$, $2^{nd}$, and $3^{rd}$ place winners in the contest. The judge(s) is free to utilize any criteria the judge wishes to pick a winner. Or, alternatively, Interscope suggests or requires the judge to utilize certain criteria in selecting a contest winner. Interscope notifies the winners by e-mail and on its web site. Sandi is the 1$^{st}$ place winner. She is awarded $25,000.00 and an all expense paid trip to California to audition live for Interscope. She auditions for Interscope in California. As a result, Interscope offers her a $1,000,000.00 one year exclusive recording contract. She accepts and signs the contract.

In another embodiment of the invention, the performances used during a contest are not conducted in booths located in public venues or traffic areas, but are conducted in a plurality of booths or studios located inside buildings, in non-public areas, or in areas where there is little or no public foot traffic. Such non-public recording studios still preferably utilize a uniform, consistent set of recording variables, an activation card, and other components of the invention.

When an individual utilizes a booth 10, the charge for utilizing the booth can vary as desired. It is, however, presently preferred that the cost be nominal to encourage a high volume use of booths 10. A presently preferred charge for a 3 minute recording session is $20.00.

The Studio Booth as an Access Portal

Figure 18:
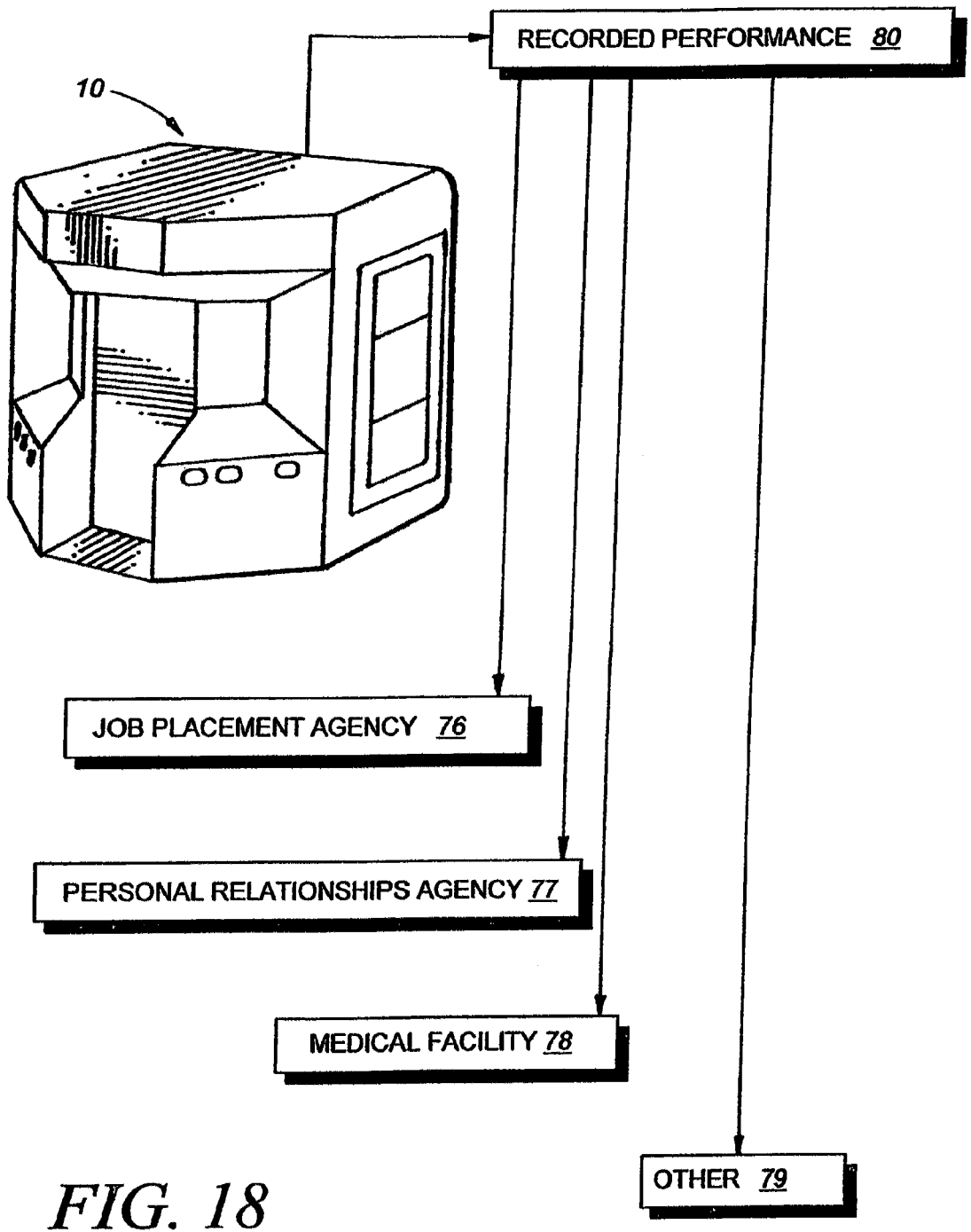
FIG. 18 is a diagram illustrating the use of a studio booth of the invention as an access portal to a web site used to establish a personal relationship between parties.

In a further embodiment of the invention, the studio booths of the invention are utilized by individuals as portals to access a personal relationship service like a dating or match-making service, to access an employment agency, to access a medical facility like a hospital or physician's office, or to access another desired service or organization. As is illustrated in FIG. 18, an individual first utilizes a studio booth 10 to produced a recorded performance 80. By way of example and not limitation, the performance can comprise the individual giving answers during an interview, comprise a speech by the individual describing the individual's characteristics, comprise the individual singing a song, comprise the individual modeling, or comprise the individual sitting for a still photograph. Such a recording is accomplished utilizing (1) the camera sub-routine 70 and audio-visual sub-routine 69 (FIG. 5) to control the position and focus of the camera (and possibly the microphones and lighting) and to generate signals and recording data 65 defining the recording. The recording is then transmitted by booth 10 to a job placement agency 76, to a personal relationships agency 77, to a medical facility, or to another desired location 79. Other required data or information typically is transmitted along with the recorded performance 80. Such data can vary as desired but can, by way of example, include the individual's name, address, age, phone number, vocational interests, e-mail address, resume, likes and dislikes and hobbies or other areas of interest, personality profile, likes and dislikes with respect to the personality and interests of other individuals, etc. The job placement agency 76, personal relationships agency 77 or medical facility 78 then contacts the individual, or vice-versa, to exchange additional information about the services provided, the charges of the dating service, or about the individual.

The use of the booth of the invention as an access portal appears to be a particularly advantageous way of enticing an individual to access a personal relationships service comprising a dating or match making service. Alternatively, after an individual has made an initial contact with a job placement agency 76, personal relationships agency 77, medical facility 78, or other organization 79, the individual can subsequently produce in booth 10 a recorded performance 80 and have the booth 10 transmit the performance to the agency 76 or 77, medical facility 78, etc.

When booth 10 is utilized as an access portal to a dating or match making service, one particular advantage of booth 10 is that it produces an accurate photographic record of the individual in the booth and, as a result, functions as an independent verification of the appearance of the individual. This is important because one primary problem encountered by dating or match-making services is that pictures submitted by potential clients often do not fairly represent the actual appearance of the individual.

The Studio Booth as Prescription Dispensation Station

Figure 17:
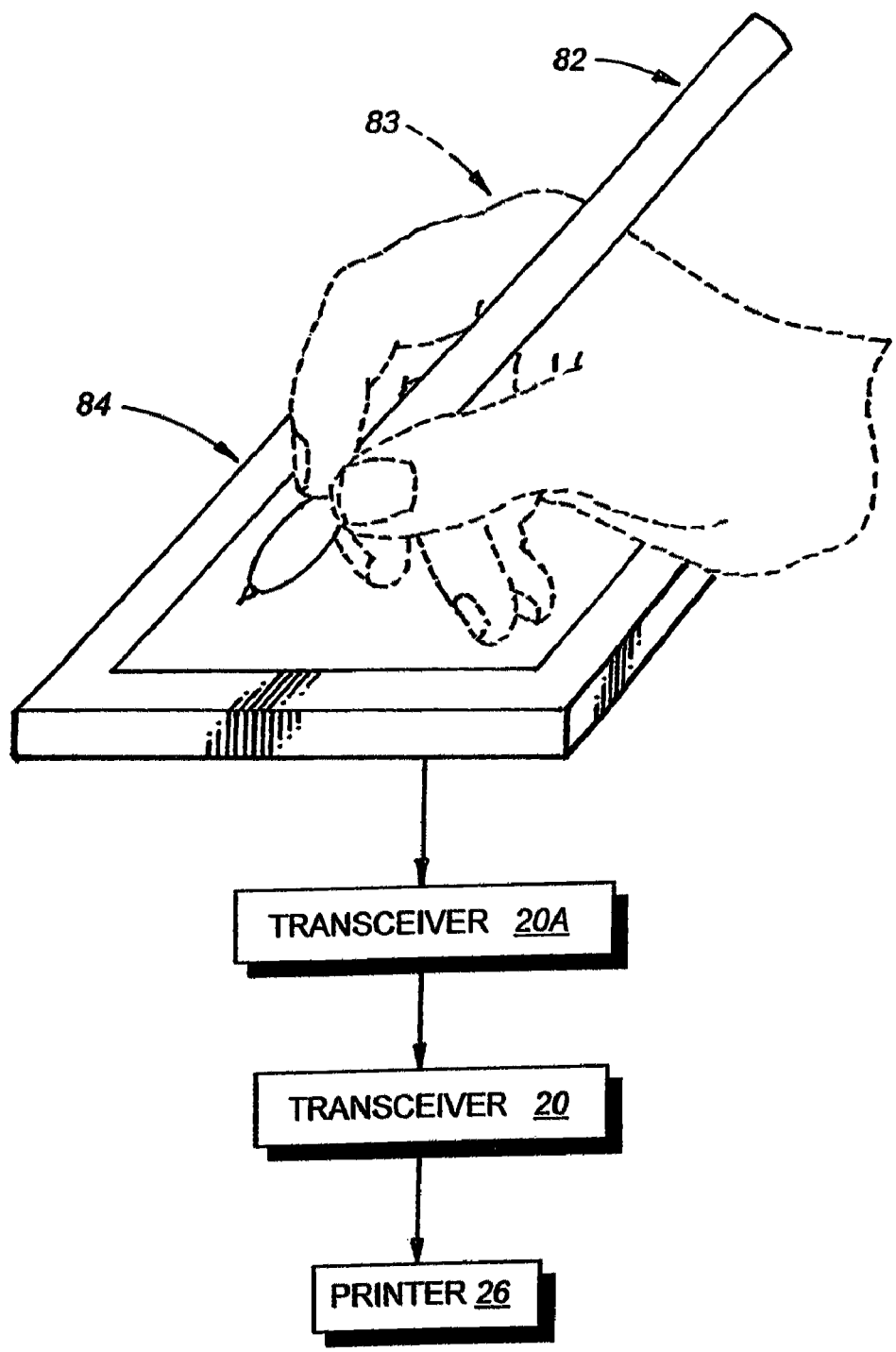
FIG. 17 is a diagram illustrating the dispensing of a prescription during a video conference between two studio booths.

One particular embodiment of the invention comprises utilizing studio booth 10 to dispense prescriptions in the manner illustrated in FIG. 17. After an individual utilizes the booth 10 to conduct an audiovisual conference or audio conference with physician that is at a location remote from the individual, the physician 83 can utilize a stylus 82 or other instrument to write and sign a prescription on a touch sensitive screen 84. Any other desired equipment can be utilized by a physician 83 to prepare necessary data to define and transmit a prescription to a desired location. The prescription, along with any other information needed to print the prescription (for example, the name and address of the physician's practice) is transmitted by a transceiver 20A at the remote location to the transceiver 20 in the studio 10. The transceiver 20 forwards the medical data 64 in the computer memory in booth 10. The computer control, via printer sub-routine 71, transmits the medical data to printer 26 in booth 10 to print the prescription. A hard paper copy of the prescription is printed and dispensed by printer 26. In addition to dispensing a hard copy comprised of paper, booth 10 can be equipped to dispense a hard copy comprising a DVD or other disc or media that can be utilized by the patient to print a prescription or that can read or otherwise utilized by a pharmacy to fill the prescription for the patient. The DVD or disc or other media can be programmed such that the disc can be read only once and/or can be used to print only one copy of the prescription. Alternatively, the patient's booth 10 (or the physician's booth 10) can be located in or adjacent or near a retail or wholesale store that includes a pharmacy. After an audiovisual or audio conference between the physician and patient, the physician can transmit a prescription directly to the pharmacy in the store. The patient can then, when the patient's booth is located in the store, step out of the booth, wait while his or her prescription is filled, and then pickup the prescription from the pharmacy. Locating the booth 10 utilized by the patient in a store with a pharmacy is particularly advantageous because the patient can both carry out his conference with a physician and immediately have a prescription transmitted to the store. The prescription can be transmitted to the pharmacy from the patient's booth 10 or from the physician's booth 10. The prescription can be transmitted from a booth 10 to the pharmacy via wireless signals, over a fiber optic line, over an electrical wire, via satellite, etc.

One advantage of booth 10 is that during the individual's conference with a physician, the camera transmits the patient's picture and voice to the physician. The camera can be adjusted to zoom in or transmit particular areas of the patient's body or to view and transmit other information to the physician or other heath care professional. The bar code (or other identification code or system) on or embedded in the prescription can be utilized to track prescriptions to help insure that they are legitimately issued on an as need basis to patients and to insure that the dispensation of habit forming and other drugs is monitored and controlled. In one embodiment of the invention, any prescription issued by a physician via booths 10 to a patient or directly to a pharmacy is also entered in a computer server accessible by the physician and by the pharmacy. When a patient presents a prescription to a pharmacy (or when the pharmacy receives a prescription via signals from a booth 10), computer equipment at the pharmacy reads the bar code on the prescription, queries the computer server, and confirms that the prescription has been issued, the name of the attending physician, the name of the patient, and the drug to be issued under the prescription.

In some cases audio transmission between the patient in one booth 10 and the physician in another booth 10 may be sufficient so that a video transmission between the booths is not required. It is presently preferred, however, the any audio transmission between a physician and a patient include a video feed such that the physician can see and at least to some extent evaluate the appearance of the patient.

The video conferencing feature of booth 10 can be utilized in conjunction with any of the other functions of booth 10 described herein. For example, when an individual is performing (and also, if desired, recording the performance), the performance may be viewed by another person(s) with whom the individual is conducting a video conference. The other person(s) can be, by way of example and not limitation, a family member, a talent scout, a physician, a modeling agency, a personal relationship agency, etc.

The Remote Studio Booth as Means for Establishing Ownership and Confidentiality for Performer.

One important feature that is preferably, but not necessarily, included in or associated with each remote recording booth is establishing ownership of a performer in a performance recorded in the booth and establishing control of confidentiality of the performance in the hands of the performer. If a performer utilizes music or lyrics or a background picture or design that is provided in and by booth 10 but is protected under copyright law, then the performer does not own all rights to his or her performance. The performer can only own the rights to copy, distribute, and sell his or her performance if an appropriate copyright license or assignment is obtained from the owner of the music or lyrics or background design, and, as well, from the owner of the recording studio based upon the owner's copyright in recording engineering provided by the studio booth 10. Addressing this problem is one important feature of the invention.

It is preferred that the studio owner assign or license his copyright interest to the performer and, importantly, agree to attend to payment of the necessary copyright licensing fees (through ASCAP or other suitable copyright licensing agencies) for the music, lyrics, or background picture utilized in the recording booth during the performance. Licensing by the studio owner from ASCAP, etc. of music, lyrics, and background pictures is preferably accomplished by the studio owner prior to a performer utilizing the remote recording booth.

Further, it is preferred that the studio booth owner agrees that—aside from the music, lyrics, background picture, and recording engineering—the performance is entirely owned by the performer.

Still further, it is preferred that the studio booth owner agrees that the performance is confidential and will not be distributed without the approval of the performer.

Yet further, it is preferred that if the performer agrees to have his or her performance transmitted to a remote location or to a web site owned by the studio owner or another individual, the performance is maintained in confidence at said remote location until the performer authorizes distribution or viewing of the performance at the remote location.

Yet still further, if a performance is transmitted to a remote web site or other location, and the performer elects to incorporate the performance in a personal web site comparable to the numerous "MY SPACE" web sites now existing on the Internet, the performer can still control confidentiality of the performance on his or her personal web site by limiting access to the personal web site.

The foregoing ownership and confidentiality provision are believed important factors in connection with the practicality of operating the remote studio booth. If the copyright ownership is not addressed, then it may be left to the performer to obtain the proper copyright licenses. It is unlikely a performers would undertake or now how to undertake obtaining a copyright license. This would mean that the performance violated copyright law and that the owner of the studio booth can be implicated in violating copyright law. This would expose the performer and studio owner to a lawsuit. In accordance with the invention, the solution to this problem is to secure copyright license before a work is utilized in the studio booth and/or for the studio owner to assign or license to the performer any copyright interest of the studio owner in the performance. This problem does not appear to have been previously addressed.

Figure 19:
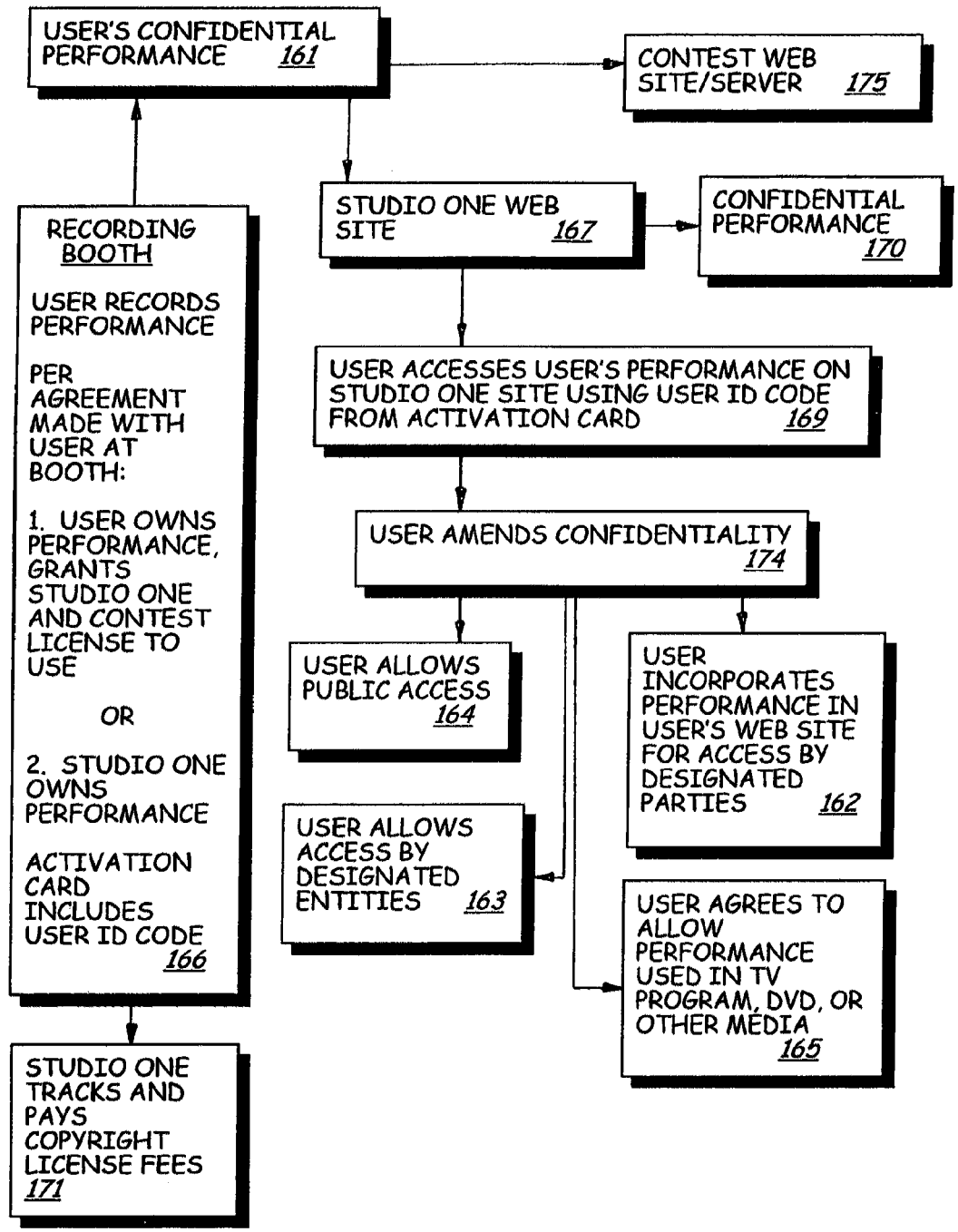
FIG. 19 is a diagram illustrating a confidentiality-ownership flowchart in connection with the use of a studio or recording booth of the invention.

FIG. 19 illustrates one possible confidentiality-ownership flowchart in connection with the use of a studio or recording booth of the invention. In FIG. 19, it is assumed that the entity Studio One is the owner of the recording booth 166. The user records a performance in recording booth 166. Per an agreement entered into by the user at the booth, or at another location where the user obtains an activation card, (1) the user owns the performance and can grant Studio One or another entity conducting a contest via the booth a license to use the performance, or (2) Studio One can own the performance. The activation card utilized in the recording booth includes a user identification (ID) code. Studio One tracks and pays, preferably prior to use of the recording booth to record a performance, any copyright license fees due for use of music, lyrics, or other copywritten works in the booth.

A user's confidential performance 161 is produced in the booth, and the user preferably is granted control over when and where and if the performance is published or transmitted. The user can elect in the booth, or at another designated location remote from the booth, to have the user's performance 161 transmitted to a contest web site or server 175 or to the Studio One web site 167. At web site 167 the performance can, at the election of the user, remain confidential 170. Alternatively, at the web site the user can access his or her performance 169 utilizing the user ID code from the activation card and can amend 174 the confidentiality of the performance.

One way the user amends the confidentiality of the performance is to allow 164 public access to the performance.

Another way the user amends the confidentiality of the performance is to allow 163 access by designated entities.

A further way the user amends the confidentiality of the performance is to incorporate 162 the performance is a separate user's web site for access by designated parties. The separate user's web site can be operated on a server provided by Studio One or can be operated elsewhere. The user may elect to have the separate user's web site accessed only by user or only by a limited number of other parties or by the public.

Still another way the user amends the confidentiality of the performance is to allow 165 the performance to be utilized in a TV program, DVD, or other media distributed to a selected audience(s).

FIG. 20 illustrates the first phase, namely the RECORDING BOOTH: PRE-PERFORMANCE phase 180 in the recording booth, in another ownership-confidentiality embodiment of the invention. In the pre-performance phase

180, Studio One (the owner of the recording booth) notifies the user, either during registration (at the booth, on the Internet, etc.) or when the user is in the booth, that (1) the user owns the recorded performance including any copyright interest of Studio One in the performance, (2) Studio One tracks and pays on behalf of the user copyright license fees for the user's performance in connection with music, lyrics, artistic backgrounds, etc. provided by and used in the recording booth. Alternatively, although not presently preferred, Studio One can claim ownership of all or some of the rights in the user's performance.

During the pre-performance phase 180, the recording equipment in the recording booth scans and retains the user ID code on the user's activation card.

During the pre-performance phase 180, either during registration or while in the recording booth, the user typically agrees to transmit the performance to the Studio One web site, to a contest web site, or to another location.

During the pre-performance phase 180, the user can allow or agree to (1) public access to the performance, (2) access by a limited number of designated parties to the performance, (3) incorporation the performance in the user's web site (via the Studio One web site, via e-mail, or via another transmission), (4) using the performance in a TV show, DVD, or other media, (5) use of the performance in a contest, (6) other use of the performance, or (7) not allow the performance to be used or viewed.

Figure 21:
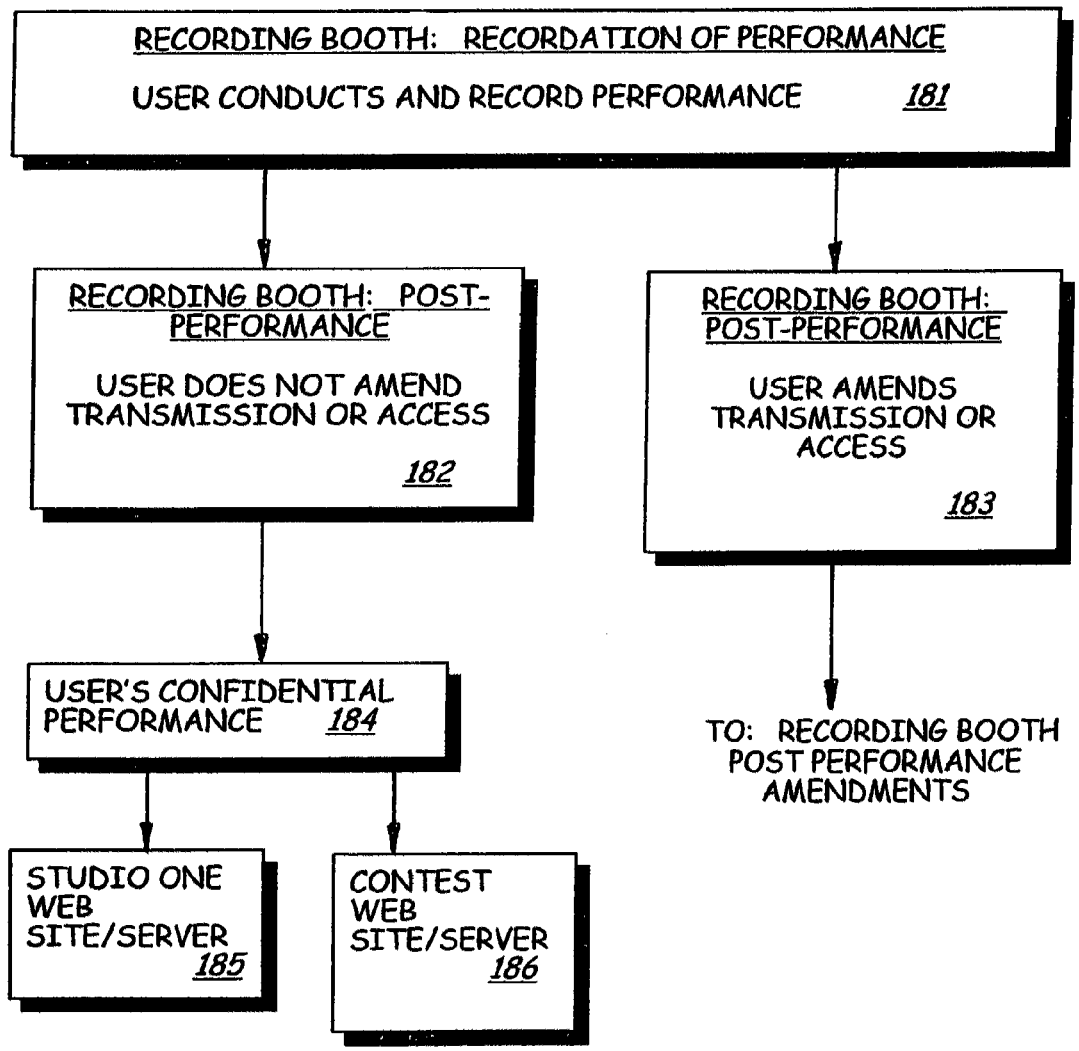
FIG. 21 is a diagram illustrating the next phase in the ownership-confidentiality embodiment of FIG. 20.

After the pre-performance phase, the next phase is illustrated in FIG. 21 and consists of the RECORDING BOOTH: RECORDATION OF PERFORMANCE phase 181 in the recording booth. The user conducts a performance that is recorded by equipment in the recording booth.

After the recordation of performance phase 181, the user may elect not to amend 182 the transmission and access selected by the user prior to recordation of the performance. In this case, the user's confidential performance 184 can, for example, be transmitted to the Studio One web site/server 185, to a contest web site/server 186, or to another selected destination.

Alternatively, the user may elect to amend 183 the transmission or access that was selected by the user prior to recordation of the performance. In this case, any of the amendments illustrated in FIG. 22, RECORDING BOOTH: POST PERFORMANCE AMENDMENTS 187, may be selected.

In FIG. 22, possible amendment of transmission selections earlier made by the user can include cancelling the transmission of the performance to (a) Studio One web site/server, (b) contest web site/server, or (c) another destination. The amendment transmission elections can also include the election to transmit the performance to a Studio One "MY SPACE" (SM) type web site or another designated location.

Possible amendments of access selections or choices earlier made by the user can include cancelling (a) public access, (b) access by a limited number of designated parties, (c) use of performance in a TV show, DVD, or other media, (d) use of performance in a contest, or (e) other use. The amendment of access selections earlier made can also include (a) permitting access to the recorded performance in a Studio One web site, (c) permitting access to a job interviewer, (d) permitting public access, (e) permitting access by a limited number of designated parties, (f) permitting use of the performance in a TV show, DVD, or other media, (g) permitting use of the performance in a contest, or (h) permitting another use.

After the POST PERFORMANCE phase 182, 183 in the recording booth, the next phase is the STUDIO ONE WEB SITE: POST PERFORMANCE phase 188 at the Studio One web site or at another designated location.

When the user accesses the Studio One web site utilizing the user ID code provided at the recording booth, the user can elect not to amend the transmission or access selections that the user made at the recording booth.

The user can elect to amend the transmission elections made at the recording booth. Such amendments can comprise cancelling transmission of the performance to a contest web site/server or other destination, or, permitting transmission of the performance to a Studio One "MY SPACE" (TM) type web site or to another destination.

The user can also elect to amend the access selections that were made at the recording booth. Such amendments can comprises canceling public access; canceling access by a limited number of designated parties; canceling use of the performance in a TV show, DVD, or other media; canceling use of the performance in a contest; or, canceling other uses of the performance.

The Remote Booth as a Means to Participate in a Game of Chance

The remote studio booth 10 of the invention is believed to be well suited to conducting a game of chance with a gambling entity like a remote casino. The booth permits a user to participate in real time gambling and also provides a variety of avenues to insure that the user is of age, to insure the user's identity, and to insure that the gambling is legitimate and can be monitored by the proper governmental and regulatory authorities.

Example

A studio booth 10 is placed in a shopping center, airport, university campus or other public or non-public location.

An individual approaches the registration station on the right of door 17 and sees on touch screen 13 the "WELCOME" information shown in the top illustration of screen 13 depicted in FIG. 24. Three illustrations of screen 13 are depicted in FIG. 24. The individual reads the "WELCOME" information and presses her finger against screen 13 over the "PRESS TO START" box. The "CHOOSE A SESSION" information shown in the middle illustration of screen 13 in FIG. 24 appears. The individual presses her finger against the screen 13 over the box to the left of "♣♦♥♠Video conference with casino to play Game of Chance" and then presses her finger against screen 13 over the "CONTINUE" box. The "SELECT A CASINO" information shown in the lower, or third, illustration of screen 13 in FIG. 24 appears. The individual presses her finger against screen 13 over the box to the left of "Blue Nickel". "THE BLUE NICKEL WELCOMES YOU!" display shown in the top illustration of screen 13 in FIG. 25 appears. The individual reads the information, and uses the keyboard at the registration station to enter her account number and password. The display shown in the middle illustration of screen 13 in FIG. 25 appears. This display confirms that the account number and password have been verified and asks the individual to utilize the fingerprint or optical scanner that is provided at the registration station. She places her finger against the fingerprint scanner. The display shown in the bottom illustration of screen 13 in FIG. 25 appears. This screen confirms that her identity has been confirmed and that any transactions she has with the Blue Nickel may be monitored by IRS or other government or regulatory agencies; and, also confirms that any winnings will be sent to her account within seven (7) days. Other alternatives that can, if desired, be provided to the individual to collect winnings are (a) printing a receipt (inside or outside of the booth) that is taken by the individual to another location for redemption, (b) dispensing a debit card, or, (c) dispensing the winnings at the booth from a currency dispensing machine located at the booth.

The individual presses the screen over the "CONTINUE" box. The printer 82 then prints and dispenses the activation card illustrated in FIGS. 27 and 28.

When the activation card is dispensed, the "WELCOME" information shown in the illustration of screen 13 in FIG. 26 appears. The information in FIG. 26 notes the time the booth will be ready for Sandi's session and notes that the casino employee must be able to view Sandi when she is in the booth.

Sandi reads the side of the activation card depicted in FIG. 27 and notes that her performance number is 52; notes that she must insert the card in a slot inside the booth to activate her session; notes the bar code or other identification code imprinted on the card (not shown in FIG. 27); and notes the contest details and disclaimers on the back of the activation card. FIG. 28 illustrates the back of the activation card.

Sandi note the time is 1.05 p.m. and again notes that the estimated time the booth 10 will be ready for her session is 3:30 p.m. See looks up at screen 33. Displayed on screen 33 is "IN SESSION. NO. 37".

Figure 30:
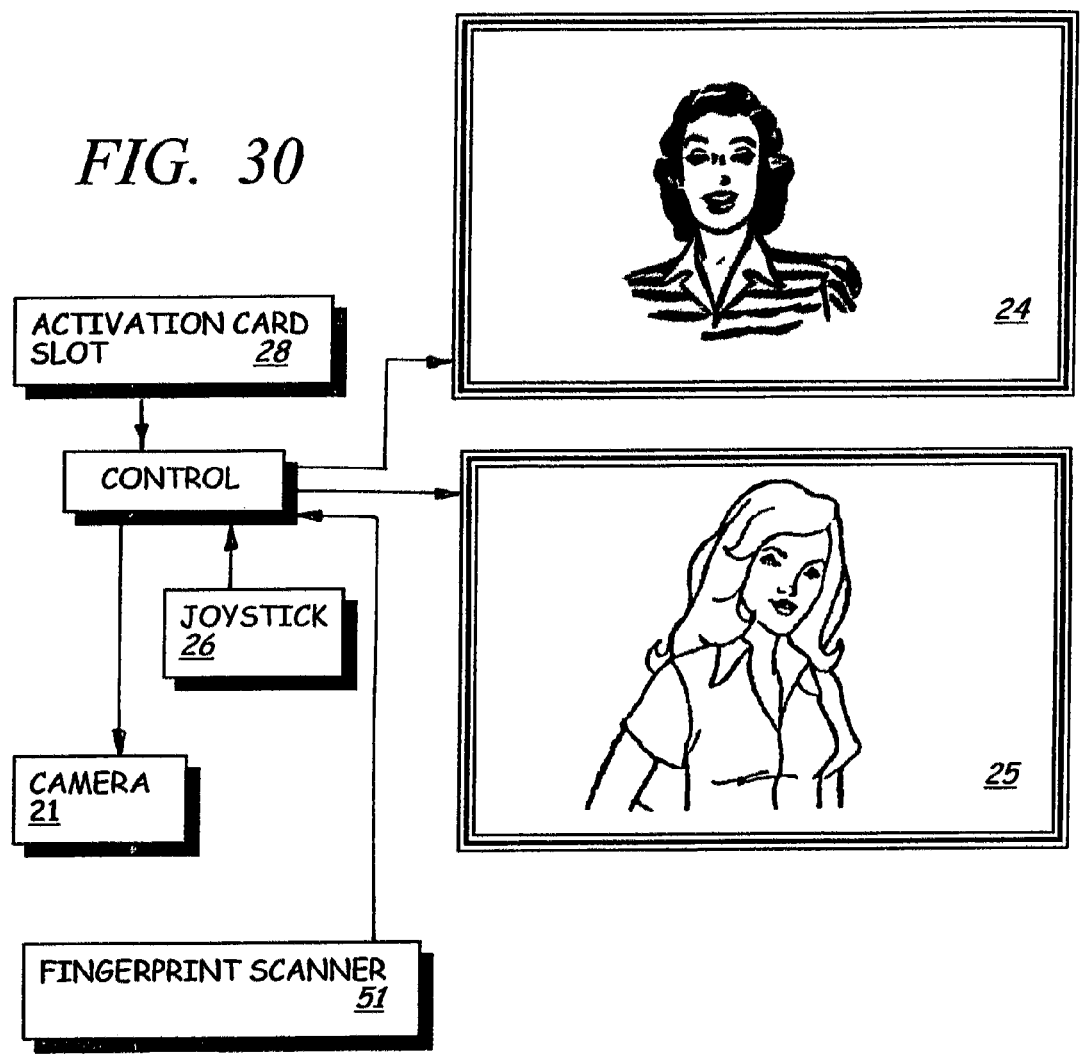
FIG. 30 is a diagram illustrating, when an individual is using the booth to participate in a game of chance, the operative relationship between a pair of display screens inside the studio booth, the activation card, the control, the joystick, the camera, and a fingerprint scanner.

Sandi leaves the booth 10 and returns at 3:25 p.m. Displayed on screen 33 is "IN SESSION. NO. 51". After five minutes, an individual leaves the booth. Sandi enters and locks door 17 from inside the booth. She notes that there are two display screens 24, 25 inside the booth. Screen 24 displays the information shown in the top illustration of screen 24 in FIG. 29. Screen 25 displays and image of her standing, or sitting, in the booth. She inserts her activation card in the slot inside booth 10. The information shown in the bottom illustration of screen 24 in FIG. 29 appears. The visual display of time shown on screen 24 begins to count down: 30 29 28 27 26 25 . . . . During the thirty second count down, Sandi utilizes joystick 26 (FIG. 15) or other controls provided inside the booth 10 to adjust the height and focus (zoom) of the camera 21 such that her image on screen 25 is that depicted in FIG. 30. After the countdown on screen 24 reaches zero, the image of a Blue Nickel employee named Sally appears on screen 24 as shown in FIG. 24. Sally's voice is produced by a speaker in booth 10.

Sally: Good afternoon Sandi. I'm Sally at the Blue Nickel. You look nice today.

Sandi: Thank you.

Sandi's voice and image are detected by audio visual equipment in booth 10 and transmitted to Sally's casino so Sally can view and hear Sandi.

Sally: Would you please let me verify your identity again by placing your forefinger on the fingerprint scanner in the booth?

Sandi: O.K.

Sandi places her finger on the fingerprint scanner 51.

Sally: Looks good, Sandi. I have your account information, including a credit card that we can use, if necessary, to bill you. What would you like to do today?

Sandi: Is it possible to play a slot machine?

Sally: Yes. I can place a display of the machine on the screen once you tell me which machine. We have 25 cent, one dollar, and five dollar slot machines. You push the "ENTER" button on your keyboard each time you want to play. Your credit card will be automatically billed for the amount of your bets at the end of the game. And, of course, your winnings will be transmitted to your account. At the end of the game, the printer in your booth will print a receipt showing how much you bet and lost in total and how much you won total along with the last four digits of your account number, the date, the time, the "BLUE NICKEL" logo and address, and your name.

Sandi: O.K. How about roulette?

Sally: Yes. I can place a picture of the roulette table on the screen. To enter the number (or numbers) you want to bet on you type in, for example, "10", followed by pressing the enter key, followed by typing in the amount of money you want to bet, followed by pressing the enter key. You do that for each number individually: enter the number and enter the amount of the bet on the number. If the number and the amount you want to bet are not entered by the time the roulette wheel is turned, your bet doesn't count. At the end of your game, the printer in your booth will print a receipt shown how much you bet and lost total and how much you won total, along with the last four digits of your account number, the date, the time, the "BLUE NICKEL" logo and address, and your name.

Sandi: OK. I'd just like to bet $1,000.00 on Blue Note to finish second in the fifth race today at the Blue Nickel Race Track.

Sally: It's done. Is your receipt printing out?

Sandi: Yes.

Sally: Does it show that you bet $1,000.00 on Blue Note to finish second in the fifth race today at the Blue Nickel Race Track?

Sandi: Yes it does.

Sally: Don't lose that receipt. If Blue Note comes in second, your winnings will be forwarded to your account. Is there anything else I can help you with?

Sandi: No thank you.

Sally: Thank you for your business, Sandi. Good-bye.

Sandi: Good-bye.

Sally's image disappears from screen 24. Sandi takes her receipt and leaves the booth 10.

Performance-Driven Super Network with Recording Booth Nexus

In another important embodiment of the invention, recording booth 10 is the nexus of a wide ranging network of nodes to promote or advertise a product or service. The network can be described by the coined words "super network" because of the potentially vast size of the network and of the multitude of advertising opportunities that such a network could provide. The network derives from and is driven by performances recorded in one or more booths 10. Any company or companies could advertise on such a network. In the following discussion, however, it is assumed that GENESIS is an Internet search engine comparable to GOOGLE™, and that GENESIS has purchased the sole right to advertise on the network. It is also assumed that the company STUDIO ONE is the owner and operator of each booth 10 and is the owner/operator of the STUDIO ONE Internet web site.

A. Pre-Performance Network Nodes

Figure 31:
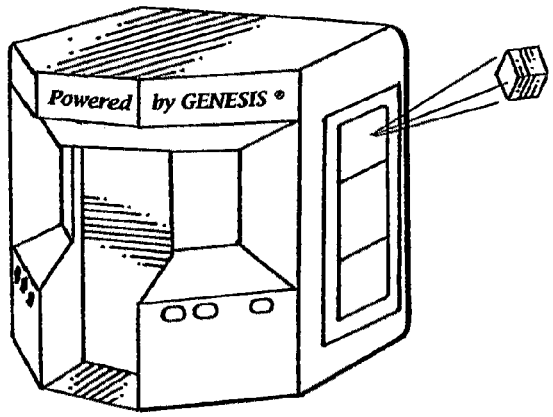
FIG. 31 is a diagram illustrating network nodes available to an advertiser in connection with an individual's performance, but prior to the performance being conducted and recorded in a studio booth.

Potential pre-performance nodes in the network are illustrated in FIG. 31 and include registration 100 at the Studio One Internet web site, a virtual tour 101 of booth 10 at the Studio One Internet web site 101, registration 103 on site at the Studio One booth 10, and promotional banner and screens 104 on the exterior of the booth 10. The manner in which GENESIS advertises at each node can vary as desired, but the following examples are provided.

When an individual registers on-line at the Internet web site of Studio One, the promotional message "Powered by GENESIS®" can appear on menus or displays that appears on an individual's computer screen when the individual is registering. FIG. 36 illustrates the first three menus which could appear when the individual is registering on the Internet to utilize a Studio One booth 10. When the individual begins the registration procedure on the Internet, the top menu in FIG. 36 appears. This menu begins "WELCOME! TO STUDIO ONE". The individual causes the top menu to disappear and the next (middle) menu to appear by using his/her mouse to click on the "PRESS TO START" box. The middle menu appears. The middle menu includes the heading "CHOOSE A SESSION". After the individual selects a session, the individual causes the middle menu to disappear by using his/her mouse to click on the "CONTINUE" box. The middle menu disappears from the screen and the lower menu in FIG. 36 appears. And so on during the registration process. Each of the menus includes advertising for GENESIS in the form of the promotional message "Powdered by GENESIS®". Advertising or promotional material of GENESIS can, of course, take any desired form.

In FIG. 31, the recording booth includes a traveling banner that extends around the top of the booth. The promotional message "Powered by GENESIS®" can, as illustrated in FIG. 31, appear in the traveling banner. Other advertising for GENESIS can appear in other ones of the exterior displays or display screens on recording booth 10.

When an individual is taking a virtual tour of the recording booth 10 at the Studio One web site, advertising material for GENESIS can be included in renditions of booth 10, of display screens, of registration procedures, etc.

B. Network Nodes Available During Recordation of Performance

Figure 32:
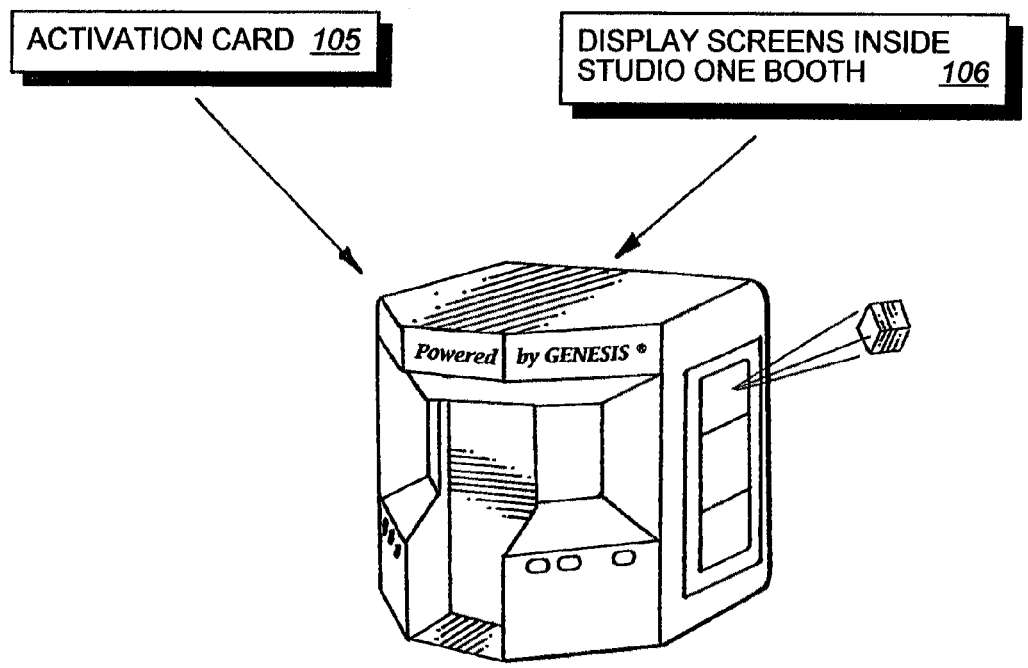
FIG. 32 is a diagram illustrating network nodes available to an advertiser when an individual is recording a performance in a studio booth.

Potential nodes in the network that are available during the recordation in booth 10 of a performance are illustrated in FIG. 32 and include activation card 105 and display screens inside the Studio One booth 106. The manner in which GENESIS advertises at each such node can vary as desired, but the following examples are provided.

The activation card can, as illustrated in FIG. 35, include the promotional message "Powered by GENESIS". When the individual possessing the card inserts the card inside booth 10, it is likely that the individual will consciously or subconsciously view that promotional message.

Display screens inside booth 10 can include GENESIS advertising material. FIG. 34 illustrates a sequence of three menus that can appear when an individual is inside booth 10 to record a performance. The top menu in FIG. 34 includes the heading "WELCOME!". After the individual follows the instructions set forth in the top menu and inserts her activation card, the top menu disappears and the middle menu appears. The middle menu includes the heading "SANDI MARTIN". After Sandi Martin completes her performance, the bottom menu in FIG. 34 appears. This menu includes the heading "YOUR PERFORMANCE IS COMPLETE". Each of the menus in FIG. 34 includes the promotional message "Powered by GENESIS®". Any desired visual, audio or other advertising material for GENESIS can be included or incorporated in a menu or in any other display that appears on a screen or other area in booth 10 (or in another network node).

C. Network Nodes Available Post-Performance

Figure 33:
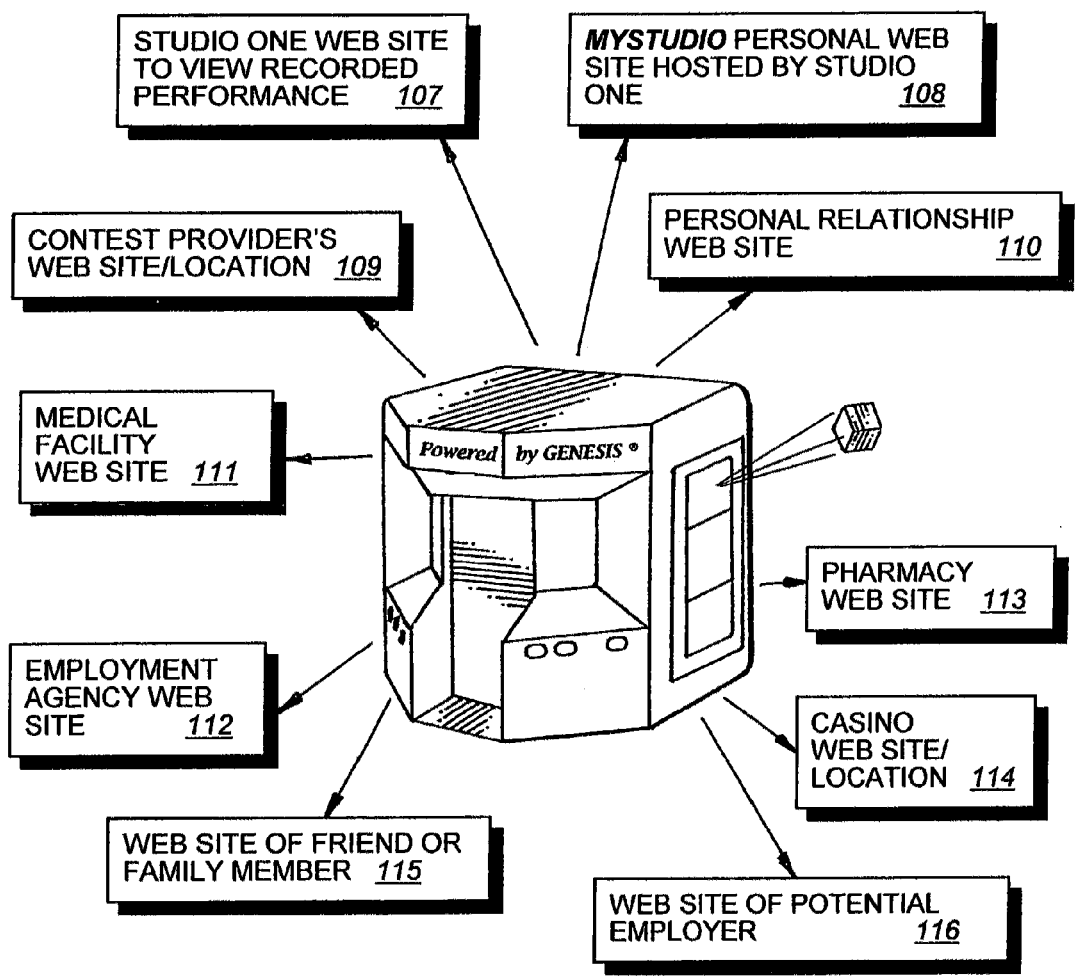
FIG. 33 is a diagram illustrating potential network nodes available to an advertiser in connection with an individual's performance, but after the performance is recorded in a studio booth.

FIG. 33 illustrates potential post-performance nodes in the network which arise after an individual has recorded a performance in a booth 10. These nodes include, without limitation, the Studio One web site (where an individual views his or her recorded performance 107), a MYSTUDIO personal web site hosted by Studio One 108, a contest provider's web site/location 109, a personal relationship web site 110, a medical facility web site 111, a pharmacy web site 113, an employment agency web site 112, the web site 115 of a friend or family member of the individual who records his or her performance in booth 10, a casino web site/location 114, and the web site of a potential employer 116.

With respect to node 107, an individual visits the Studio One web site after the individual has recorded a performance in booth 10 and has elected to have the performance transmitted to the Studio One web site for viewing by the individual. When the individual views his performance, the promotional phrase "Powered by GENESIS®" (or other desired GENESIS advertising material) can appear at the beginning of the performance or at any other desired location in the performance or in the Studio One web site. In one particular embodiment of the invention, the promotional phrase "Powdered by GENESIS®" (or other desired advertising material) travels along with the recorded performance so that whenever the performance is played or viewed, said promotional phrase appears at least temporarily during the performance.

With respect to node 108, an individual may elect to have her or his own MYSTUDIO personal web site which can be used to communicate with others on the Internet and on which the individual can incorporate any desired pictures, music, film clips, etc. The individual can store on his MYSTUDIO personal web site the performance(s) that the individual recorded in booth 10. The promotional phrase "Powered by GENESIS®" can appear on the personal web site, can appear in the recorded performance, etc.

With respect to node 109, when a performance recorded in booth 10 is received at the web site or other location of a contest provider to be viewed by the contest provider or the provider's agent, the promotional phrase "Powered by GENESIS®" can travel along with and appear at least temporarily during viewing of the recorded performance. Similarly, the promotional phrase "Powered by GENESIS®" can travel along with and appear in the recorded performance when the recorded performance is viewed at a node 110 to 116.

The personal relationship web site 110 can comprise a web site where individuals submit personal information in an attempt to find an individual to date, to marry, etc. As earlier noted herein, a recording booth 10 can serve as a portal to such a web site. The booth 10 can be the "first stop" for an individual in the sense that the individual can record a performance in booth 10, enter appropriate information, and have the recorded performance and appropriate information transmitted to the personal relationship web site to register for the first time with the personal relationship web site 110. In another embodiment of the invention, an individual has previously registered and established an account with the personal relationship web site 110 prior to utilizing booth 10, and, a performance subsequently recorded in booth 10 is be transmitted to the personal relationship web site 110 for incorporation in the individual's previously established account. When an individual's recorded performance is transmitted to a personal relationship web site, it normally is with the understanding that the performance can be viewed by customers or other individuals accessing the web site 110 in an attempt to find an individual to date, to marry, etc.

When booth 10 is utilized for a real time video conference with another individual at a casino 144, at a hospital or pharmacy or other medical facility, at an employment agency, etc., the video of the individual in booth 10 that is viewed by the individual at the casino, medical facility, etc. can include (typically in a fashion that does not interfere with conducting the video conference) the byline "Powered by GENESIS" or can include other desired material advertising or promoting GENESIS.

When the performance recorded in booth 10 consists of a still photograph, the byline "Powered by GENESIS®" can be included at the bottom or on the rear of the photograph, preferably in a fashion not to interfere with the desired effect of the photograph.

One preferred feature of the network of the invention is that it is likely that many of the nodes in the network, and therefore the advertising associated with the nodes, will be viewed by a great many individuals, as is reflected in Table I below.

TABLE I

Potential Viewing Audience of Network Nodes

| Node | Audience |
|---|---|
| 100: Registration at Studio One Internet site | Performers |
| 101: Virtual Tour of Studio One booth at Internet site | Performers; Public |
| 104: Promotional Screens on Exterior of Booth | Performers; Public |
| 103: Registration on site at Studio One Booth | Performers |
| 105: Activation Cards | Performers |
| 106: Display Screens on site inside Studio One Booth | Performers |
| 107: Studio One web site to view recorded performance | Performers; Public |
| 108: MYSTUDIO web site hosted by Studio One | Performers; Public |
| 109: Contest Provider's web site/location I | Employees of Contest Provider; Public |
| 111: Medical facility | Physician; Other Medical Personnel |
| 112: Employment agency web site/location | Employment agency personnel; various employers |
| 113: Pharmacy web site | Pharmacist |
| 114: Casino web site | Casino employees |
| 115: Friends; family members | Friends; family members |
| 116: Wet site of potential employer | Employer's personnel department |

The recording booths 10 and the performances recorded in the booths 10 are the glue that link together the various nodes in the network and create the network of the invention. Incorporating promotional material into the network produces a promotion network with an unusually large audience, which promotional network can be particularly effective when the number of companies or individuals advertising on the network is limited. Although the number of advertisers on the network can be any desired number, in one embodiment of the invention, the number of advertisers is in the range of one to five, preferably in the range of one to two, and most preferably is one.

Definition of Performance Format and Integration of Scenic Environmental Backdrop Another important feature of the invention which would, as is the case with other features of the invention herein, standing alone significantly improve the commercial viability and practicality of using booth 10, is the system for formatting a performance.

The first step in formatting a performance is to define the kind of performance by placing it in a desired category that will include only a portion of performances recorded in booths 10. Such categories can be defined as desired; however, the following is provided by way of example.

One category of performances can comprise all performances entered into a $1^{st}$ contest. Consequently, each performance for the $1^{st}$ contest comprises one kind of performance. A second category of performances can comprise all performances entered in a $2^{nd}$ contest different from the $1^{st}$ contest. Consequently, each performance for the $2^{nd}$ contest comprises a second kind of performance. A third category of performances can comprise all performances for a still "full body" photo shot for a model. Consequently, each still "full body" photo for a model comprises a third kind of performance. A fourth category of performances can comprise family portrait. Consequently, each family portrait comprises a fourth kind of performance. A fifth category of performances can comprise an interview or other performance that is to be submitted to apply for a job. Consequently, each performance that is to be submitted for a job comprises a fifth kind of performance. A sixth category of performances can comprise a performance that is to be submitted to a personal relationship web site to advertise for a mate or date. Consequently, each performance for a personal relationship web site comprises a sixth kind of performance.

Once the kind of performance is defined, the performance is further formatted by selecting at least one scenic environmental backdrop for that kind of performance. The backdrop is selected by determining a selected geographical locale, if any, and by determining the desired makeup or content of the backdrop. For example, any performance that is to be submitted in a category comprising a $1^{st}$ contest may require a specific backdrop that is associated with the geographical locale of Hollywood, Calif. and that has a desired content comprising a sound stage at a particular studio in Hollywood. Any performance that is to be submitted in a category comprising a $2^{nd}$ contest may require a specific backdrop that is associated with the geographical locale of Hawaii and that has a desired content comprising a particular beach in Hawaii as the desired makeup of the backdrop. Any performance that is to be submitted in a category comprising a full body shot of a model may not require any particular geographical locale and may require a desired content comprising a stage runway of the type utilized for models at a fashion show. Any performance to be submitted in a category comprising family portraits may not require any particular geographical locale and may require a simple white background as the desired content of the backdrop. Any performance to be submitted in a category comprising a job interview may not require any particular geographical locale and may require an office background with an American flag as the desired content of the backdrop.

Once the desired content of the scenic backdrop is determined, formatting of the performance is continued by preparing an analog or digital image of the backdrop. This is typically accomplished by taking a photograph of the particular stage, beach, etc. that is selected, but can also be accomplished by designing a backdrop on a computer or by any other desired means.

After the image of the backdrop is prepared, formatting of the performance is completed by storing for recall the image in a digital or analog or other format. In one embodiment of the invention, the image of the backdrop is stored digitally, on tape, etc. at the website of the owner or operator of booth 10 and is transmitted to booth 10 when that particular backdrop image is selected for a particular kind of performance in the booth by an individual(s). In another embodiment of the invention, the image of the backdrop is stored at booth 10 in memory in a graphics source computer 140 (FIG. 46) or is stored at booth 10 in any other desired format.

When an individual utilizing booth 10 registers either at the booth 10, on-line at a web site, or at another desired location, a plurality of performance categories are provided from which the individual can select at least one category. As noted, by way of example and not limitation, such categories can comprise a 1<sup>st</sup> contest, 2<sup>nd</sup> contest, full body model shot, family portrait, etc. Consequently, when the individual selects a particular category, the kind of performance is selected. In one embodiment of the invention, simply selecting the kind of performance can determine the scenic backdrop that will be utilized. For example, if an individual selects a contest, the contest may require use of a scenic backdrop with a geographical locale in New York City and a desired makeup consisting of the skyline 133 of New York City; and, when the individual conducts his or her performance in booth 10, that performance automatically incorporates that particular backdrop 133 into the individual's performance. In a further embodiment of the invention, when backdrop 133 is recalled during an individual's performance, then during the performance the backdrop 133 appears on screen 25 along with the individual 132 such that the individual can view both simultaneously in the manner illustrated in FIG. 38.

In a further embodiment of the invention, when an individual selects a kind of performance while registering to utilize a booth 10, the individual may be given the option of selecting a scenic backdrop from a list of two or more backdrops. For example, if the individual selects a performance which consists of the individual being photographed with a celebrity, a list of possible celebrities appears. The list may include, for example, Paris Hilton, Jennifer Aniston, and Brad Pitt. The individual selects one celebrity from the list. If the individual selects Jennifer Aniston, then when the individual's performance begins, a backdrop including a picture of Jennifer Aniston is utilized and preferably appears on screen 25 along with the individual so that the individual can position herself or himself with respect to the picture of Jennifer Aniston.

Figure 46:
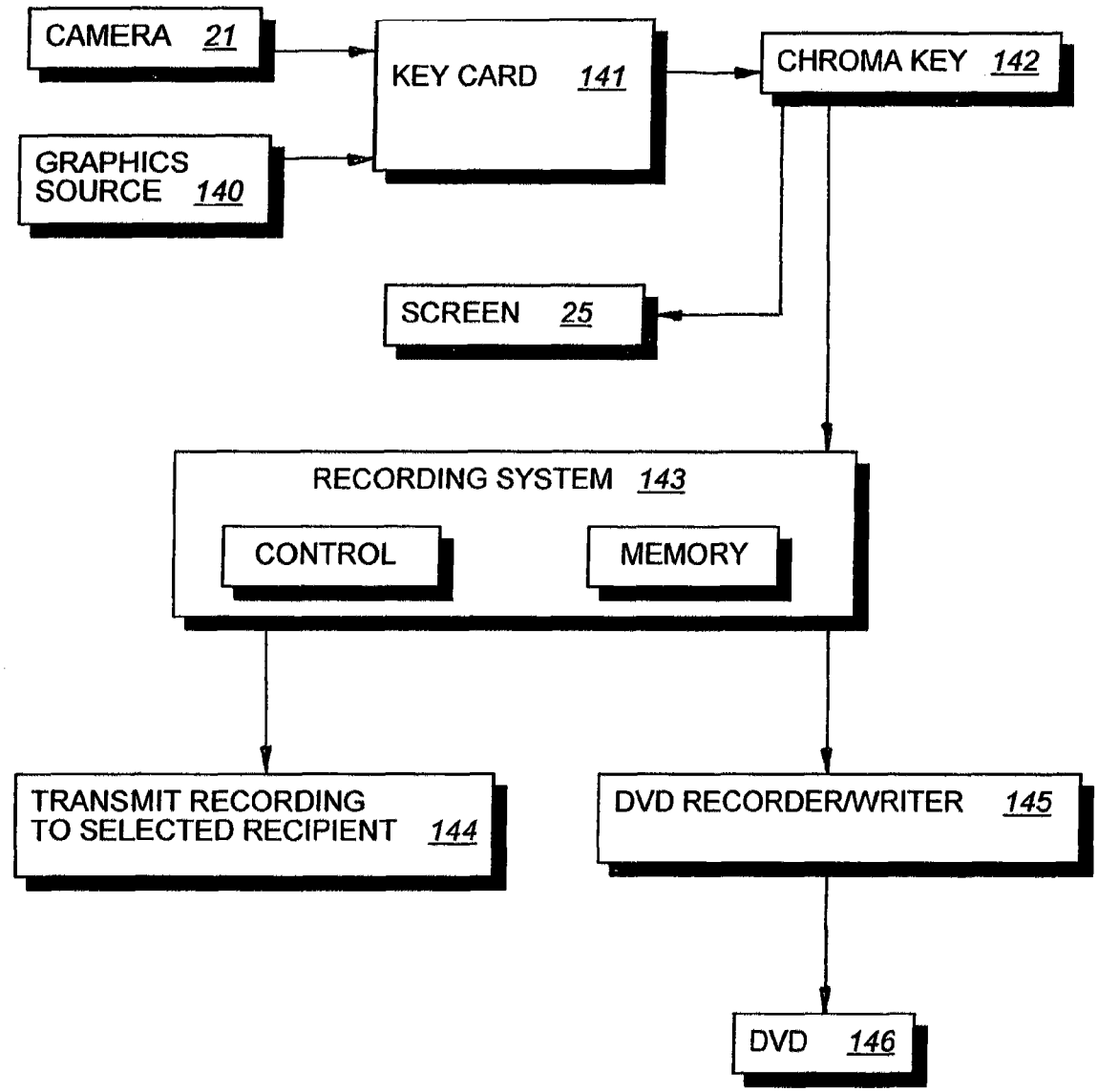
FIG. 46 is a block flow diagram illustrating an automatic system for processing audio and visual signals to produce a DVD including a performance recorded in a studio booth.

The integration of a scenic backdrop with an individual's performance is explained in more detail with reference to FIGS. 37, 38 and 46. For purposes of the remainder of the discussion with respect to FIGS. 37, 38 and 46, the name of the individual 132 is Sandi Martin. When Sandi registers to utilize booth 10, she selects a modeling contest. The kind of performance required by the contest comprises a full body still shot (the contest can, if desired, permit a contestant to select one kind of performance from a menu of two or more different kinds of performances and submit the selected performance to be judged in the contest against other kinds of performances that are noted on the menu and are submitted by other contestants.) The entity conducting the modeling contest earlier formatted Sandi's kind of performance by selecting and storing for recall a single backdrop 133 (two or more backdrops could have, if desired, been selected and a contestant given the opportunity to select only one of the backdrops for the contest.) with a locale of New York City and a desired content consisting of a portion of the skyline of New York. When Sandi selects the modeling contest, this backdrop is automatically designated and selected by the control system in booth 10 to be utilized in conjunction with Sandi's modeling performance. The backdrop 133 is stored, normally along with other different backdrops for other kinds of performances, in graphics source 140 (FIG. 6). During Sandi's 132 modeling performance in booth 10, she stands in front of and stands on a screen 131 in the manner illustrated in FIG. 37. Screen 131 can be any desired color(s) and have any desired design. For example, the screen can comprise a wall with a vertical surface painted green or blue or another selected color. Or, the screen can comprise a wall with a white vertical surface that appears green or blue or another color because a green light, blue light, etc. is directed at the wall to illuminate the wall and make the wall appear green or blue. In one important embodiment of the invention, the screen comprises a "Chroma Key" screen. The fabric or other material comprising such screens ordinarily has a green or blue or gray color. The green and blue colored screens are typically more difficult to utilize because the lighting must be carefully adjusted to illuminate uniformly the entire screen. The preferred "Chroma Key" screen is a CHROMATTE™ fabric screen produced by Reflecmedia EMEA of Road One, Winsford Ind Est., Winsford, Cheshire, CW7 3QQ, United Kingdom, www.reflecmedia.com. The fabric comprising a CHROMATTE™ screen is, in contrast to conventional blue and green colored materials, gray.

A gray CHROMATTE™ fabric screen contains millions of tiny glass beads that act as reflectors and return light that emanates from a source toward the screen. The light is reflected from the screen back toward the source of the light. Consequently, if in FIG. 37 a ring of small green lights is placed adjacent and extends circumferentially around the lens of camera 21, light from the ring travels toward a screen 131 consisting of CHROMATTE™ fabric, and is reflected from screen 131 back to the camera lens. The screen 131 therefore appears to camera 21 to be green. If light from the ring were blue, the screen 131 would appear to the camera to be blue. If light from the ring were orange, the screen 131 would appear to the camera to be orange. And so on. A CHROMATTE™ fabric screen 131 produces a uniform green, blue, etc. background behind an individual like Sandi Martin that is standing intermediate camera 21 and screen 131.

Figure 37:
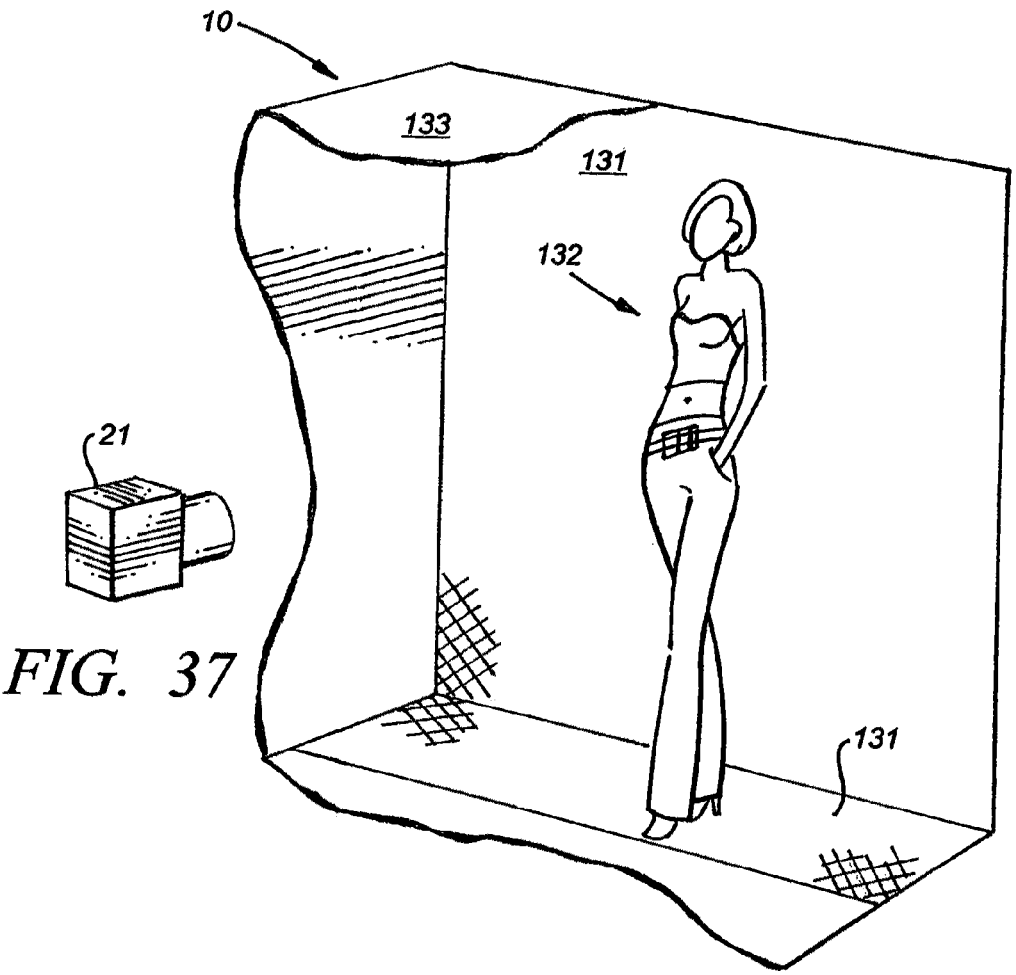
FIG. 37 is a partial perspective view of the interior of a studio booth illustrating the use of a chroma key screen in integrating a scenic background and an audio and visual recording of an individual to produce an integrated recording.
Figure 38:
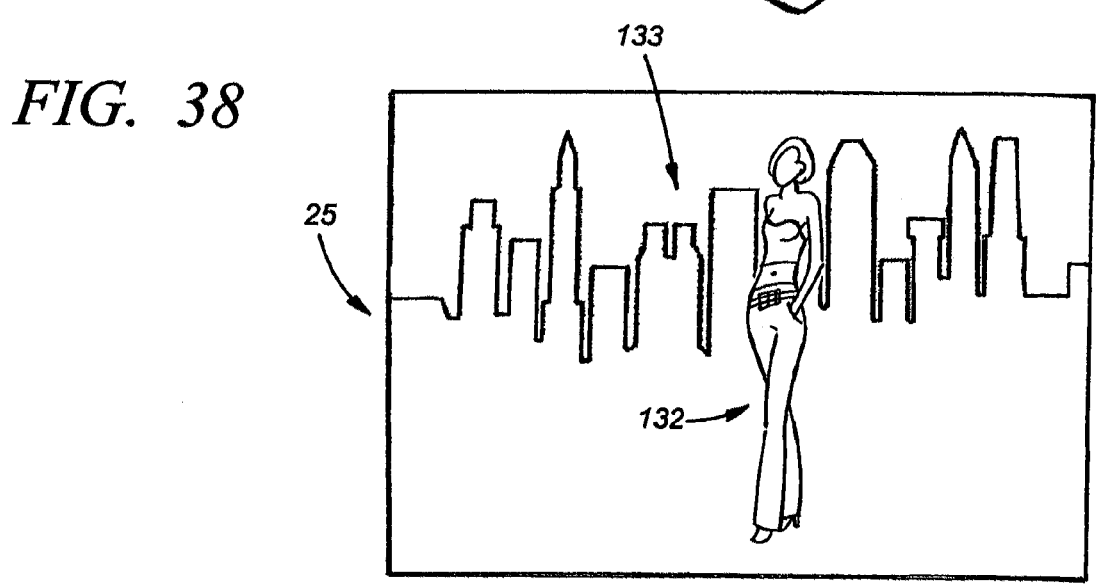
FIG. 38 is a front view illustrating a display screen inside a studio booth that is viewed by an individual during a recording session and that continuously depicts in real time the integrated recording being produced by the studio booth.

As is illustrated in FIG. 37, the screen material preferably extends from the vertical wall behind Sandi 132 and onto the horizontally oriented floor of booth 10 so that the floor beneath Sandi 132 appears to have the same color as the wall behind Sandi.

As is shown in FIG. 36, during Sandi's modeling performance, camera 21 produces signals representing Sandi 132 and the blue or green colored screen 131 behind Sandi 132. These signals are transmitted to a key card 141. The signals from camera 21 can also include audio signals produced by a microphone that monitors speech, singing, etc. by Sandi 132. Similarly, signals representing the backdrop 133 selected for Sandi's performance are transmitted from graphics source 140 to key card 141. As noted earlier, the backdrop 133 for Sandi's performance normally is selected when Sandi registers to utilize a booth 10 to record one of her performances. The backdrop 133 is selected by the control system in booth 10 either automatically as a result of the kind of performance selected by Sandi or by Sandi if a selection of two or more backdrops is offered Sandi for a particular kind of performance. Key card 141 combines the signals from camera 21 and from graphics source 140 and transmits a composite signal to chroma key 142 processor. Processor 142 incorporates backdrop 133 to produce a chroma key still picture or audio visual signal that depicts backdrop 133 in all areas of the still picture or video that are not occupied by Sandi. The finalized chroma key still picture or audio visual signal can be transmitted directly to screen 25 for viewing by Sandi 132 while she records her performance. The finalized chroma key signal can also be transmitted to a recording system 143 (or any other desired recipient or location) for storage in the memory of system 143, and the finalized chroma key signal can be transmitted from system 143 and booth 10 to a selected recipient like the web site of the operator or owner of booth 10. The finalized chroma key signal is also transmitted to a DVD recorder/writer 145 in booth 10 that produces and dispenses a DVD 146 containing Sandi's performance. The DVD 146 can be dispensed into a pick-up tray at any desired location inside or outside of booth 10, but is presently dispensed into a pick-up tray located on the exterior of booth 10 such that Sandi has to exit booth 10 and walk on the exterior of booth 10 to the DVD pick-up tray.

The foregoing paragraph describes process of sending signals from camera 21 and graphics source 140 to key card 141, of sending signals from card 141 to chroma key 142 processor, of sending signals from processor 142 to system 143, of sending signals from system 143 to DVD recorder/writer 145, and of producing and dispensing a DVD. Importantly, this entire process preferably happens automatically, which is critical to producing and dispensing promptly a DVD of a performance just concluded by an individual inside booth 10. During a performance, signals can continuously flow from camera 21 and source 140 through to recorder/writer 145 such that portions of the performance are being recorded and written on a DVD at the same time the remainder of the performance takes place and such that recording the last portion of the performance on the DVD occurs at about the same time or soon after the performance is completed; or, alternatively, the performance can be stored at card 141, key 142, system 143, DVD recorder/writer 145 or another point along the processing path and only be written and recorded on a DVD after the entire performance is concluded. Minimizing the amount of time an individual spends in booth 10 is important in enhancing the commercial viability of booth 10.

Providing Portrait and Landscape Picture Outputs

Camera 21 is shown in more detail in FIGS. 40 to 43 and includes Fujinon SDTV lens 134, camera body 135 and rotary table 137. Camera 21 moves vertically up and down along rail box 136 in the manner indicated by arrows 139 in FIG. 41. Such vertical movement of camera 21 is controlled by an individual inside booth 10 using a joystick or another desired control unit. The longitudinal axis of camera 21 is presently generally perpendicular to an individual 132 in booth 10 and to the vertically oriented portion of screen 131. If desired, a system can be provided to tilt camera 21 upwardly in the manner indicated by arrow 146 in FIG. 42, or to tilt the camera downwardly, so that longitudinal axis of the camera is at an angle with respect to the vertically oriented portion of screen 131 or to an individual 132 standing in booth 10.

As is indicated by arrows 138 in FIG. 41, table 137 rotates lens 134 and body 135 through ninety degrees of travel between two operative positions. In the first operative position, camera 21 produces a "landscape" picture of an individual standing inside booth 21 that is the type of picture shown in display screen 25 in FIG. 30 and that, accordingly, includes about 50% to 75% of the person's body. Since an individual controlling the vertical position of camera 21 normally wants to include his or her head in the picture, what is depicted on screen 25 when camera 21 is in the first operative position typically comprises 50% to 75% of the person's body beginning with the head and extending a limited distance down the person's body.

Figure 45:
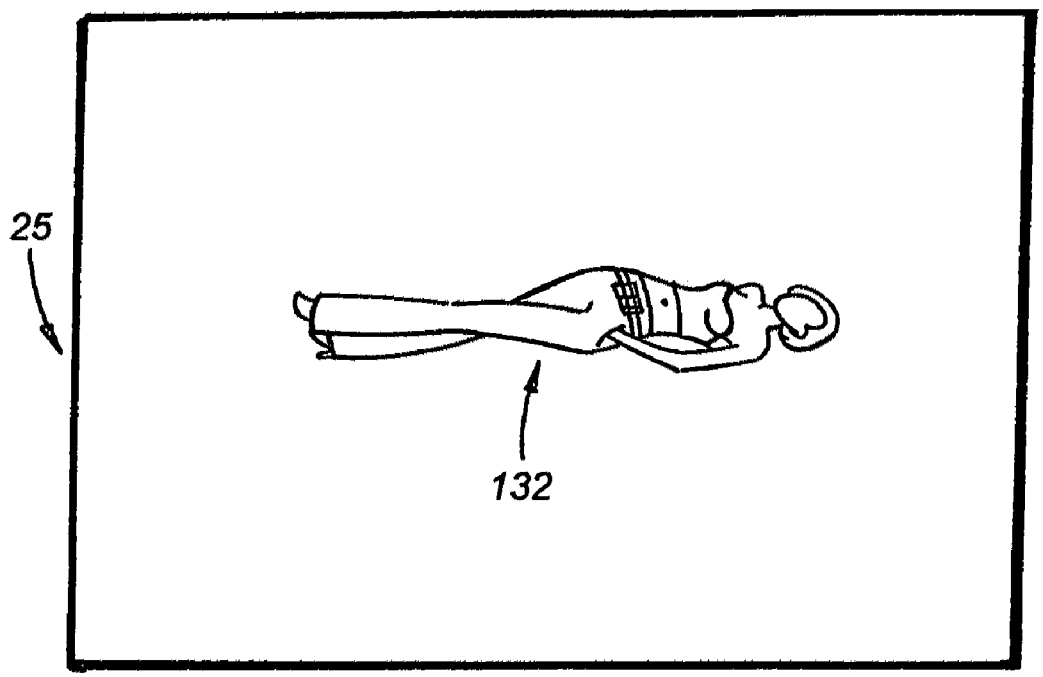
FIG. 45 is a front view of a display screen utilized inside a studio booth and depicting the display that would appear if a camera signal were not adjusted.

When camera 21 is rotated ninety degrees from the first to the second operative position, camera 21 produces a "portrait" picture of the full body of an individual standing in booth 10. The picture produced by camera 21 would, if transmitted direction to display screen 25 without processing, appear in the manner depicted in FIG. 45, with the individual 132 horizontally oriented on her side. In order to compensate for this, software or other controls rotate by ninety degrees the picture produced by camera 21. This software or control can be located in key card 141 or chroma key 142 or at another location before the finalized chroma key signal is received and displayed by display screen 25. As a result, when the full body picture reaches screen 25 and recording system 142, it is upright in the manner illustrated in FIG. 38.

Figure 44:
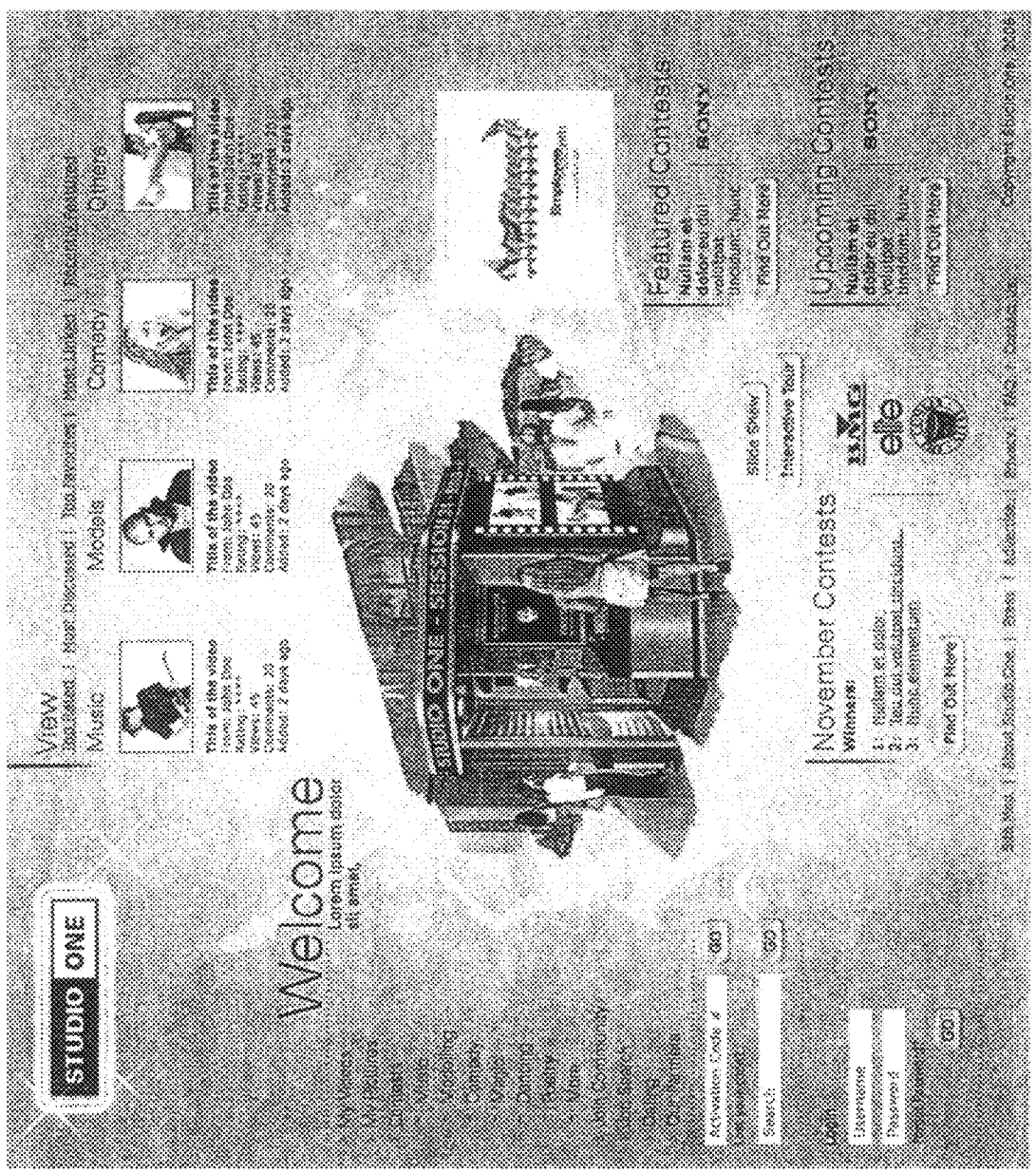
FIG. 44 is a view illustrating a mock-up of a web site home page for an owner or operator of a studio booth.

A mock-up of an Internet home page of the type that can be utilized by the owner or operator of one or more booths 10 is illustrated in FIG. 44. The STUDIO ONE home page in FIG. 44 is operated in conventional manner by inserting, if necessary, required information and by then clicking on desired portions of the web page to go to the next associated web page. For example, in the lower left corner of the web page of FIG. 44, the words "Activation Code #" appear in an information box. The user would use his mouse to click on the box and then use his or her keyboard to insert the activation number in the box, after which he or she clicks on the "GO" button to the right of the box to go to an area of the web site that would have his or her performance that was recorded in booth 10 in connection with the activation card. For example, if after she conducted and recorded her Performance No. 52 in a booth 10, Sandi Martin retained the activation card illustrated in FIG. 27, she would insert in the "Activation Code #" information box in FIG. 44 her activation number of 562389XT (FIG. 27), and with her mouse click on the "GO" button to the right of the information box to go to an area of the web site that stored and would play her performance.

Similarly, in the lower left hand corner of the web page of FIG. 44 there are boxes containing "Username" and "Password". Sandi could type in these boxes her user name and password to access another portion of the web site, which portion could comprise a "MYSTUDIO" web site similar to MY PLACE™ or to other "personal" web sites that permit individuals to list information about themselves and communicate with individuals at other similar web site.

Figure 39:
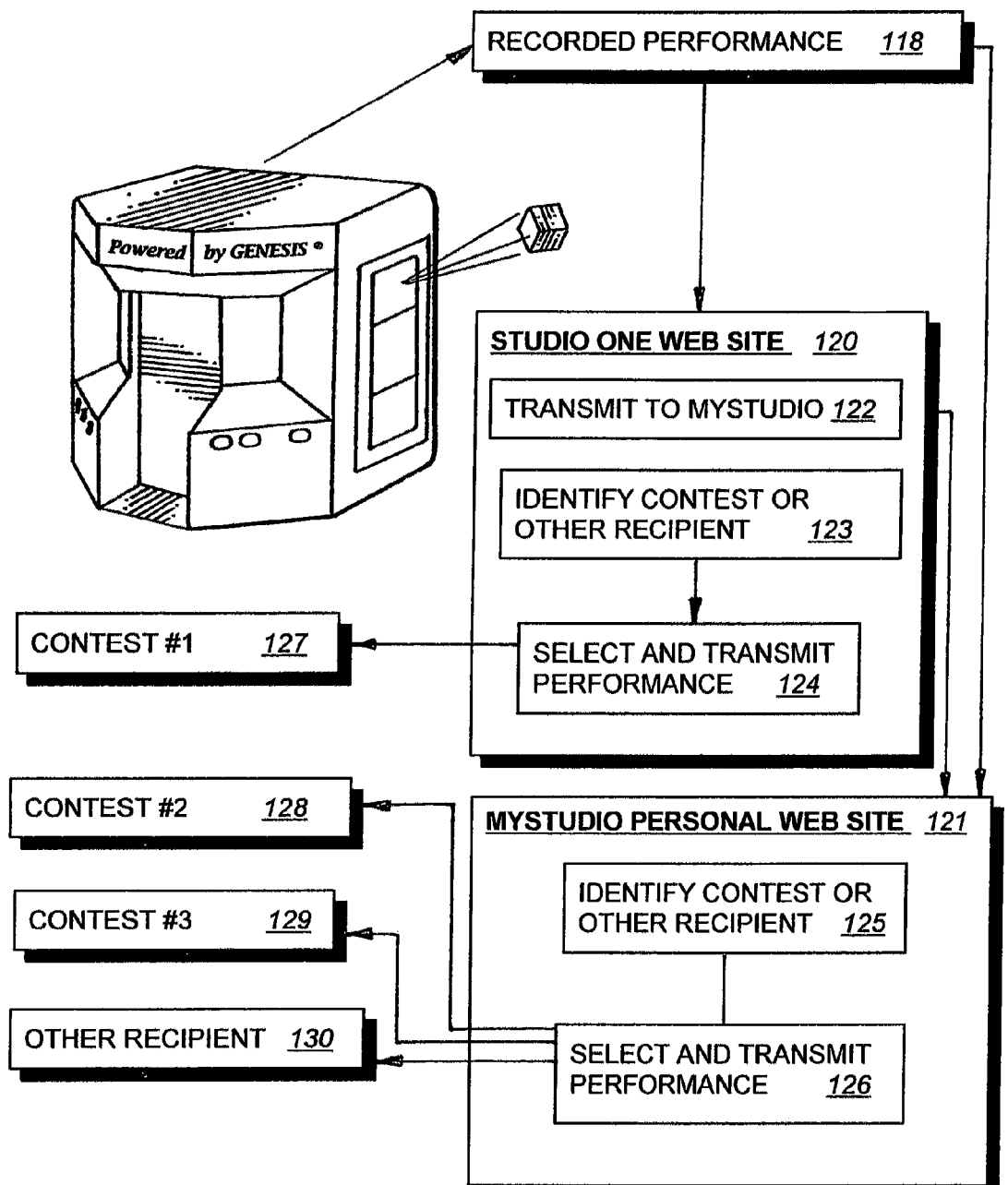
FIG. 39 is a block flow diagram illustrating how a recorded performance produced by a studio booth can be used on multiple occasions by the owner of the performance (or by the owner's agent, licensee, etc.) after the performance is transmitted to a web site.
Figure 43:
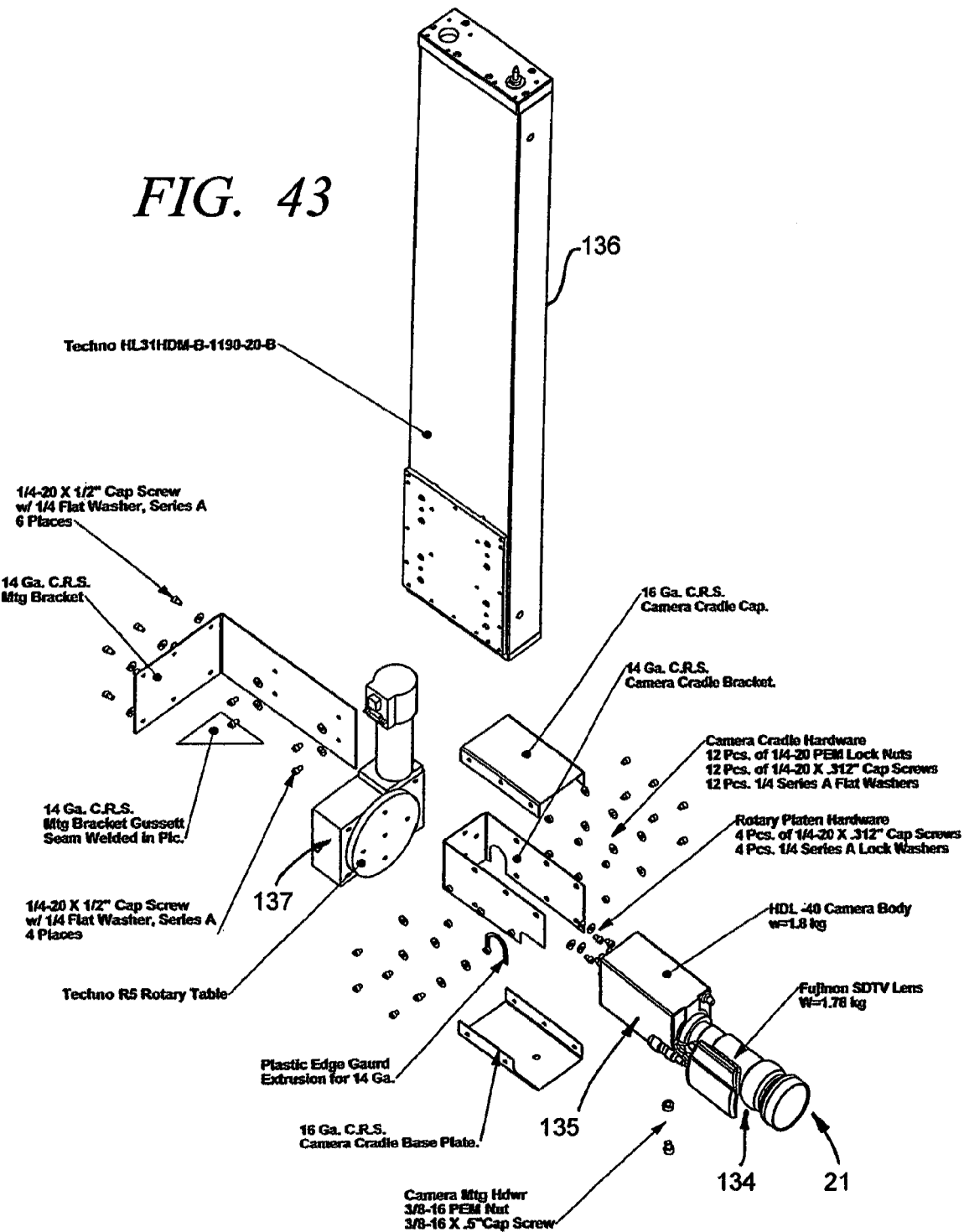
FIG. 43 is an exploded view of the camera system of FIG. 40 illustrating further construction details thereof.

As is illustrated in FIG. 39, once an individual utilizes an activation code to access a performance 118 that is at the STUDIO ONE web site, the individual can elect to transmit 122 the performance to the individual's personal MYSTUDIO web site. In another embodiment of the invention, after identifying 123 one or more on-going contests or possible recipients at the STUDIO ONE web site or another web site, the individual can transmit 124 a performance to a contest or other recipient a performance stored at the STUDIO ONE web site in order to enter such contests. The STUDIO ONE web site can agree to store for a selected limited period of time or for an indefinite period of time a performance conducted and recorded by an individual in a booth 10.

In a further embodiment of the invention, if the individual has a performance transmitted to and stored at his or her personal MYSTUDIO web site (or to a personal web site of some other name), then after identifying 125 one or more contests 128, 129 or other potential recipients 130, the individual can transmit 126 the performance from his or her personal web site to selected contest(s) or recipient(s) for consideration by the contest(s) or recipient(s). In this manner, the individual can utilize over and over a performance professionally recorded in a booth 10. This embodiment of the invention is important because the ability to use conveniently over and over a recorded performance helps to guarantee that the MY STUDIO web site 44 and/or MYSTUDIO web site will continue to generate traffic visiting the web sites.

Transmission of a Live or Delayed Broadcast

Figure 47:
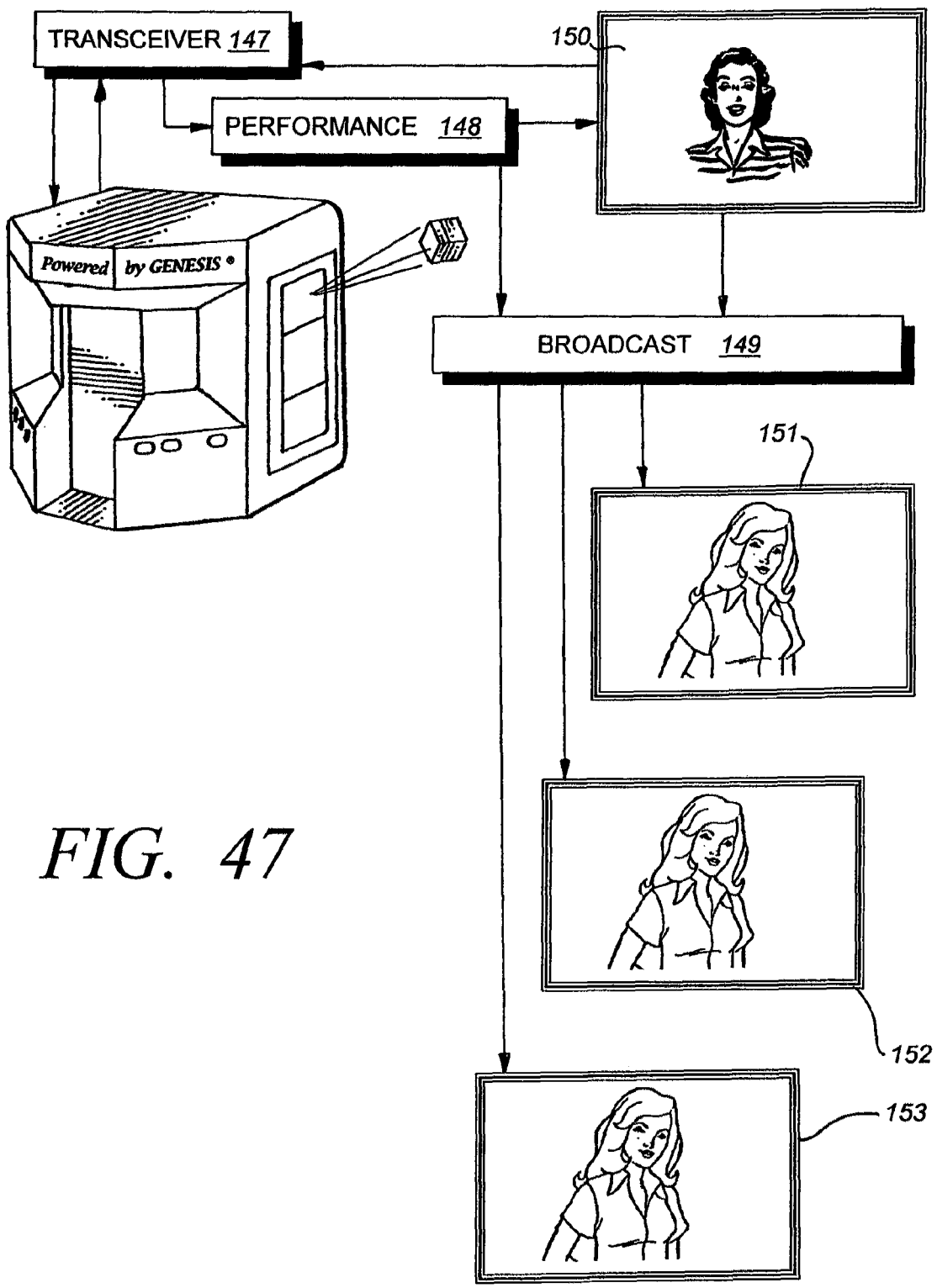
FIG. 47 is a block flow diagram illustrating a system for broadcasting an interview including an individual in a studio booth and an interviewer remote from the studio booth.

In a further embodiment of the invention illustrated in FIG. 47, audio and video of an interviewer at a remote location is received by the transceiver 147 of a studio booth and is displayed on the interior of the booth such that the video of the interviewer appears on a screen 150 inside the booth and a customer (i.e., a performer) inside the studio booth views screen 150 and hears the interviewer. At the same time, the camera-microphone system inside the studio booth produces audio and video of the customer in the booth and transmits the same to a screen and audio speaker located adjacent the interviewer such that the interviewer can, at the same time the customer is viewing and listening to the interviewer, view and listen to the customer. In this fashion, the interviewer can conduct an interview of the customer. The interview can be broadcast 149 to a plurality of remote television, computer, or other display screens 151, 152, 153. The broadcast can be accomplished via cable, satellite, etc. utilizing fiber optic, infrared, or any other electromagnetic signals.

Figure 48:
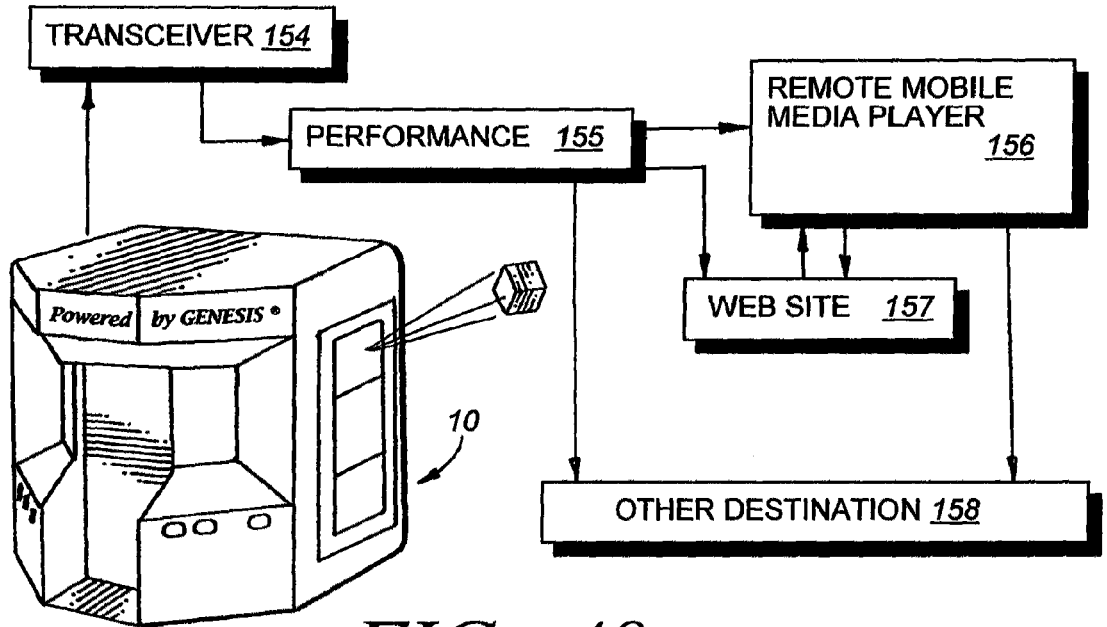
FIG. 48 is a block flow diagram illustrating the transmission from the studio booth of a performance to a remote mobile media player or other designated destination.

Transmission of a Performance to a Cell Phone or Other Remote Mobile Media Player In another embodiment of the invention illustrated in FIG. 48, a performance 155 recorded in a studio booth 10 is transmitted via a transceiver 154 at, in, or adjacent the booth 10. The performance is sent via cable, satellite, cell phones transmission towers, etc. utilizing fiber optic, infrared, or any other electromagnetic signals. The performance is transmitted to a cell phone or other remote mobile media player 150, to an Internet web site 157, or to a receiver at another selected destination 158.

Figure 49:
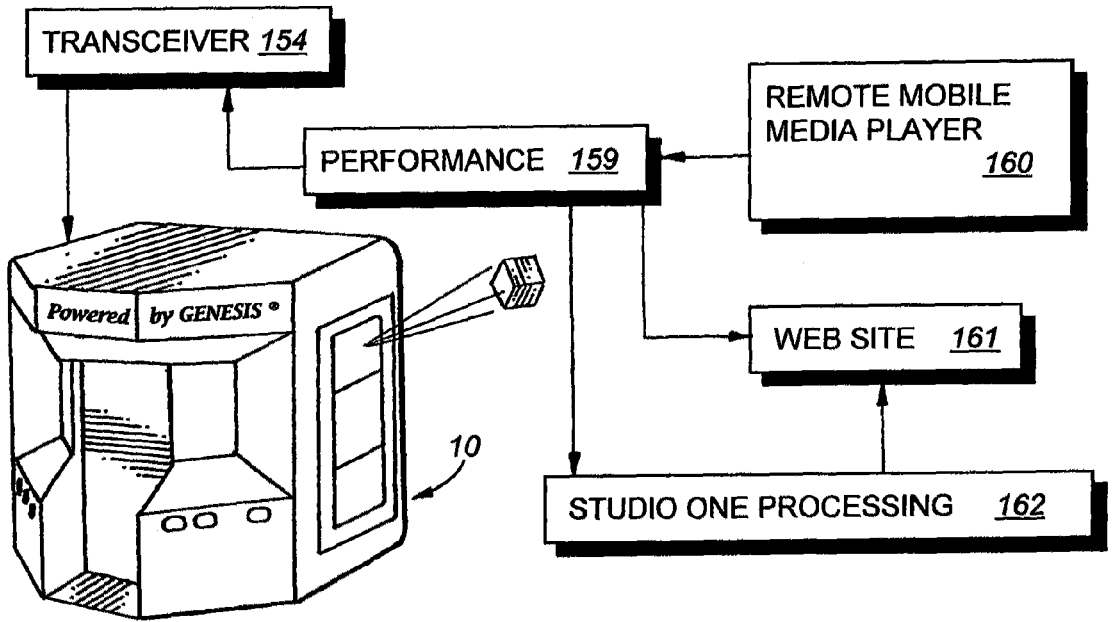
FIG. 49 is a block flow diagram illustrating the transmission from a remote mobile media player to a studio booth or other selected destination.

Transmission of a Performance from a Remote Mobile Media Player to a Studio Booth In another embodiment of the invention illustrated in FIG. 49, a performance 159 is sent from a remote mobile media player 160 to a transceiver 154 in, at, or adjacent a studio booth 10. The performance is transmitted from player 160 via cable, satellite, cell phones transmission towers, etc. utilizing fiber optic, infrared, or any other electromagnetic signals. The performance can also be transmitted to a web site 161 or to a processing location operated by the owner or operator of the booth 10, which owner in FIG. 49 is designated Studio One.

Selection of Auxiliary Sound Accompaniment in Studio Booth

Figure 50:
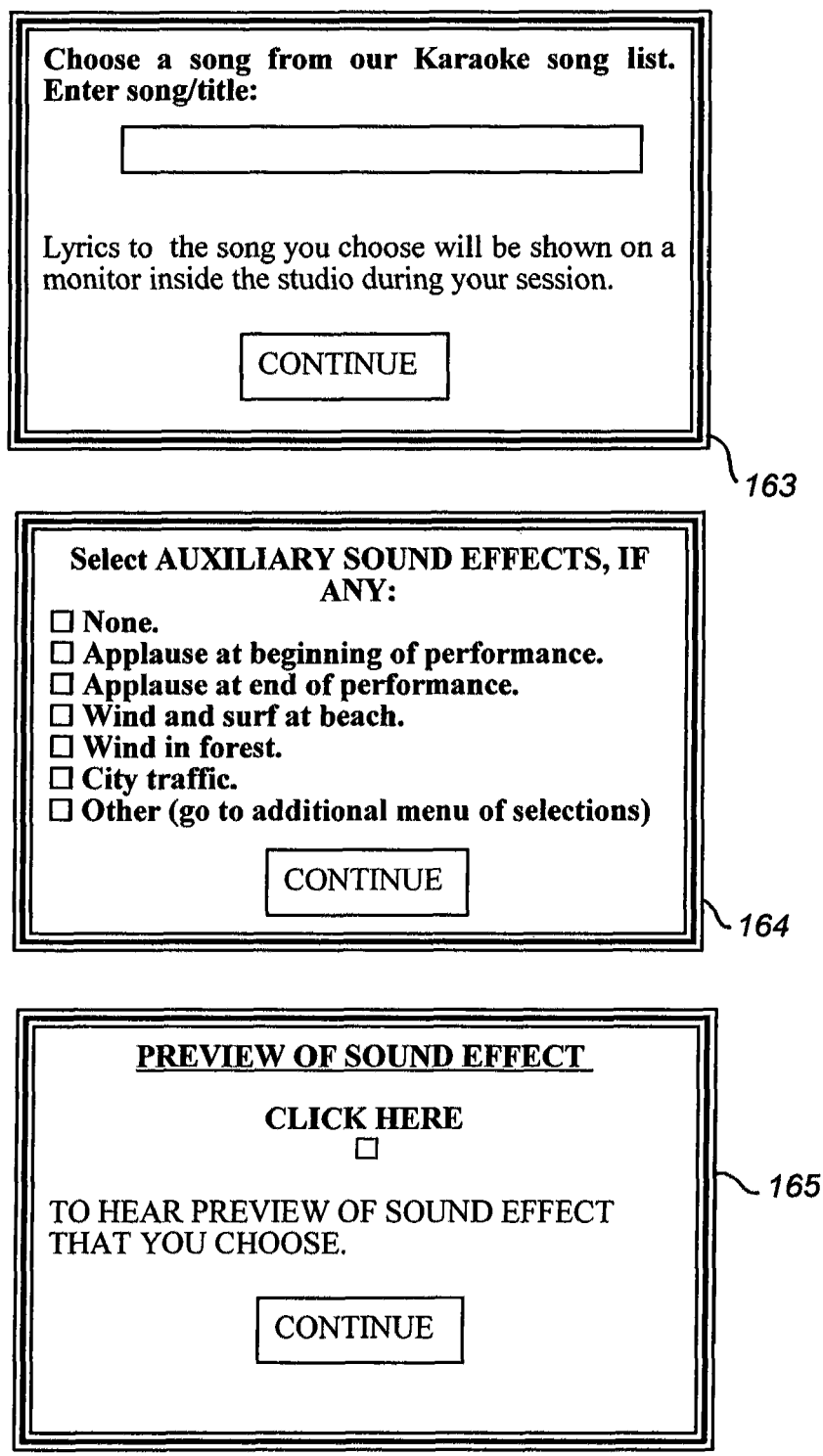
FIG. 50 is a block flow diagram illustrating the selection in a studio booth by a customer of auxiliary sound effects.

In one embodiment of the invention illustrated in FIG. 50, a customer registering to use a studio booth 10 is provided with the option of selecting auxiliary sound effects. FIG. 50 illustrates one of a variety of scenarios that can be provided a customer when the customer is registering to use the booth, or, is inside the booth ready to record a performance. In FIG. 50, it is assumed that the customer is at a location outside the booth and is registering to use the booth to record a performance. One location of the customer outside the booth is at one of the registration stations provided at the booth. Another possible location of the customer outside the booth is at the customer's computer where he is registering at an Internet web site to use the booth to record a performance.

In FIG. 50, during the registration process the customer is given the option in interactive screen display 163 to select a song. After the customer selects a song and presses his finger against the display screen over "CONTINUE", the next display 164 appears on the display screen. Display 164 gives the customer the option of selecting an auxiliary sound effect. The customer makes a selection by pressing his finger over the box at the end of one or more of the selections shown on display 164. By way of example, and not limitation, the customer presses screen over the box preceding "Applause at the beginning of performance" and presses the screen over the box preceding "Applause at end of performance", after which he presses the screen over "CONTINUE" to cause the next display 165 to appear on the screen. Display 165 permits the customer to, if he wishes, hear a preview of the sound effect, after which the customer presses the screen over "CONTINUE" to cause the next display to appear.

The Illusion

One of the advantages of the studio booth of the invention is that it produces a still photograph or video that realistically makes it appear that the customer(s) (i.e., performer(s)) utilizing the booth are not in the limited confines of the booth but instead are at a location having a scenic backdrop that is much larger and much different in appearance than the inside of the booth. Various features of the booth of the invention are critical in producing this illusion.

A. Restricted Size of Studio Booth. The studio booth occupies a spatial volume that fits within a footprint volume defined as bounded by a horizontally oriented polygonal footprint area on the floor or ground—the footprint having a perimeter—and bounded by vertically oriented footprint planes that are normal to the ground and extend upwardly from each side of the footprint perimeter. For example, if the studio booth is shaped like a cube ten feet on a side, the spatial volume occupied by the booth is 10×10×10=1000 cubic feet. The footprint planes each extend upwardly to a height equivalent to the height of a studio booth. The height of the booth can vary as desired. The polygon is a simple convex polygon like a triangle, rectangle (including a square), pentagon, hexagon, octagon, etc. The polygon has a width and has a length that is normal to the width. At least either the length or width is measured along a line parallel to one side of the polygon. The width and the length each span the complete distance from one side or point of the polygon to the other side or point of the polygon. The studio booth fits within said footprint volume when substantially the entire spatial volume occupied by the studio booth fits within said footprint volume. Substantially the entire spatial volume of the studio booth fits within the footprint volume when at least ninety-five percent of the total spatial volume occupied by the studio booth fits within the footprint volume.

Figure 52:
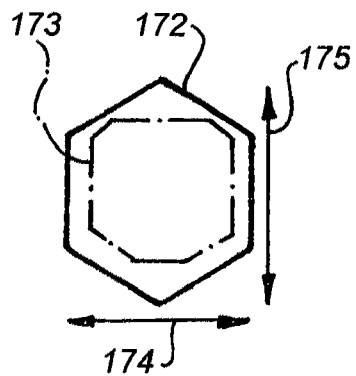
FIG. 52 is a top view illustrating a booth footprint.

In FIG. 52, the polygonal footprint area 172 comprises a hexagon having a width indicated by arrows 174 and a length indicated by arrows 175. The base 173 of a studio booth lies within the perimeter of hexagonal area 172. The portions (not shown) of the studio booth extending upwardly from base 173 do not extend laterally outwardly from base 173, consequently, the entire volume of the studio booth lies within the footprint volume.

Figure 53:
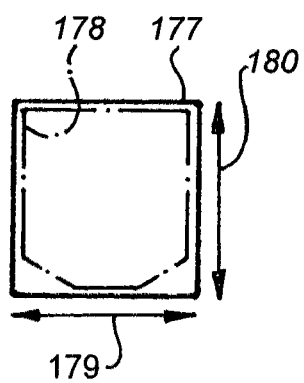
FIG. 53 is a top view illustrating a booth footprint.

In FIG. 53, the polygonal footprint area 177 comprises a rectangle (i.e., a square) having a width indicated by arrows 179 and a length indicated by arrows 180. The base 178 of a studio booth lies within the perimeter of rectangular footprint area 177. The portions (not shown) of the studio booth extending upwardly from base 178 do not extend laterally outwardly from base 178, consequently, the entire volume of the studio booth lies within the footprint volume.

Figure 54:
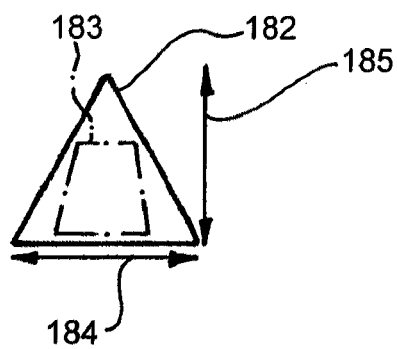
FIG. 54 is a top view illustrating a booth footprint.

In FIG. 54, the polygonal footprint area 182 comprises a triangle having a width indicated by arrows 164 and a length indicated by arrows 185. The base 183 of a studio booth lies within the perimeter of the polygonal triangle area 182. Portions (not shown) of the studio booth extending upwardly from base extend laterally outwardly from base 183. The portions account for twenty percent of the total spatial volume occupied by the studio booth. Of the portions the extend laterally outwardly from base 183, half of the spatial volume of these portions extend outwardly past the vertical footprint planes that extend upwardly from the sides comprising the perimeter of triangular area 182. Consequently, ten percent of the volume of the studio booth extends outwardly past and away from the footprint volume. This means that substantially the entire volume of the studio booth does not lie within the footprint volume. If the width and height of each of the footprint areas in FIGS. 52 to 53 is identical, then base 178 of the studio booth of FIG. 53 fits within the footprint volume associated with the rectangular footprint area 177 but does not fit within the footprint volume associated with the triangular footprint area 182 of FIG. 54. As long as the spatial volume of the studio booth of FIG. 53 fits substantially in at least one footprint volume having a simple convex polygonal cross section with a prescribed width and length, then the studio booth is deemed to fit in a footprint volume. The fact that the spatial volume of a studio booth does not fit in one footprint volume having a polygonal cross section with the designated width and length is of no moment as long as the spatial volume of the booth fits into a differently shaped footprint volume having a polygonal cross section with the designated width and length.

In one preferred embodiment of the invention, a studio booth lies substantially within a footprint volume in which the polygon is a square having sides each ten feet long. Being able to record a performance in such a small booth and to produce a realistic appearing illusion that the individual is in an area with a much larger background is difficult.

In another preferred embodiment of the invention, the polygon utilized to determine a footprint volume can not have an excessively small width in comparison to the length of polygon. Otherwise, utilizing a relatively small studio booth is impractical. Consequently, the polygon should have dimensional parity. Dimensional parity requires the polygon to have a width that is not greatly different from the length of the polygon, which means that in order for the polygon to have dimensional parity, the ratio of the width of the polygon to the length of the polygon is in the range of 1:0.5 to 1:2, preferably 1:0.75 to 1:1.25, and most preferably 1:0.8 to 1:1.2.

B. Subject Perspective Distortion.

Since a performance by a customer (i.e., performer) in a studio booth is being photographed in a small space, subject perspective distortion can inadvertently be easily achieved. Subject perspective distortion occurs when one portion of a performer's body is sized out of proportion with respect to another portion of a performer's body. If, for example, the performer's nose or face appears abnormally large with respect to the remainder of the performer's body, then subject perspective distortion has occurred.

Figure 51:
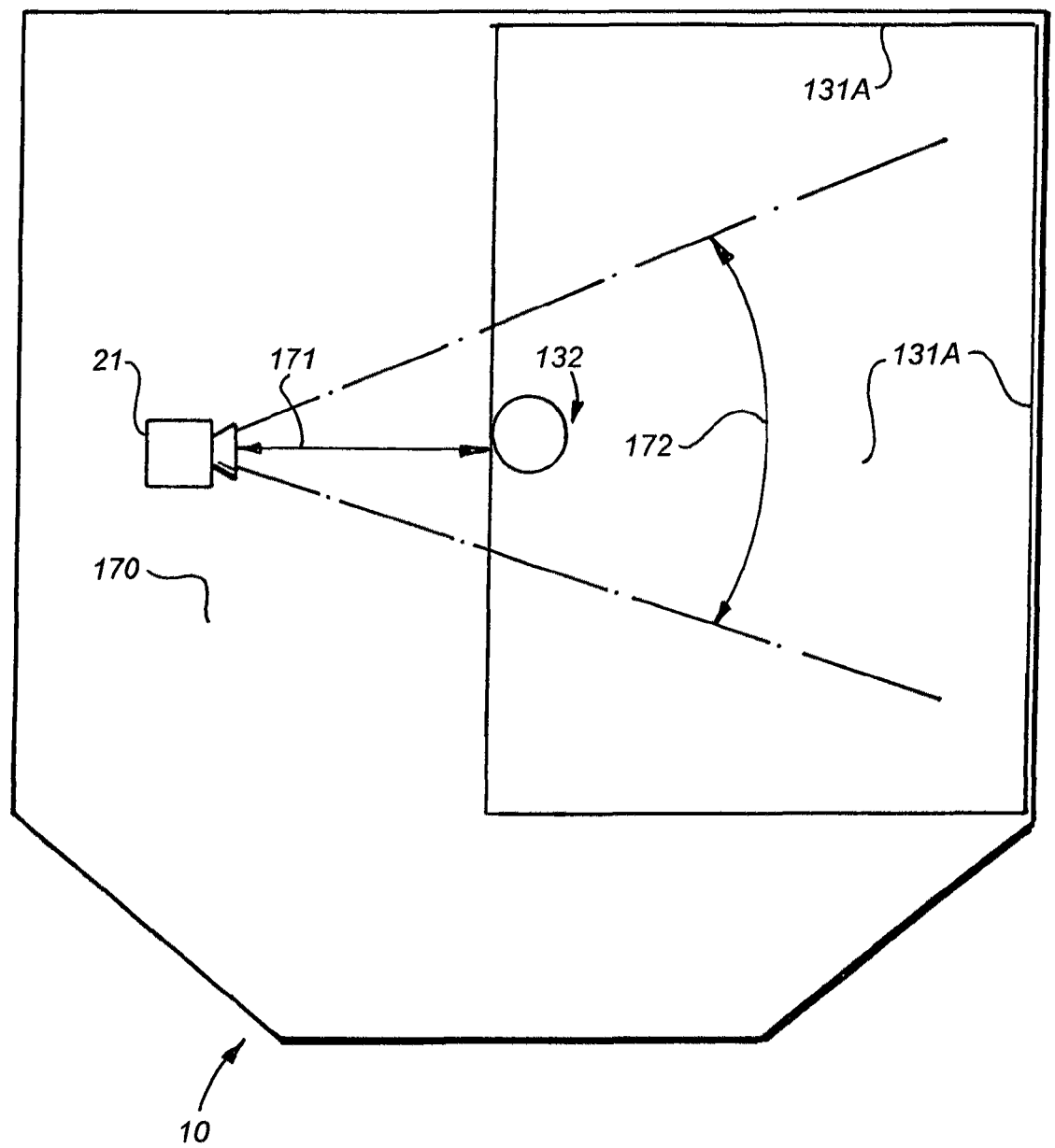
FIG. 51 is a top view of the floor of a studio booth illustrating minimum camera distance and horizontal field of view.

In accordance with the invention, one important step in minimizing subject perspective distortion is to define a minimum distance that a performer 132 must be from the camera 21 in the booth 10. In a booth constructed in accordance with the invention, in particular in a booth that fits within a footprint volume in which the polygon is a rectangle having sides each ten feet long, this minimum distance is indicated by arrows 151 in FIG. 51 and is equal to three feet.

Another important step in minimizing subject perspective distortion pertains to the camera lens utilized in the practice of the invention. While the field of view of the lens can vary as described, the lens of camera 21 preferably has a horizontal field of view (indicated by arrows 172 in FIG. 51) in the range of fifty-two degrees to sixty-six degrees. The field of view of a camera ordinarily is a function of three parameters:
1. The dimensions of the film format or image sensor;
2. The focal length of the photographic lens projecting the image; and,
3. The kind and degree of distortion of the lens.

If a lens projects rectilinear (non-spatially-distorted) image, the film format or image sensor dimensions completely define the angle of view for any given lens focal length. Field of view is usually measured one of three ways:
1. Horizontally (from the left to right edge of the frame).
2. Vertically (from the top to bottom of the frame).
3. Diagonally (from one upper corner of the frame to its opposite lower corner).

Lens are often referred to by terms that express their field of view.
1. Ultra wide-angle lenses, also know as fisheye lenses, cover up to 180 degrees, or even wider in special cases.
2. Wide-angle lenses generally cover between 100 and 60 degrees.
3. Normal, or Standard lenses generally cover between 50 and 25 degrees.
4. Telephoto lenses generally cover between 15 and 10 degrees.
5. Super telephoto lenses generally cover between eight degrees through less than one degree.
6. Zoom lenses are a special case wherein the focal length, and hence angle of view, of the lens can be altered mechanically without removing the lense from the camera.

C. Subject-Background Correlation Distortion. Subject-background correlation distortion occurs when the spacing between the performer(s) and background appears abnormal (i.e., either too close together or to far apart), and/or, the performer appears abnormally large or small with respect to the background. For example, if a recording produced in a studio booth shows a German Shepard dog standing behind a performer and the dog is as tall as the performed, then the performer appears abnormally small in comparison to the dog and there is subject-background correlation distortion. Or, if a recording produced in a studio booth shows a performer standing on a beach in the ocean surf, and it appears that there are several palm trees lined up one behind the other just behind the performer, this is subject-background correlation distortion because even though it may be possible for palm trees to be growing one-behind the other on the beach close to the surf, such is highly unlikely and looks abnormal.

One principal way of minimizing subject-background correlation distortion is to, after selecting a scenic background that can be incorporated in a performance recorded in a studio booth, actually viewing the scenic background in combination with a performer recorded in the booth to determine if the performer-background combination looks normal. When the performer-background combination is viewed, it is important to view the combination at a normal viewing distance of at least twelve inches away from the combination, preferably a viewing distance in the range of twelve to twenty-four inches. Viewing a still photograph or video at an abnormal distance can make the photograph or video appear abnormal.

Another way of minimizing subject-background correlation distortion is to pre-select one or more backgrounds and require that a performer utilize one of the pre-selected backgrounds. The pre-selected backgrounds typically, but not necessarily, are selected to correlate with or relate to a particular kind of performance or event. For example, if a performer is participating in a contest, then the owners or operators of the contest can select backgrounds that relate to the contest. If the contest is a singing contest, the backgrounds may each consist of a stage or stage setting that makes it appear that the performer is singing on a stage in an auditorium. If the performer is conducting an interview for a job, the background(s) selected may consist of a conference room setting or a restaurant settings.

A further way of minimizing subject-background correlation distortion, and of minimizing subject distortion, is to pre-select a camera setting(s) that must be used by a performer. For example, if a performer is participating in a singing contest, then the owners or operators of the contest can select a camera lens setting or camera position the will show the entire body of a performer that is participating in the contest. If a performer is participating in a modeling contest, then the owners or operators of the contest can, if desired, select a camera setting that will only show the head and shoulders of a performer that is participating in the contest. When a camera setting is pre-selected, this setting can be imposed on a performer in any desired manner. For example, when a performer registers to record for a contest a performance in a studio booth the software utilized in the booth can automatically set the camera lens or other adjustable portion of the camera at the pre-selected setting and not permit the performer to adjust the camera. Or, when a performer registers to record a performance, the performer can utilize a touch screen that is located inside the booth to select one of two or more camera positions that are offered under contest rules. Once the performer selects a camera setting, the control software in the booth functions to cause the camera to adjust itself to the selected setting. Or, when a performer registers to record a performance, the performer can adjust the camera setting from inside the booth, but the booth control system will not allow the performer to record a performance until the performer adjusts the camera to a position that was pre-selected for the contest.

Low Resolution Transmission

Immediately after, soon after (i.e., within thirty minutes, preferably within fifteen minutes, most preferably within five minutes following the conclusion of the performance-unless the performer elects at the booth to cancel or not transmit the performance), or while a performance is recorded in a studio booth 10, the performance is initially transmitted to a web site owned by the owner or operator of the booth or is transmitted to another designated location. This initial transmission typically is done is a low resolution format, which format is less than 1080 lines of horizontal resolution. The performance is temporarily stored in computer memory at the booth in a high resolution format comprising 1080 or more lines of horizontal resolution. The performance is later transmitted (typically at night), if desired, in a high resolution format. The low resolution-high resolution transmission dichotomy is believed important to the practical and economical utilization of the invention because it facilitates the prompt transmission at likely a relatively low cost in a low resolution format (typically during daytime or evening hours) while preserving a high resolution format of the performance in the event such is needed.

Two-way Transmission of Content

The economic viability of a studio booth 10 constructed in accordance with the invention is enhanced because the booth 10 produces and transmits to selected locations remote from the booth 10 content in the form of performances by customer utilizing the booth while the booth 10, at the same time, receives advertising and other content that is shown on video displays 12, 32, 43, 44 on the exterior or interior of the booth and/or that is heard audibly on speakers located on the exterior or interior of the booth Evaluation of Performance on the Merits Another embodiment of the invention enables a performer to request a substantive or other review of a performance. For example, in the middle menu entitled "CHOOSE A SESSION" in FIG. 11, one of the selections offered could be:

Have your performance evaluated.

If the performer makes this selection, a subsequent menu or display allows the performer to enter a postal address, e-mail, cell phone number, etc. to which the evaluation report is forwarded. The report can be transmitted in a printed format, or, the evaluator can contact the performer directly and provide a verbal report If desired, the performer can be asked to pay an additional fee for the evaluation. The evaluation can take any desired form. For example, if the performer is singing, the evaluation could comprise comments on (1) whether the performer remained on key, (2) the "warmth" of the singer's voice, (3) the uniqueness of the singer's voice, (4) the singer's diction, (5) the singer's hand motions, (6) the singer's clothing, (7) the singer's facial expressions, (8) the singer's hair style and, if any, makeup, (9) the singer's pacing of the song, (10) how the singer ended the song, (11) whether the singer conveyed a desirable mood.

Having described the presently preferred embodiments and best mode of the invention in such terms as to enable those of skill in the art to understand and practice the invention, I claim:

1. A method to conduct a broadcast interview by producing in an area of restricted size in a realistic manner while minimizing perspective distortion and subject distortion a recording of an individual that produces the illusion that the individual is located in a larger area, comprising the steps of
   (a) providing a studio booth including
      (i) an interior with a front wall, a rear wall, side walls extending between said front wall and rear wall, a floor, and a ceiling,
      (ii) an audio and video system to detect and generate audio-visual signals comprising a recording of at least one performance conducted in said booth, said system including a digital camera mounted at said front wall,
      (iii) a chroma key screen extending over at least a portion of said rear wall to produce background light that is, along with the performance conducted in the booth, detected by said digital camera,
      (iv) a transmitter-receiver to send said audio-visual signals to a selected location remote from said booth and to receive audio-visual signals from a selected location remote from said booth to conduct an interview,
      (v) a computer system to generate backdrop signals representing a scenic backdrop and to integrate said audio-visual signals and said backdrop signals to produce a recorded performance,
      said booth having a footprint fitting within a rectangular area having a greatest side dimension of ten feet;
   (b) selecting a lens system for said digital camera with a horizontal field of view that minimizes subject distortion of an individual performing in said interior of said booth;
   (c) defining, to minimize subject distortion, a minimum distance that an individual stands away from said camera when said individual is in the interior of said booth to conduct a performance;
   (d) selecting a scenic backdrop
      (i) to minimize subject-background correlation distortion, (ii) depicting an area other than said interior of said studio booth;

(e) conducting and recording a live interview of the individual in said interior of said booth and no closer to said camera than said minimum distance and generating with said computer system a recording of the performance comprising audio visual signals of said live interview integrated with backdrop signals of said selected scenic backdrop selected in step (d), said live interview conducted by another individual at a location remote from said booth; and, (f) transmitting to a selected remote location with said transmitter said recording produced in step (b).

* * * * *